United States Patent
Miwatashi et al.

(10) Patent No.: US 10,968,231 B2
(45) Date of Patent: Apr. 6, 2021

(54) SUBSTITUTED CYCLYL-ACETIC ACID DERIVATIVES FOR THE TREATMENT OF METABOLIC DISORDERS

(71) Applicants: TAKEDA PHARMACEUTICAL COMPANY LIMITED, Osaka (JP); SCOHIA PHARMA, INC, Kanagawa (JP)

(72) Inventors: Seiji Miwatashi, Tokyo (JP); Yasufumi Miyamoto, Kanagawa (JP); Koji Watanabe, Kanagawa (JP); Yayoi Nakayama, Kanagawa (JP); Yuko Hitomi, Kanagawa (JP); Jumpei Aida, Kanagawa (JP); Nobuyuki Takakura, Kanagawa (JP); Hideki Furukawa, Kanagawa (JP); Naoyoshi Noguchi, Kanagawa (JP); Yasuhiro Hirata, Kanagawa (JP); Shizuo Kasai, Kanagawa (JP); Toshitake Kobayashi, Kanagawa (JP); Tsuyoshi Maekawa, Kanagawa (JP); Satoshi Sasaki, Kanagawa (JP); Shigemitsu Matsumoto, Kanagawa (JP)

(73) Assignees: SCOHIA PHARMA, INC., Kanagawa (JP); TAKEDA PHARMACEUTICAL COMPANY LIMITED, Osaka (JP)

( * ) Notice: Subject to any disclaimer, the term of this patent is extended or adjusted under 35 U.S.C. 154(b) by 2 days.

(21) Appl. No.: 16/497,141

(22) PCT Filed: Mar. 29, 2018

(86) PCT No.: PCT/JP2018/014501
§ 371 (c)(1),
(2) Date: Sep. 24, 2019

(87) PCT Pub. No.: WO2018/182050
PCT Pub. Date: Oct. 4, 2018

(65) Prior Publication Data
US 2020/0377509 A1     Dec. 3, 2020

(30) Foreign Application Priority Data
Mar. 31, 2017 (JP) ................... 2017-072813

(51) Int. Cl.
C07D 491/052 (2006.01)
C07D 211/22 (2006.01)
C07D 401/12 (2006.01)
C07D 401/14 (2006.01)

(52) U.S. Cl.
CPC ........ *C07D 491/052* (2013.01); *C07D 211/22* (2013.01); *C07D 401/12* (2013.01); *C07D 401/14* (2013.01)

(58) Field of Classification Search
CPC .............. C07D 491/052; C07D 211/12; C07D 401/12; C07D 401/14

USPC ....................................... 514/233.8
See application file for complete search history.

(56) References Cited

U.S. PATENT DOCUMENTS

| | | | |
|---|---|---|---|
| 8,030,354 B2 | 10/2011 | Brown et al. | |
| 8,450,522 B2 | 5/2013 | Brown et al. | |
| 9,181,186 B2 | 11/2015 | Miwatashi et al. | |
| 9,776,962 B2 | 10/2017 | Aida et al. | |
| 9,856,245 B2 | 1/2018 | Huang et al. | |
| 9,908,873 B2 | 3/2018 | Huang et al. | |
| 9,920,040 B2 | 3/2018 | Huang et al. | |
| 2006/0258722 A1 | 11/2006 | Yasuma et al. | |
| 2007/0149608 A1 | 6/2007 | Yasuma et al. | |
| 2007/0244155 A1 | 10/2007 | Sharma et al. | |
| 2009/0012093 A1 | 1/2009 | Fukatsu et al. | |
| 2009/0137561 A1 | 5/2009 | Brown et al. | |
| 2010/0144806 A1 | 6/2010 | Yasuma et al. | |

(Continued)

FOREIGN PATENT DOCUMENTS

| | | |
|---|---|---|
| WO | 2007/106469 | 9/2007 |
| WO | 2009/048527 | 4/2009 |

(Continued)

OTHER PUBLICATIONS

International Search Report dated Jun. 25, 2018 in International (PCT) Application No. PCT/JP2018/014501.

(Continued)

*Primary Examiner* — Kristin A Vajda
(74) *Attorney, Agent, or Firm* — Wenderoth, Lind & Ponack, L.L.P.

(57) ABSTRACT

Provided is a novel aromatic ring compound which may have a GPR40 agonist activity and a GLP-1 secretagogue action. A compound represented by the formula (I): wherein each symbol is as described in the DESCRIPTION, or a salt thereof may have a GPR40 agonist activity and a GLP-1 secretagogue action, may be useful for the prophylaxis or treatment of cancer, obesity, diabetes, hypertension, hyperlipidemia, cardiac failure, diabetic complications, metabolic syndrome, sarcopenia and the like, and may afford superior efficacy.

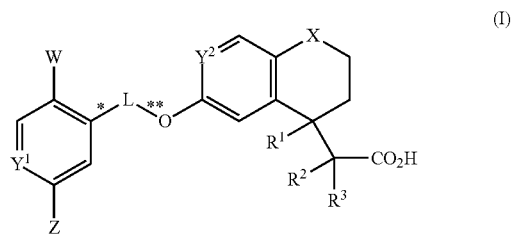

10 Claims, No Drawings

(56) References Cited

U.S. PATENT DOCUMENTS

| | | |
|---|---|---|
| 2010/0298367 A1 | 11/2010 | Brown et al. |
| 2015/0045378 A1 | 2/2015 | Miwatashi et al. |
| 2016/0115128 A1 | 4/2016 | Aida et al. |
| 2017/0044146 A1 | 2/2017 | Huang et al. |
| 2017/0044147 A1 | 2/2017 | Huang et al. |
| 2017/0044148 A1 | 2/2017 | Huang et al. |
| 2019/0071412 A1 | 3/2019 | Miller et al. |
| 2019/0337961 A1 | 11/2019 | Miller et al. |
| 2019/0367495 A1 | 12/2019 | Miller et al. |

FOREIGN PATENT DOCUMENTS

| | | |
|---|---|---|
| WO | 2009/111056 | 9/2009 |
| WO | 2013/122029 | 8/2013 |
| WO | 2015/020184 | 2/2015 |
| WO | 2017/027309 | 2/2017 |
| WO | 2017/027310 | 2/2017 |
| WO | 2017/027312 | 2/2017 |
| WO | 2017/172505 | 10/2017 |
| WO | 2018/081047 | 5/2018 |
| WO | 2018/106518 | 6/2018 |
| WO | 2018/118670 | 6/2018 |
| WO | 2018/181847 | 10/2018 |

OTHER PUBLICATIONS

Du et al., "Improving the Pharmacokinetics of GPR40/FFA1 Full Agonists", ACS Medical Chemistry Letters, vol. 5, No. 4, pp. 384-389, 2014.

Meegalla et al., "Discovery of a novel potent GPR40 fall agonist", Bioorganic & Medicinal Chemistry Letters, vol. 28, pp. 720-726, 2018.

SUBSTITUTED CYCLYL-ACETIC ACID DERIVATIVES FOR THE TREATMENT OF METABOLIC DISORDERS

TECHNICAL FIELD

The present invention relates to a novel aromatic ring compound which may have a GPR40 agonist activity and GLP-1 secretagogue action.

BACKGROUND OF THE INVENTION

Patent document 1 describes the following compound.

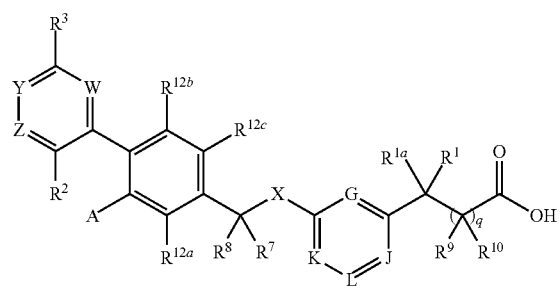

wherein each symbol is as described in patent document 1.
Patent document 2 describes the following compound.

(I-1)

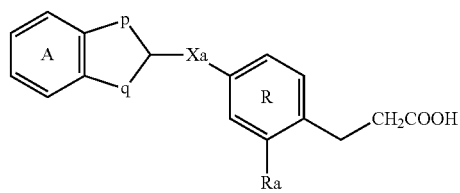

wherein each symbol is as described in patent document 2.
Patent document 3 describes the following compound.

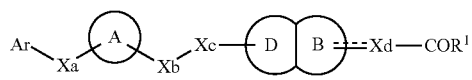

wherein each symbol is as described in patent document 3.
Patent document 4 describes the following compound.

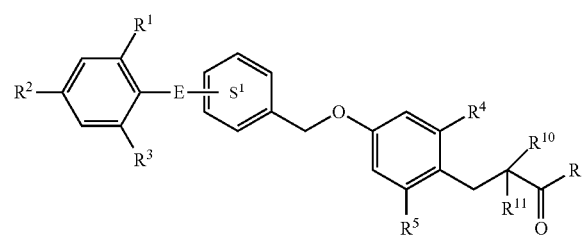

wherein each symbol is as described in patent document 4.

Patent document 5 describes the following compound.

[I]

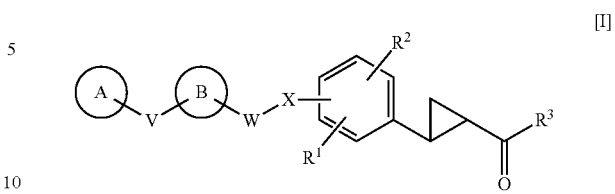

wherein each symbol is as described in patent document 5.
Patent document 6 describes the following compound.

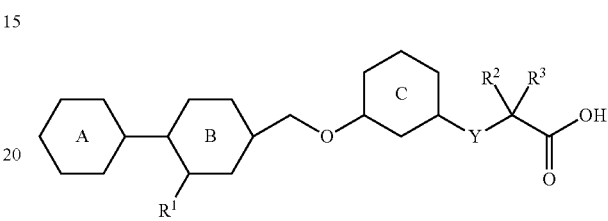

wherein each symbol is as described in patent document 6.
Patent document 7 describes the following compound.

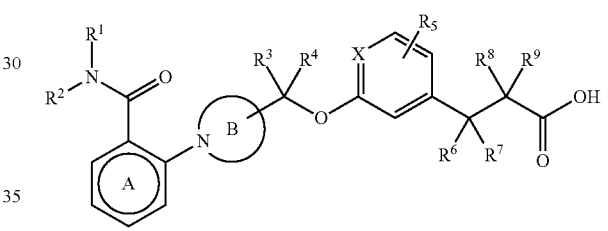

wherein each symbol is as described in patent document 7.
However, no documents specifically disclose the compound of the present application.

DOCUMENT LIST

Patent Documents patent document 1: WO2009/048527
patent document 2: US2009-0012093
patent document 3: US2006-0258722
patent document 4: US2007-0149608
patent document 5: US2010-0144806
patent document 6: WO2013/122029
patent document 7: WO2015/020184

SUMMARY OF THE INVENTION

Problems to be Solved by the Invention

The present invention aims to provide a novel aromatic ring compound which may have a GPR40 agonist activity and GLP-1 secretagogue action, and expected to be useful as an agent for the prophylaxis or treatment of diabetes and the like.

Means of Solving the Problems

The present inventors have intensively conducted various studies and found that a compound represented by the formula (I) may unexpectedly have a superior GPR40 agonist activity and a GLP-1 secretagogue action, and may provide a safe and useful medicament as an agent for the prophylaxis or treatment of a GPR40 receptor-related pathology or disease in mammals. They have completed the present invention based on these findings.

That is, the present invention relates to

[1] a compound represented by the formula (I):

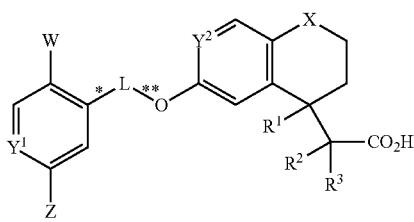

wherein X is an oxygen atom or a bond;
$Y^1$ and $Y^2$ are each independently CH or N;
Z is an optionally substituted alkyl group, an optionally substituted alkoxy group or a halogen atom;
W is an optionally substituted alkyl group, an optionally substituted alkoxy group, —$NR^{W1}R^{W2}$, an optionally substituted carbamoyl group or an optionally substituted cyclic group;
$R^{W1}$ is an optionally substituted alkyl group or an acyl group;
$R^{W2}$ is a hydrogen atom or a substituent;
L is

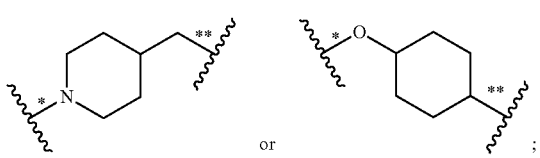 [SMILES: *CC1CCN(*)CC1 ; *OC1CCC(*)CC1]

and
$R^1$, $R^2$ and $R^3$ are each independently a hydrogen atom or a substituent; or
$R^1$ and $R^2$ are optionally bonded to each other to form, together with each adjacent carbon atom, an optionally further substituted 3- to 6-membered ring,
or a salt thereof (hereinafter sometimes to be referred to as compound (I));

[2] the compound of the above-mentioned [1], wherein
Z is a $C_{1-6}$ alkoxy group;
W is
(1) a $C_{1-10}$ alkyl group optionally substituted by 1 to 5 halogen atoms,
(2) a $C_{1-10}$ alkoxy group optionally substituted by 1 to 5 halogen atoms,
(3) a $C_{6-14}$ aryl group optionally substituted by 1 to 5 substituents selected from
  (a) a $C_{1-6}$ alkoxy group optionally substituted by 1 to 5 halogen atoms, and
  (b) a 3- to 14-membered non-aromatic heterocyclic group,
(4) a 5- to 14-membered aromatic heterocyclic group optionally substituted by 1 to 5 substituents selected from
  (a) a $C_{1-6}$ alkyl group optionally substituted by 1 to 5 halogen atoms, and
  (b) a $C_{1-6}$ alkoxy group optionally substituted by 1 to 5 halogen atoms, (5) a 3- to 14-membered non-aromatic heterocyclic group optionally substituted by 1 to 5 substituents selected from $C_{1-6}$ alkyl groups optionally substituted by 1 to 5 halogen atoms,
(6) a carbamoyl group optionally mono- or di-substituted by substituent(s) selected from
  (a) a $C_{1-6}$ alkyl group, and
  (b) a 5- to 14-membered aromatic heterocyclic group optionally substituted by 1 to 5 $C_{1-6}$ alkyl groups, or
(7) a $C_{3-10}$ cycloalkyl group optionally substituted by 1 to 5 halogen atoms;
$R^1$ is a hydrogen atom or a $C_{1-6}$ alkyl group, and $R^2$ and $R^3$ are each a hydrogen atom;
or a salt thereof;

[3] the compound of the above-mentioned [1], wherein
X is an oxygen atom or a bond;
$Y^1$ is CH or N;
$Y^2$ is N;
Z is a $C_{1-6}$ alkoxy group;
W is
(1) a $C_{1-6}$ alkyl group optionally substituted by 1 to 5 halogen atoms,
(2) a $C_{1-6}$ alkoxy group optionally substituted by 1 to 5 halogen atoms,
(3) a 3- to 14-membered non-aromatic heterocyclic group optionally substituted by 1 to 5 substituents selected from $C_{1-6}$ alkyl groups optionally substituted by 1 to 5 halogen atoms, or
(4) a $C_{3-10}$ cycloalkyl group optionally substituted by 1 to 5 halogen atoms;
L is

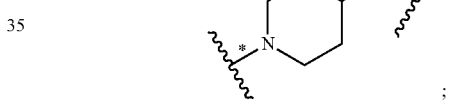

and
$R^1$, $R^2$ and $R^3$ are each a hydrogen atom;
or a salt thereof;

[4] (6-((1-(5-methoxy-2-(3,3,3-trifluoropropyl)phenyl)piperidin-4-yl)methoxy)-3,4-dihydro-2H-pyrano[2,3-c]pyridin-4-yl)acetic acid or a salt thereof;

[5] (6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetic acid or a salt thereof;

[6] (6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid or a salt thereof;

[7] (6-((1-(2-(4,4-difluorocyclohexyl)-5-methoxyphenyl)piperidin-4-yl)methoxy)-3,4-dihydro-2H-pyrano[2,3-c]pyridin-4-yl)acetic acid or a salt thereof;

[8] (6-((1-(2-methoxy-5-(3,3,3-trifluoropropyl)pyridin-4-yl)piperidin-4-yl)methoxy)-3,4-dihydro-2H-pyrano[2,3-c]pyridin-4-yl)acetic acid or a salt thereof;

[9] a medicament comprising the compound of the above-mentioned [1] or a salt thereof;

[10] the medicament of the above-mentioned [9], which is a GPR40 receptor function regulator;

[11] the medicament of the above-mentioned [9], which is a prophylactic or therapeutic agent for diabetes;

[12] a method for regulating GPR40 receptor function in a mammal, comprising administering an effective amount of the compound of the above-mentioned [1] or a salt thereof to the mammal;

[13] a method for preventing or treating obesity or diabetes in a mammal, comprising administering an effective amount of the compound of the above-mentioned [1] or a salt thereof to the mammal;

[14] use of the compound of the above-mentioned [1] or a salt thereof for the production of an agent for the prophylaxis or treatment of obesity or diabetes;

[15] the compound of the above-mentioned [1] or a salt thereof for use for the prophylaxis or treatment of obesity or diabetes;

and the like.

Effect of the Invention

Since compound (I) may have a superior GPR40 agonist activity and GLP-1 secretagogue action, may be superior in the property as a pharmaceutical product such as stability and the like, and may particularly show high solubility, low toxicity, good kinetics such as sustainability in blood and the like, it can provide a safe and useful agent for the prophylaxis or treatment of mammalian GPR40 receptor-related pathology or disease.

DETAILED DESCRIPTION OF THE INVENTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_1$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),

(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_6$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_6$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-4}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_6$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocylyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane, and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane, and cyclooctane.

In the present specification, examples of the "$C_{3-10}$ cycloalkene" include cyclopropene, cyclobutene, cyclopentene, cyclohexene, cycloheptene, and cyclooctene.

In the present specification, examples of the "heterocycle" include aromatic heterocycle and non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi- or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiine, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and
9- to 14-membered fused polycyclic the formula (preferably 2- or tricyclic) non-aromatic heterocycles such as dihydrobenzofuran, dihydrobenzoimidazole, dihydrobenzooxazole, dihydrobenzothiazole, dihydrobenzoisothiazole, dihydronaphto[2,3-b]thiophene, tetrahydroisoquinoline, tetrahydroquinoline, 4H-quinolizine, indoline, isoindoline, tetrahydrothieno[2,3-c]pyridine, tetrahydrobenzoazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring constituting atom.

In the present specification, examples of the "aromatic ring" (including "aromatic ring" in the "optionally further substituted aromatic ring") include a $C_{6-14}$ aromatic hydrocarbon ring, and aromatic heterocycle.

In the present specification, the "aromatic ring" of the "optionally further substituted aromatic ring" optionally has 1 to 5, preferably 1 to 3, substituents at substitutable position(s). When the number of the substituents is not less than 2, the respective substituents may be the same or different.

In the present specification, examples of the "optionally substituted $C_{1-6}$ alkyl group" include the "optionally substituted hydrocarbon group" wherein the hydrocarbon group is a "$C_{1-6}$ alkyl group".

In the present specification, examples of the "optionally substituted $C_{3-10}$ cycloalkyl group" include the "optionally substituted hydrocarbon group" wherein the hydrocarbon group is a "$C_{3-10}$ cycloalkyl group".

In the present specification, the "$C_{1-6}$ alkoxy group" of the "optionally substituted $C_{1-6}$ alkoxy group" optionally has 1 to 5, preferably 1 to 3, substituents, at substitutable position(s). When the number of the substituents is not less than 2, the respective substituents may be the same or different.

In the present specification, examples of the "4-6-membered nitrogen-containing saturated ring" (including the "4-6-membered nitrogen-containing saturated ring" of the "optionally further substituted 4-6-membered nitrogen-containing saturated ring") include the above-mentioned "nitrogen-containing heterocycle" which is 4- to 6-membered and saturated.

In the present specification, the "4-6-membered nitrogen-containing saturated ring" of the "optionally further substituted 4- to 6-membered nitrogen-containing saturated ring" preferably optionally has 1 to 5, preferably 1 to 3 substituents at substitutable position(s). When the number of the substituents is not less than 2, the respective substituents may be the same or different.

In the present specification, examples of the "3- to 10-membered ring" (including the "3- to 10-membered ring" of the "optionally substituted 3- to 10-membered ring") include the above-mentioned "hydrocarbon ring" and "heterocycle" which are 3- to 10-membered.

In the present specification, the "3- to 10-membered ring" of the "optionally substituted 3- to 10-membered ring" optionally has 1 to 5, preferably 1 to 3, substituents, at substitutable position(s). When the number of the substituents is not less than 2, the respective substituents may be the same or different.

In the present specification, examples of the "$C_{1-10}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, 4,4-dimethylpentyl, 5,5-dimethylhexyl and 6,6-dimethylheptyl.

In the present specification, examples of the "$C_{1-10}$ alkoxy group" include methoxy, ethoxy, propoxy, isopropoxy, butoxy, isobutoxy, sec-butoxy, tert-butoxy, pentyloxy, hexyloxy, isohexyloxy, 1,1-dimethylbutoxy, 2,2-dimethylbutoxy, 3,3-dimethylbutoxy, 2-ethylbutoxy, 4,4-dimethylpentyloxy, 5,5-dimethylhexyloxy and 6,6-dimethylheptyloxy.

The definition of each symbol in the formula (I) is described in detail in the following.

X is an oxygen atom or a bond.

$Y^1$ is CH or N.

$Y^2$ is CH or N. $Y^2$ is preferably N.

Z is an optionally substituted alkyl group, an optionally substituted alkoxy group or a halogen atom.

Examples of the substituent of the "optionally substituted alkyl group" and "optionally substituted alkoxy group" for Z include substituents selected from the "substituent" defined above. The number of the above-mentioned substituents in each of the "optionally substituted alkyl group" and "optionally substituted alkoxy group" is, for example, 1 to 5, preferably 1 to 3. When the number of the substituents is two or more, the respective substituents may be the same or different.

Examples of the "alkyl group" of the "optionally substituted alkyl group" for Z include a $C_{1-6}$ alkyl group. Examples of the "alkoxy group" of the "optionally substituted alkoxy group" for Z include a $C_{1-6}$ alkoxy group.

Z is preferably a $C_{1-6}$ alkoxy group (e.g., methoxy) or a halogen atom, more preferably a $C_{1-6}$ alkoxy group (e.g., methoxy).

In another embodiment of the present invention, Z is preferably a $C_{1-6}$ alkyl group (e.g., methyl, ethyl), a $C_{1-6}$ alkoxy group (e.g., methoxy) or a halogen atom (e.g., chlorine atom), more preferably a $C_{1-6}$ alkoxy group (e.g., methoxy).

W is an optionally substituted alkyl group, an optionally substituted alkoxy group, —$NR^{W1}R^{W2}$, an optionally substituted carbamoyl group or an optionally substituted cyclic group. $R^{W1}$ is an optionally substituted alkyl group or an acyl group. $R^{W2}$ is a hydrogen atom or a substituent.

Examples of the substituent of the "optionally substituted alkyl group", "optionally substituted alkoxy group", "optionally substituted carbamoyl group" and "optionally substituted cyclic group" for W include substituents selected from the "substituent" defined above. The number of the above-mentioned substituents in each of the "optionally substituted alkyl group", "optionally substituted alkoxy group", "optionally substituted carbamoyl group" and "optionally substituted cyclic group" is, for example, 1 to 5, preferably 1 to 3. When the number of the substituents is two or more, the respective substituents may be the same or different.

Examples of the "alkyl group" of the "optionally substituted alkyl group" for W include a $C_{1-10}$ alkyl group. Examples of the "alkoxy group" of the "optionally substituted alkoxy group" for W include a $C_{1-10}$ alkoxy group.

Examples of the "cyclic group" of the "optionally substituted cyclic group" for W include a $C_{6-14}$ aryl group, a $C_{3-10}$ cycloalkyl group, a $C_{3-10}$ cycloalkenyl group, a 5- to 14-membered aromatic heterocyclic group, a 3- to 14-membered non-aromatic heterocyclic group and the like.

Examples of the substituent of the "optionally substituted alkyl group" for $R^{W1}$ include substituents selected from the "substituent" defined above. The number of the substituents in the "optionally substituted alkyl group" is, for example, 1 to 5, preferably 1 to 3. When the number of the substituents is two or more, the respective substituents may be the same or different.

Examples of the "alkyl group" of the "optionally substituted alkyl group" for $R^{W1}$ include a $C_{1-6}$ alkyl group.

W is preferably (1) a $C_{1-10}$ alkyl group (e.g., propyl, isopropyl, butyl, 4,4-dimethylpentyl) optionally substituted by 1 to 5 halogen atoms (e.g., fluorine atom), (2) a $C_{1-10}$ alkoxy group (e.g., propoxy) optionally substituted by 1 to 5 halogen atoms (e.g., fluorine atom), (3) a $C_{6-14}$ aryl group (e.g., phenyl) optionally substituted by 1 to 5 substituents selected from (a) a $C_{1-6}$ alkoxy group (e.g., methoxy) optionally substituted by 1 to 5 halogen atoms (e.g., fluorine atom), and (b) a 3- to 14-membered non-aromatic heterocyclic group (e.g., morpholinyl), (4) a 5- to 14-membered aromatic heterocyclic group (e.g., pyridyl, pyrimidinyl) optionally substituted by 1 to 5 substituents selected from (a) a $C_{1-6}$ alkyl group (e.g., methyl) optionally substituted by 1 to 5 halogen atoms (e.g., fluorine atom), and (b) a $C_{1-6}$ alkoxy group (e.g., ethoxy) optionally substituted by 1 to 5 halogen atoms (e.g., fluorine atom), (5) a 3- to 14-membered non-aromatic heterocyclic group (e.g., piperidinyl) optionally substituted by 1 to 5 substituents selected from a $C_{1-6}$ alkyl group (e.g., ethyl, propyl) optionally substituted by 1 to 5 halogen atoms (e.g., fluorine atom), or (6) a carbamoyl group optionally mono- or di-substituted by substituent(s) selected from (a) a $C_{1-6}$ alkyl group (e.g., neopentyl), and (b) a 5- to 14-membered aromatic heterocyclic group (e.g., pyridyl, pyrimidinyl) optionally substituted by 1 to 5 $C_{1-6}$ alkyl groups (e.g., methyl).

W is more preferably (1) a $C_{1-10}$ alkyl group (e.g., propyl) optionally substituted by 1 to 5 halogen atoms (e.g., fluorine atom), (2) a $C_{1-10}$ alkoxy group (e.g., propoxy) optionally substituted by 1 to 5 halogen atoms (e.g., fluorine atom) or (3) a 3- to 14-membered non-aromatic heterocyclic group (e.g., piperidinyl) optionally substituted by 1 to 5 substituents selected from a $C_{1-6}$ alkyl group (e.g., ethyl) optionally substituted by 1 to 5 halogen atoms (e.g., fluorine atom).

In another embodiment of the present invention, W is preferably (1) a $C_{1-10}$ alkyl group (e.g., methyl, propyl, isopropyl, butyl, 4,4-dimethylpentyl) optionally substituted by 1 to 5 substituents selected from (a) a halogen atom (e.g., fluorine atom), and (b) a 3- to 14-membered non-aromatic heterocyclic group (e.g., pyrrolidinyl) optionally substituted by 1 to 5 halogen atoms (e.g., fluorine atom), (2) a $C_{1-10}$ alkoxy group (e.g., propoxy) optionally substituted by 1 to 5 halogen atoms (e.g., fluorine atom), (3) a $C_{6-14}$ aryl group (e.g., phenyl) optionally substituted by 1 to 5 substituents selected from (a) a $C_{1-6}$ alkoxy group (e.g., methoxy) optionally substituted by 1 to 5 halogen atoms (e.g., fluorine atom), and (b) a 3- to 14-membered non-aromatic heterocyclic group (e.g., morpholinyl), (4) a 5- to 14-membered aromatic heterocyclic group (e.g., pyridyl, pyrimidinyl) optionally substituted by 1 to 5 substituents selected from (a) a $C_{1-6}$ alkyl group (e.g., methyl) optionally substituted by 1 to 5 halogen atoms (e.g., fluorine atom), and (b) a $C_{1-6}$ alkoxy group (e.g., ethoxy) optionally substituted by 1 to 5 halogen atoms (e.g., fluorine atom), (5) a 3- to 14-membered non-aromatic heterocyclic group (e.g., piperidinyl, tetrahydropyranyl) optionally substituted by 1 to substituents selected from (a) a $C_{1-6}$ alkyl group (e.g., methyl, ethyl, propyl) optionally substituted by 1 to 5 halogen atoms (e.g., fluorine atom), and (b) a $C_{1-6}$ alkoxy group (e.g., methoxy), (6) a carbamoyl group optionally mono- or di-substituted by substituent(s) selected from (a) a $C_{1-6}$ alkyl group (e.g., neopentyl), (b) a 5- to 14-membered aromatic heterocyclic group (e.g., pyridyl, pyrimidinyl) optionally substituted by 1 to 5 $C_{1-6}$ alkyl groups (e.g., methyl), or (7) a $C_{3-10}$ cycloalkyl group (e.g., cyclohexyl) optionally substituted by 1 to 5 halogen atoms (e.g., fluorine atom).

In another embodiment of the present invention, W is more preferably (1) a $C_{1-6}$ alkyl group (e.g., propyl) optionally substituted by 1 to 5 halogen atoms (e.g., fluorine atom), (2) a $C_{1-6}$ alkoxy group (e.g., propoxy) optionally substituted by 1 to 5 halogen atoms (e.g., fluorine atom), (3) a 3- to 14-membered non-aromatic heterocyclic group (e.g., piperidinyl) optionally substituted by 1 to 5 substituents selected from a $C_{1-6}$ alkyl group (e.g., ethyl) optionally substituted by 1 to 5 halogen atoms (e.g., fluorine atom), or (4) a $C_{3-10}$ cycloalkyl group (e.g., cyclohexyl) optionally substituted by 1 to 5 halogen atoms (e.g., fluorine atom).

L is

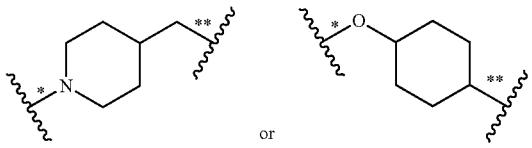

As used herein, * shows the binding site to a carbon atom of the aromatic ring and ** shows the binding site to O.

$R^1$, $R^2$ and $R^3$ are each independently a hydrogen atom or a substituent. Alternatively, $R^1$ and $R^2$ are optionally bonded to each other to form, together with each adjacent carbon atom, an optionally further substituted 3- to 6-membered ring.

Examples of the substituent of the "optionally further substituted 3- to 6-membered ring" formed by $R^1$ and $R^2$ include substituents selected from the "substituent" defined above. The number of the substituents of the "optionally further substituted 3- to 6-membered ring" is, for example, 1 to 5, preferably 1 to 3. When the number of the substituents is two or more, the respective substituents may be the same or different.

Examples of the "3- to 6-membered ring" of the "optionally further substituted 3- to 6-membered ring" formed by $R^1$ and $R^2$ include $C_{3-6}$ cycloalkane (e.g., 3- to 6-membered ones among "$C_{3-10}$ cycloalkane" exemplified above), $C_{3-6}$ cycloalkene (e.g., 3- to 6-membered ones among "$C_{3-10}$ cycloalkene" exemplified above) and 3- to 6-membered monocyclic non-aromatic heterocycle (e.g., 3- to 6-membered ones among "3- to 8-membered monocyclic non-aromatic heterocycle" exemplified above).

Preferably, $R^1$, $R^2$ and $R^3$ are each independently a hydrogen atom or a $C_{1-6}$ alkyl group (e.g., methyl). More preferably, $R^1$ is a hydrogen atom or a $C_{1-6}$ alkyl group (e.g., methyl), and $R^2$ and $R^3$ are each a hydrogen atom. Further preferably, $R^1$, $R^2$ and $R^3$ are each a hydrogen atom.

Preferable examples of compound (I) include the following compounds.

[Compound I-1]
  Compound (I) wherein
  X is an oxygen atom or a bond;
  $Y^1$ and $Y^2$ are each independently CH or N;
  Z is a $C_{1-6}$ alkoxy group (e.g., methoxy);
  W is
  (1) a $C_{1-10}$ alkyl group (e.g., propyl, isopropyl, butyl, 4,4-dimethylpentyl) optionally substituted by 1 to 5 halogen atoms (e.g., fluorine atom),
  (2) a $C_{1-10}$ alkoxy group (e.g., propoxy) optionally substituted by 1 to 5 halogen atoms (e.g., fluorine atom),
  (3) a $C_{6-14}$ aryl group (e.g., phenyl) optionally substituted by 1 to 5 substituents selected from
    (a) a $C_{1-6}$ alkoxy group (e.g., methoxy) optionally substituted by 1 to 5 halogen atoms (e.g., fluorine atom), and
    (b) a 3- to 14-membered non-aromatic heterocyclic group (e.g., morpholinyl),
  (4) a 5- to 14-membered aromatic heterocyclic group (e.g., pyridyl, pyrimidinyl) optionally substituted by 1 to 5 substituents selected from
    (a) a $C_{1-6}$ alkyl group (e.g., methyl) optionally substituted by 1 to 5 halogen atoms (e.g., fluorine atom), and
    (b) a $C_{1-6}$ alkoxy group (e.g., ethoxy) optionally substituted by 1 to 5 halogen atoms (e.g., fluorine atom),
  (5) a 3- to 14-membered non-aromatic heterocyclic group (e.g., piperidinyl) optionally substituted by 1 to 5 substituents selected from a $C_{1-6}$ alkyl group (e.g., ethyl, propyl) optionally substituted by 1 to 5 halogen atoms (e.g., fluorine atom), or
  (6) a carbamoyl group optionally mono- or di-substituted by substituent(s) selected from
    (a) a $C_{1-6}$ alkyl group (e.g., neopentyl), and
    (b) a 5- to 14-membered aromatic heterocyclic group (e.g., pyridyl, pyrimidinyl) optionally substituted by 1 to 5 $C_{1-6}$ alkyl groups (e.g., methyl);

L is

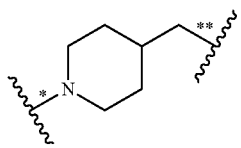 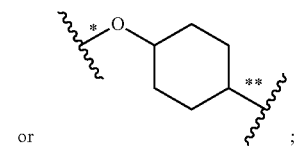
or
;

$R^1$ is a hydrogen atom or a $C_{1-6}$ alkyl group (e.g., methyl), and $R^2$ and $R^3$ is a hydrogen atom.

[Compound I-2]
  Compound (I) wherein
  X is an oxygen atom or a bond;
  $Y^1$ is CH;
  $Y^2$ is N;
  Z is a $C_{1-6}$ alkoxy group (e.g., methoxy);
  W is
  (1) a 5- to 14-membered aromatic heterocyclic group (e.g., pyrimidinyl) optionally substituted by 1 to 5 substituents selected from a $C_{1-6}$ alkoxy group (e.g., ethoxy) optionally substituted by 1 to 5 halogen atoms (e.g., fluorine atom), or
  (2) a 3- to 14-membered non-aromatic heterocyclic group (e.g., piperidinyl) optionally substituted by 1 to 5 substituents selected from a $C_{1-6}$ alkyl group (e.g., ethyl, propyl) optionally substituted by 1 to 5 halogen atoms (e.g., fluorine atom);
  L is

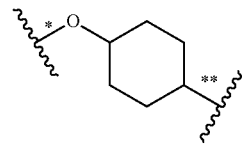
;

and
$R^1$, $R^2$ and $R^3$ are each a hydrogen atom.

[Compound I-3]
  Compound (I) wherein
  X is an oxygen atom or a bond;
  $Y^1$ and $Y^2$ are each independently CH or N;
  Z is a $C_{1-6}$ alkoxy group (e.g., methoxy);
  W is
  (1) a $C_{1-10}$ alkyl group (e.g., propyl, isopropyl, butyl, 4,4-dimethylpentyl) optionally substituted by 1 to 5 halogen atoms (e.g., fluorine atom),
  (2) a $C_{1-10}$ alkoxy group (e.g., propoxy) optionally substituted by 1 to 5 halogen atoms (e.g., fluorine atom),
  (3) a $C_{6-14}$ aryl group (e.g., phenyl) optionally substituted by 1 to 5 substituents selected from
    (a) a $C_{1-6}$ alkoxy group (e.g., methoxy) optionally substituted by 1 to 5 halogen atoms (e.g., fluorine atom), and
    (b) a 3- to 14-membered non-aromatic heterocyclic group (e.g., morpholinyl),
  (4) a 5- to 14-membered aromatic heterocyclic group (e.g., pyridyl) optionally substituted by 1 to 5 substituents selected from a $C_{1-6}$ alkyl group (e.g., methyl) optionally substituted by 1 to 5 halogen atoms (e.g., fluorine atom),
  (5) a 3- to 14-membered non-aromatic heterocyclic group (e.g., piperidinyl) optionally substituted by 1 to 5 substituents selected from a $C_{1-6}$ alkyl group (e.g., ethyl, propyl) optionally substituted by 1 to 5 halogen atoms (e.g., fluorine atom), or (6) a carbamoyl group optionally mono- or di-substituted by substituent(s) selected from
(a) a $C_{1-6}$ alkyl group (e.g., neopentyl), and
(b) a 5- to 14-membered aromatic heterocyclic group (e.g., pyridyl, pyrimidinyl) optionally substituted by 1 to 5 $C_{1-6}$ alkyl groups (e.g., methyl);
L is

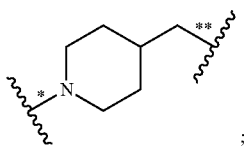 [SMILES: *CC1CCN(*)CC1]

and
$R^1$ is a hydrogen atom or a $C_{1-6}$ alkyl group (e.g., methyl) and $R^2$ and $R^3$ are each a hydrogen atom.

[Compound I-4]
Compound (I) wherein
X is an oxygen atom or a bond;
$Y^1$ is CH or N;
$Y^2$ is N;
Z is a $C_{1-6}$ alkoxy group (e.g., methoxy);
W is
(1) a $C_{1-6}$ alkyl group (e.g., propyl) optionally substituted by 1 to 5 halogen atoms (e.g., fluorine atom),
(2) a $C_{1-6}$ alkoxy group (e.g., propoxy) optionally substituted by 1 to 5 halogen atoms (e.g., fluorine atom), or
(3) a 3- to 14-membered non-aromatic heterocyclic group (e.g., piperidinyl) optionally substituted by 1 to 5 substituents selected from a $C_{1-6}$ alkyl group (e.g., ethyl) optionally substituted by 1 to 5 halogen atoms (e.g., fluorine atom);
L is

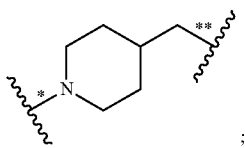 [SMILES: *CC1CCN(*)CC1]

and
$R^1$, $R^2$ and $R^3$ are each a hydrogen atom.

[Compound I-5]
Compounds (I) of Examples 1-48.

[Compound I-6]
Compound (I) selected from
(6-((1-(5-methoxy-2-(3,3,3-trifluoropropyl)phenyl)piperidin-4-yl)methoxy)-3,4-dihydro-2H-pyrano[2,3-c]pyridin-4-yl)acetic acid (compound of Example 1);
(6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetic acid (compound of Example 2);
(3-((1-(2-methoxy-5-(2,2,3,3,3-pentafluoropropoxy)pyridin-4-yl)piperidin-4-yl)methoxy)-6,7-dihydro-5H-cyclopenta[c]pyridin-5-yl)acetic acid (compound of Example 3);
(3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetic acid (compound of Example 4);
(6-((1-(2-methoxy-5-(1-(2,2,2-trifluoroethyl)piperidin-4-yl)pyridin-4-yl)piperidin-4-yl)methoxy)-3,4-dihydro-2H-pyrano[2,3-c]pyridin-4-yl)acetic acid (compound of Example 5);

(6-((1-(2-methoxy-5-(1-(2,2,2-trifluoroethyl)piperidin-4-yl)pyridin-4-yl)piperidin-4-yl)methoxy)-3,4-dihydro-2H-pyrano[2,3-c]pyridin-4-yl)acetic acid (Optical Isomer) (compound of Example 6);
(6-((1-(2-methoxy-5-(1-(2,2,2-trifluoroethyl)piperidin-4-yl)pyridin-4-yl)piperidin-4-yl)methoxy)-3,4-dihydro-2H-pyrano[2,3-c]pyridin-4-yl)acetic acid (Optical Isomer) (compound of Example 7);
(6-((1-(5-methoxy-2-(3,3,3-trifluoropropyl)phenyl)piperidin-4-yl)methoxy)-3,4-dihydro-2H-pyrano[2,3-c]pyridin-4-yl)acetic acid (Optical Isomer) (compound of Example 8);
(6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (Optical Isomer) (compound of Example 9);
(3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetic acid (Optical Isomer) (compound of Example 10);
(6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetic acid (optical isomer) (compound of Example 11);
(6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetic acid (optical isomer) (compound of Example 17);
(6-((1-(5-methoxy-2-(3,3,3-trifluoropropyl)phenyl)piperidin-4-yl)methoxy)-3,4-dihydro-2H-pyrano[2,3-c]pyridin-4-yl)acetic acid (Optical Isomer) (compound of Example 18);
(6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (Optical Isomer) (compound of Example 28);
(3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetic acid (Optical Isomer) (compound of Example 29); and
(6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (compound of Example 36).

[Compound I-7]
Compound (I) wherein
X is an oxygen atom or a bond;
$Y^1$ and $Y^2$ are each independently CH or N;
Z is a $C_{1-6}$ alkyl group (e.g., methyl, ethyl), $C_{1-6}$ alkoxy group (e.g., methoxy) or a halogen atom (e.g., chlorine atom);
W is
(1) a $C_{1-10}$ alkyl group (e.g., methyl, propyl, isopropyl, butyl, 4,4-dimethylpentyl) optionally substituted by 1 to 5 substituents selected from
(a) a halogen atom (e.g., fluorine atom), and
(b) a 3- to 14-membered non-aromatic heterocyclic group (e.g., pyrrolidinyl) optionally substituted by 1 to 5 halogen atoms (e.g., fluorine atom),
(2) a $C_{1-10}$ alkoxy group (e.g., propoxy) optionally substituted by 1 to 5 halogen atoms (e.g., fluorine atom),
(3) a $C_{6-14}$ aryl group (e.g., phenyl) optionally substituted by 1 to 5 substituents selected from
(a) a $C_{1-6}$ alkoxy group (e.g., methoxy) optionally substituted by 1 to 5 halogen atoms (e.g., fluorine atom), and
(b) a 3- to 14-membered non-aromatic heterocyclic group (e.g., morpholinyl), (4) a 5- to 14-membered aromatic heterocyclic group (e.g., pyridyl, pyrimidinyl) optionally substituted by 1 to 5 substituents selected from
  (a) a $C_{1-6}$ alkyl group (e.g., methyl) optionally substituted by 1 to 5 halogen atoms (e.g., fluorine atom), and
  (b) a $C_{1-6}$ alkoxy group (e.g., ethoxy) optionally substituted by 1 to 5 halogen atoms (e.g., fluorine atom),
(5) a 3- to 14-membered non-aromatic heterocyclic group (e.g., piperidinyl, tetrahydropyranyl) optionally substituted by 1 to substituents selected from
  (a) a $C_{1-6}$ alkyl group (e.g., methyl, ethyl, propyl) optionally substituted by 1 to 5 halogen atoms (e.g., fluorine atom), and
  (b) a $C_{1-6}$ alkoxy group (e.g., methoxy),
(6) a carbamoyl group optionally mono- or di-substituted by substituent(s) selected from
  (a) a $C_{1-6}$ alkyl group (e.g., neopentyl), and
  (b) a 5- to 14-membered aromatic heterocyclic group (e.g., pyridyl, pyrimidinyl) optionally substituted by 1 to 5 $C_{1-6}$ alkyl groups (e.g., methyl), or
(7) a $C_{3-10}$ cycloalkyl group (e.g., cyclohexyl) optionally substituted by 1 to 5 halogen atoms (e.g., fluorine atom);
L is

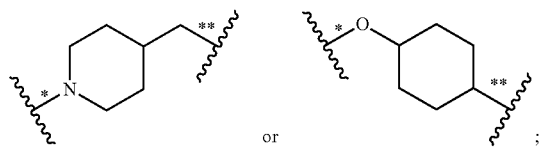 [SMILES: *CC1CCN(*)CC1 ; *OC1CCC(*)CC1]

or and
$R^1$ is a hydrogen atom or a $C_{1-6}$ alkyl group (e.g., methyl), and $R^2$ and $R^3$ are each a hydrogen atom.
[Compound I-8]
Compound (I) wherein
X is an oxygen atom or a bond;
$Y^1$ and $Y^2$ are each independently CH or N;
Z is a $C_{1-6}$ alkyl group (e.g., methyl, ethyl), a $C_{1-6}$ alkoxy group (e.g., methoxy) or a halogen atom (e.g., chlorine atom);
W is
(1) a $C_{1-10}$ alkyl group (e.g., methyl, propyl, isopropyl, butyl, 4,4-dimethylpentyl) optionally substituted by 1 to 5 substituents selected from
  (a) a halogen atom (e.g., fluorine atom), and
  (b) a 3- to 14-membered non-aromatic heterocyclic group (e.g., pyrrolidinyl) optionally substituted by 1 to 5 halogen atoms (e.g., fluorine atom),
(2) a $C_{1-10}$ alkoxy group (e.g., propoxy) optionally substituted by 1 to 5 halogen atoms (e.g., fluorine atom),
(3) a $C_{6-14}$ aryl group (e.g., phenyl) optionally substituted by 1 to 5 substituents selected from
  (a) a $C_{1-6}$ alkoxy group (e.g., methoxy) optionally substituted by 1 to 5 halogen atoms (e.g., fluorine atom), and
  (b) a 3- to 14-membered non-aromatic heterocyclic group (e.g., morpholinyl),
(4) a 5- to 14-membered aromatic heterocyclic group (e.g., pyridyl) optionally substituted by 1 to 5 substituents selected from a $C_{1-6}$ alkyl group (e.g., methyl) optionally substituted by 1 to 5 halogen atoms (e.g., fluorine atom),
(5) a 3- to 14-membered non-aromatic heterocyclic group (e.g., piperidinyl, tetrahydropyranyl) optionally substituted by 1 to substituents selected from
  (a) a $C_{1-6}$ alkyl group (e.g., methyl, ethyl, propyl) optionally substituted by 1 to 5 halogen atoms (e.g., fluorine atom), and
  (b) a $C_{1-6}$ alkoxy group (e.g., methoxy),
(6) a carbamoyl group optionally mono- or di-substituted by substituent(s) selected from
  (a) a $C_{1-6}$ alkyl group (e.g., neopentyl), and
  (b) a 5- to 14-membered aromatic heterocyclic group (e.g., pyridyl, pyrimidinyl) optionally substituted by 1 to 5 $C_{1-6}$ alkyl groups (e.g., methyl), or
(7) a $C_{3-10}$ cycloalkyl group (e.g., cyclohexyl) optionally substituted by 1 to 5 halogen atoms (e.g., fluorine atom);
L is

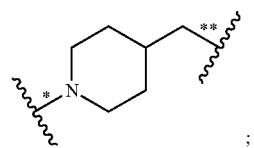 [SMILES: *CC1CCN(*)CC1]

and
$R^1$ is a hydrogen atom or a $C_{1-6}$ alkyl group (e.g., methyl) and $R^2$ and $R^3$ are each a hydrogen atom.
[Compound I-9]
Compound (I) wherein
X is an oxygen atom or a bond;
$Y^1$ is CH or N;
$Y^2$ is N;
Z is a $C_{1-6}$ alkoxy group (e.g., methoxy);
W is
(1) a $C_{1-6}$ alkyl group (e.g., propyl) optionally substituted by 1 to 5 halogen atoms (e.g., fluorine atom),
(2) a $C_{1-6}$ alkoxy group (e.g., propoxy) optionally substituted by 1 to 5 halogen atoms (e.g., fluorine atom),
(3) a 3- to 14-membered non-aromatic heterocyclic group (e.g., piperidinyl) optionally substituted by 1 to 5 substituents selected from a $C_{1-6}$ alkyl group (e.g., ethyl) optionally substituted by 1 to 5 halogen atoms (e.g., fluorine atom), or
(4) a $C_{3-10}$ cycloalkyl group (e.g., cyclohexyl) optionally substituted by 1 to 5 halogen atoms (e.g., fluorine atom);
L is

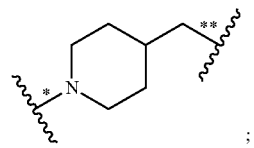 [SMILES: *CC1CCN(*)CC1]

and
$R^1$, $R^2$ and $R^3$ are each a hydrogen atom.
[Compound I-10]
Compounds (I) of Examples 1-59.
[Compound I-11]
Compound (I) selected from
(6-((1-(5-methoxy-2-(3,3,3-trifluoropropyl)phenyl)piperidin-4-yl)methoxy)-3,4-dihydro-2H-pyrano[2,3-c]pyridin-4-yl)acetic acid (compound of Example 1);
(6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetic acid (compound of Example 2);
(3-((1-(2-methoxy-5-(2,2,3,3,3-pentafluoropropoxy)pyridin-4-yl)piperidin-4-yl)methoxy)-6,7-dihydro-5H-cyclopenta[c]pyridin-5-yl)acetic acid (compound of Example 3);

(3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetic acid (compound of Example 4);

(6-((1-(2-methoxy-5-(1-(2,2,2-trifluoroethyl)pyridin-4-yl)piperidin-4-yl)methoxy)-3,4-dihydro-2H-pyrano[2,3-c]pyridin-4-yl)acetic acid (compound of Example 5);

(6-((1-(2-methoxy-5-(1-(2,2,2-trifluoroethyl)pyridin-4-yl)piperidin-4-yl)methoxy)-3,4-dihydro-2H-pyrano[2,3-c]pyridin-4-yl)acetic acid (Optical Isomer) (compound of Example 6);

(6-((1-(2-methoxy-5-(1-(2,2,2-trifluoroethyl)pyridin-4-yl)piperidin-4-yl)methoxy)-3,4-dihydro-2H-pyrano[2,3-c]pyridin-4-yl)acetic acid (Optical Isomer) (compound of Example 7);

(6-((1-(5-methoxy-2-(3,3,3-trifluoropropyl)phenyl)piperidin-4-yl)methoxy)-3,4-dihydro-2H-pyrano[2,3-c]pyridin-4-yl)acetic acid (Optical Isomer) (compound of Example 8);

(6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (Optical Isomer) (compound of Example 9);

(3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetic acid (Optical Isomer) (compound of Example 10);

(6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetic acid (optical isomer) (compound of Example 11);

(6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetic acid (optical isomer) (compound of Example 17);

(6-((1-(5-methoxy-2-(3,3,3-trifluoropropyl)phenyl)piperidin-4-yl)methoxy)-3,4-dihydro-2H-pyrano[2,3-c]pyridin-4-yl)acetic acid (Optical Isomer) (compound of Example 18);

(6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (Optical Isomer) (compound of Example 28);

(3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetic acid (Optical Isomer) (compound of Example 29);

(6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (compound of Example 36);

(6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (Optical Isomer) (compound of Example 49);

(6-((1-(2-(4,4-difluorocyclohexyl)-5-methoxyphenyl)piperidin-4-yl)methoxy)-3,4-dihydro-2H-pyrano[2,3-c]pyridin-4-yl)acetic acid (Optical Isomer) (compound of Example 50); and (6-((1-(2-methoxy-5-(3,3,3-trifluoropropyl)pyridin-4-yl)piperidin-4-yl)methoxy)-3,4-dihydro-2H-pyrano[2,3-c]pyridin-4-yl)acetic acid (Optical Isomer) (compound of Example 52).

Examples of salts of compounds represented by the formula (I) include metal salt, ammonium salt, salt with organic base, salt with inorganic acid, salt with organic acid, salt with basic or acidic amino acid and the like.

Preferable examples of the metal salt include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Preferable examples of the salt with inorganic acid include salt with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like, and preferable examples of the salt with acidic amino acid include salts with aspartic acid, glutamic acid and the like.

Among the above-mentioned salts, a pharmaceutically acceptable salt is preferable.

Compound (I) may be a prodrug.

A prodrug of compound (I) means a compound which is converted to compound (I) with a reaction due to an enzyme, an gastric acid, etc. under the physiological condition in the living body, that is, a compound which is converted to compound (I) by oxidation, reduction, hydrolysis, etc. due to an enzyme; a compound which is converted to compound (I) by hydrolysis etc. due to gastric acid, etc.

Examples of the prodrug of compound (I) include a compound obtained by subjecting amino in compound (I) to an acylation, alkylation or phosphorylation (e.g., a compound obtained by subjecting amino in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting hydroxy in compound (I) to an acylation, alkylation, phosphorylation or boration (e.g., a compound obtained by subjecting hydroxy in compound (I) to an acetylation, palmitoylation, propanoylation, pivaloylation, succinylation, fumarylation, alanylation or dimethylaminomethylcarbonylation); a compound obtained by subjecting carboxy in compound (I) to an esterification or amidation (e.g., a compound obtained by subjecting carboxy in compound (I) to a $C_6$ alkyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methyl amidation etc.) and the like. Among these, compound (I) wherein carboxy is esterified by $C_{1-6}$ alkyl such as methyl, ethyl, tert-butyl and the like is preferably used. These compounds can be produced from compound (I) according to a method known per se.

A prodrug for compound (I) may also be one which is converted to compound (I) under a physiological condition, such as those described in IYAKUHIN no KAIHATSU, Development of Pharmaceuticals, Vol. 7, Design of Molecules, p. 163-198, Published by HIROKAWA SHOTEN, 1990.

In the present specification, a prodrug may be in the form of a salt. Examples of the salt include those exemplified as the salt of the compound represented by the aforementioned formula (I).

The production method of compound (I) is explained below.

The starting materials and reagents used and the compounds obtained in each step of the following production methods may form each salt. Examples of such salt include those similar to the salts of the aforementioned compound (I) and the like.

When the compound obtained in each step is a free compound, it can be converted to a desired salt by a method known per se. Conversely, when the compound obtained in each step is a salt, it can be converted to a free form or other desired kind of salt by a method known per se.

The compound obtained in each step can also be used for the next reaction in the form of the reaction mixture or after obtaining as a crude product. Alternatively, the compound obtained in each step can be isolated and/or purified from the reaction mixture by a separation means such as concentration, crystallization, recrystallization, distillation, solvent extraction, fractionation, chromatography and the like according to conventional methods.

When the starting materials and reagent compounds in each step are commercially available, such commercially available products can be directly used.

In the reaction of each step, the reaction time may vary depending on the reagent and the solvent to be used. Unless particularly described, it is generally 1 min-48 hr, preferably 10 min-8 hr.

In the reaction of each step, the reaction temperature may vary depending on the reagent and solvent to be used. Unless particularly described, it is generally −78° C. to 300° C., preferably −78° C. to 150° C.

In the reaction of each step, the pressure may vary depending on the reagent and solvent to be used. Unless particularly described, it is generally 1 atm-20 atm, preferably 1 atm-3 atm.

In the reaction of each step, for example, Microwave synthesis apparatus such as Initiator manufactured by Biotage and the like may be used. The reaction temperature may vary depending on the reagent and solvent to be used. Unless particularly described, it is generally room temperature to 300° C., preferably 50° C. to 250° C. While the reaction time varies depending on the reagent and solvent to be used, unless particularly described, it is generally 1 min-48 hr, preferably 1 min-8 hr.

In the reaction of each step, unless particularly described, a reagent is used in 0.5 equivalents-20 equivalents, preferably 0.8 equivalents-5 equivalents, relative to the substrate. When a reagent is used as a catalyst, the reagent is used in 0.001 equivalent-1 equivalent, preferably 0.01 equivalent-0.2 equivalent, relative to the substrate. When a reagent also acts as a reaction solvent, the reagent is used in a solvent amount.

In the reaction of each step, unless particularly described, the reaction is performed without solvent, or by dissolving or suspending in a suitable solvent. Specific examples of the solvent include the solvents described in the Examples and the following.

alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like;
water.

Two or more kinds of the above-mentioned solvents may be mixed at an appropriate ratio and used.

When a base is used in the reaction of each step, for example, the bases shown below or the bases described in the Examples are used.

inorganic bases: sodium hydroxide, magnesium hydroxide and the like;
basic salts: sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acidic catalyst is used in the reaction of each step, for example, the acids and acidic catalysts shown below or the acids and acidic catalysts described in the Examples are used.

inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminum chloride, anhydrous zinc chloride, anhydrous iron chloride and the like.

The reaction of each step is, unless otherwise specified, performed by a method known per se, for example, the methods described in the Fifth Series of Experimental Chemistry, vol. 13-vol. 19 (The Chemical Society of Japan ed.); Experimental Chemistry, vol. 14-vol. 15 (The Chemical Society of Japan ed.); Fine Organic Chemistry, rev. 2nd edition (L. F. Tietze, Th. Eicher, NANKODO); rev. Organic Name Reaction (Hideo Togo, Kodansha); ORGANIC SYNTHESES Collective Volume I-VII (John Wiley & Sons Inc); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (Kiyoshi Tomioka, supervisor of translation, KAGAKUDOJIN); Comprehensive Organic Transformations (VCH Publishers Inc.) 1989 and the like, or the methods described in the Examples.

When reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney-nickel; Raney cobalt; hydrogen; formic acid and the like. When carbon-carbon double bond or triple bond is reduced, a method using a catalyst such as palladium-carbon, Lindlar catalyst and the like is available.

When oxidation reaction is performed in each step, examples of the oxidant to be used include peracids such as m-chloroperbenzoic acid (MCPBA), hydrogen peroxide, t-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents having manganese such as manganese dioxide, potassium permanganate and the like; leads such as lead tetraacetate and the like; reagents having chrome such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetraoxide; selenium dioxide; 2,3-dichloro-5,6-dicyano-1,4-benzoquinone (DDQ) and the like.

When radical cyclization reaction is performed in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is performed in each step, examples of the Wittig reagent to be used include alkylidenephosphoranes and the like. Alkylidenephosphoranes can be prepared by a method known per se, for example, by reacting a phosphonium salt and a strong base.

When Horner-Emmons reaction is performed in each step, examples of the reagent to be used include phosphonoacetic acid esters such as methyl dimethylphosphonoacetate, ethyl diethylphosphonoacetate and the like; bases such as alkali metal hydrides, organic lithiums and the like.

When Friedel-Crafts reaction is performed in each step, examples of the reagent to be used include Lewis acid, acid chloride or alkylating agent (e.g., alkyl halides, alcohol, olefins and the like). Alternatively, organic acid or inorganic acid can also be used instead of the Lewis acid, and acid anhydrides such as acetic anhydride and the like can also be used instead of acid chloride.

When aromatic nucleophilic substitution reaction is performed in each step, the reagent includes nucleophilic agent (e.g., amines, imidazole and the like) and base (e.g., basic salts, organic bases and the like).

When nucleophilic addition reaction by carbanion, nucleophilic 1,4-addition reaction by carbanion (Michael addition reaction), or nucleophilic substitution reaction by carbanion is performed in each step, examples of the base to be used for developing carbanion include organic lithium, metal alkoxide, inorganic base, organic base and the like.

When Grignard reaction is performed in each step, examples of the Grignard reagent include arylmagnesium halides such as phenylmagnesium bromide and the like; and alkylmagnesium halides such as methylmagnesium bromide and the like. The Grignard reagent can be prepared by a method known per se, for example, by reacting alkyl halide or aryl halide with metal magnesium using ether or tetrahydrofuran as a solvent.

When Knoevenagel condensation reaction is performed in each step, the reagent includes an active methylene compound (e.g., malonic acid, diethyl malonate, malononitrile and the like) located between two electron-withdrawing groups and a base (e.g., organic bases, metal alkoxides, inorganic bases).

When Vilsmeier-Haack reaction is performed in each step, the reagent includes phosphoryl chloride and amide derivative (e.g., N,N-dimethylformamide and the like).

When azidation reaction of alcohol, alkyl halide, sulfonic acid ester is performed in each step, examples of the azidation agent to be used include diphenylphosphoryl azide (DPPA), trimethylsilylazide, sodium azide and the like. For example, when alcohols is azidated, a method using diphenylphosphoryl azide and 1,8-diazabicyclo[5,4,0]undec-7-ene (DBU), a method using trimethylsilylazide and Lewis acid and the like are used.

When reductive amination reaction is performed in each step, examples of the reducing agent to be used include sodium triacetoxyborohydride, sodium cyanoborohydride, hydrogen, formic acid and the like. When the substrate is an amine compound, the carbonyl compound to be used is para-formaldehyde, aldehydes such as acetaldehyde and the like, or ketones such as cyclohexanone and the like. When the substrate is a carbonyl compound, the amine to be used is ammonia, primary amine such as methylamine and the like; secondary amine such as dimethylamine and the like, or the like.

When Mitsunobu reaction is performed in each step, examples of the reagent include azodicarboxylates (e.g., diethyl azodicarboxylate (DEAD), diisopropyl azodicarboxylate (DIAD) and the like) and triphenylphosphine.

When esterification reaction, amidation reaction, or ureation reaction is performed in each step, examples of the reagent to be used include halogenated acyl forms such as acid chloride, acid bromide and the like; activated carboxylic acids such as acid anhydride, active ester form, sulfuric acid ester form and the like. As an activator of carboxylic acid, carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; or combination thereof and the like can be mentioned. When a carbodiimide condensing agent is used, additives such as 1-hydroxybenzotriazole (HOBt), N-hydroxysuccinimide (HOSu), dimethylaminopyridine (DMAP) and the like may be further added to the reaction.

When coupling reaction is performed in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, palladium(II) acetate and the like; nickel compounds such as tetrakis(triphenylphosphine)nickel (0) and the like; rhodium compounds such as tris(triphenylphosphine)rhodium(III) chloride and the like; cobalt compound; copper compounds such as copper oxide, copper(I) iodide and the like; platinum compound and the like. A base may be further added to the reaction, and examples of such base include inorganic bases, basic salts and the like.

When thiocarbonylation reaction is performed in each step, representative example of the thiocarbonylating agent is diphosphorus pentasulfide. Besides diphosphorus pentasulfide, a reagent having a 1,3,2,4-dithiadiphosphetane-2,4-disulfide structure such as 2,4-bis(4-methoxyphenyl-1,3,2,4-dithiadiphosphetane-2,4-disulfide (Lowesson's reagent) and the like may also be used.

When Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. The reaction can be accelerated by adding heat, light, a radical initiator such as benzoyl peroxide, azobisisobutyronitrile and the like to the reaction.

When halogenation reaction of the hydroxy group is performed in each step, examples of the halogenating agent to be used include acid halide of hydrohalic acid and inorganic acid, specifically, hydrochloric acid, thionyl chloride, phosphorus oxychloride and the like for chlorination, and 48% hydrobromic acid and the like for bromination. In addition, a method of obtaining an alkyl halide form from alcohol by reacting triphenylphosphine with carbon tetrachloride or carbon tetrabromide and the like may also be used. Alternatively, a method of synthesizing an alkyl halide form by two-step reactions including converting alcohol to sulfonic acid ester and reacting same with lithium bromide, lithium chloride or sodium iodide may also be used.

When Arbuzov reaction is performed in each step, examples of the reagent to be used include alkyl halides such as ethyl bromoacetate and the like; phosphites such as triethylphosphite, tri(isopropyl)phosphite and the like.

When sulfonation reaction is performed in each step, examples of the sulfonating agent to be used include methanesulfonyl chloride, p-toluenesulfonyl chloride, methanesulfonic anhydride, p-toluenesulfonic anhydride and the like.

When hydrolysis reaction is performed in each step, examples of the reagent include acid or base. When acid hydrolysis of t-butyl ester is performed, formic acid, triethylsilane and the like may be added to reductively trap by-produced t-butyl cation.

When dehydration reaction is performed in each step, examples of the dehydrating agent to be used include sulfuric acid, phosphorus pentaoxide, phosphorus oxychloride, N,N'-dicyclohexylcarbodiimide, alumina, polyphosphoric acid and the like.

In the present specification, the protecting group includes protecting group of hydroxyl group of alcohol and the like and phenolic hydroxyl group, protecting group of carbonyl group of aldehyde, protecting group of carbonyl group of ketone, protecting group of carboxyl group, thiol-protecting group, protecting group of amino group, protecting group of aromatic heterocycle such as imidazole, pyrrole, indole and the like, and the like.

Here, X, $Y^1$, $Y^2$, Z, W, L, $R^1$, $R^2$ and $R^3$ in the formulas in the following reaction schemes are as defined above.

In any step of the production methods shown below, substituent on ring A can be converted to a desired functional group by combining chemical reactions known per se in each production method. The substituent on ring A is not limited as long as it does not influence the reaction. Examples of the chemical reaction include oxidation reaction, reduction reaction, alkylation reaction, acylation reaction, ureation reaction, hydrolysis reaction, amination reaction, esterification reaction, coupling reaction, condensation reaction, deprotection reaction and the like. These reactions are performed according to a method known per se. Examples of such method include the methods described in ORGANIC FUNCTIONAL GROUP PREPARATIONS, 2nd edition, Academic Press (Academic Press Inc.), 1989, or Comprehensive Organic Transformations: A Guide to Functional Group Preparations, 2nd edition, Wiley-VCH, 1999 and the like, and the like.

Compound (I) can be produced from compound (2) by the method shown in reaction scheme 1.

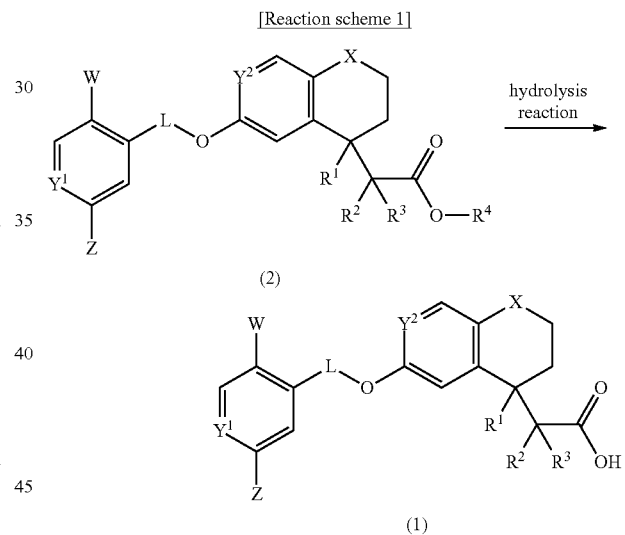

[Reaction scheme 1]

wherein $R^4$ is an optionally substituted $C_{1-6}$ alkyl group or an optionally substituted $C_{7-16}$ aralkyl group, and other symbols are as defined above.

In the present specification, the "optionally substituted $C_{7-16}$ aralkyl group" is an "optionally substituted hydrocarbon group" wherein the hydrocarbon group is a "$C_{7-16}$ aralkyl group".

Compound (2) can be produced from compound (10) by the method shown in reaction scheme 2.

[Reaction scheme 2]
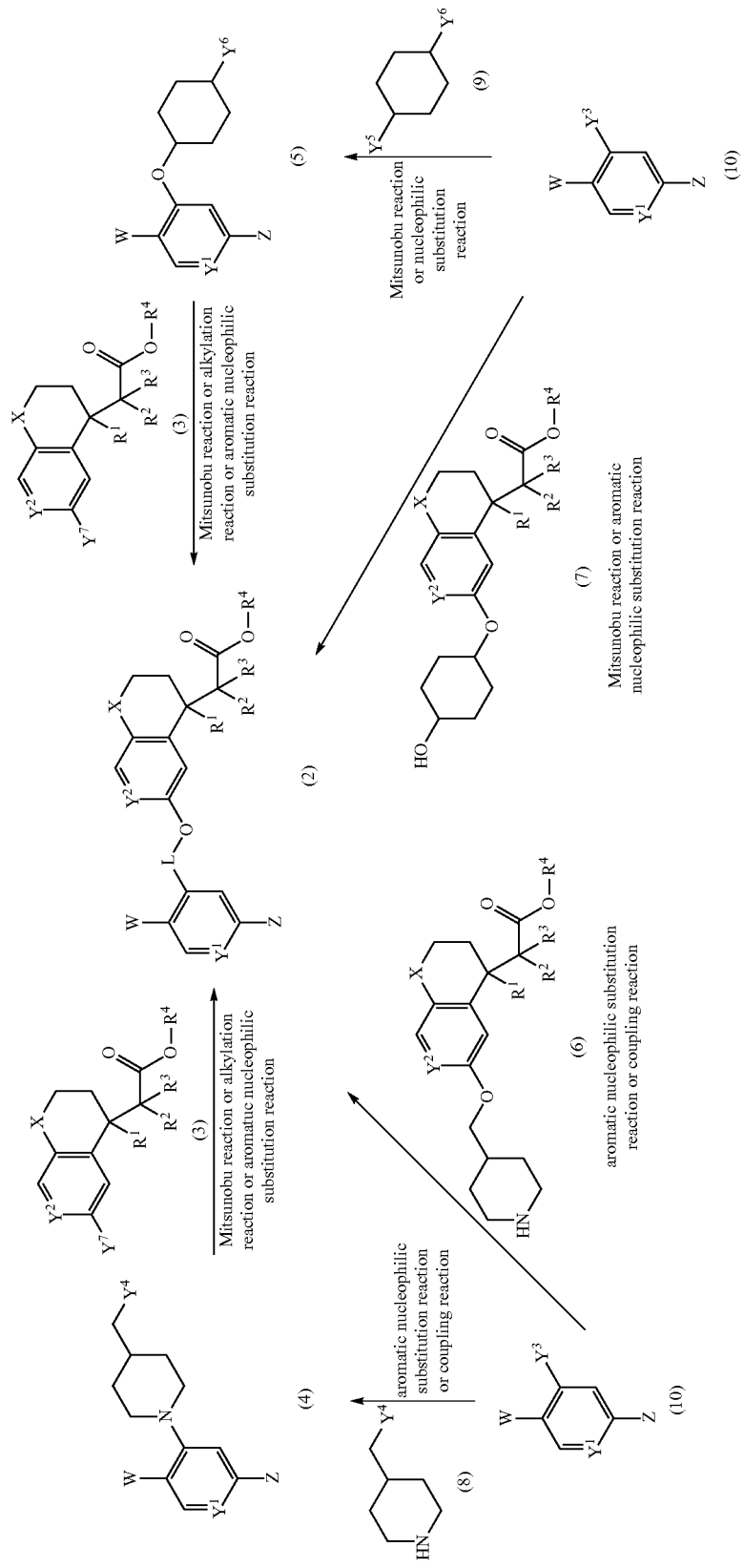

wherein $Y^3$, $Y^4$, $Y^5$ and $Y^6$ are each an optionally protected hydroxyl group or a leaving group (e.g., a halogen atom or —$OSO_2Me$, —$OSO_2$(4-tolyl), —$OSO_2CF_3$ and the like), $Y^7$ is a hydroxyl group or a halogen atom, and other symbols are as defined above. In the present specification, the optionally protected hydroxyl group is, for example, a hydroxyl group optionally protected by a hydroxy-protecting group mentioned below.

Compound (2) wherein $Y^4$ or $Y^6$ is a leaving group can be produced by, for example, an alkylation reaction of compound (5) with compound (3). This reaction is performed in the presence of a base in an inert solvent. Examples of the base include alkali metal hydride, inorganic base, basic salt, alkali metal alkoxide, organic base, organic lithium, metal amide and the like.

Compound (2-1) can be produced from compound (11-1) by the method shown in reaction scheme 3.

[Reaction scheme 3]

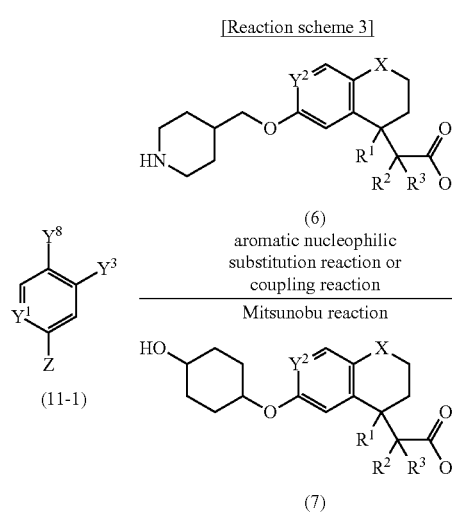

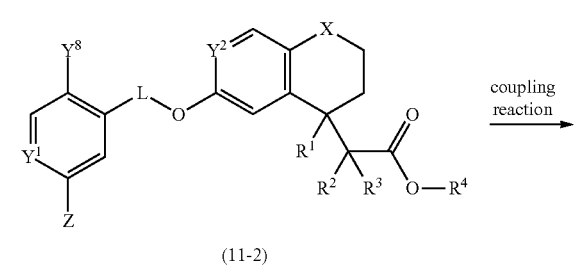

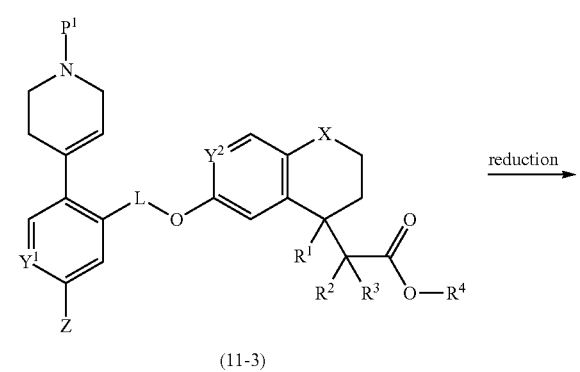

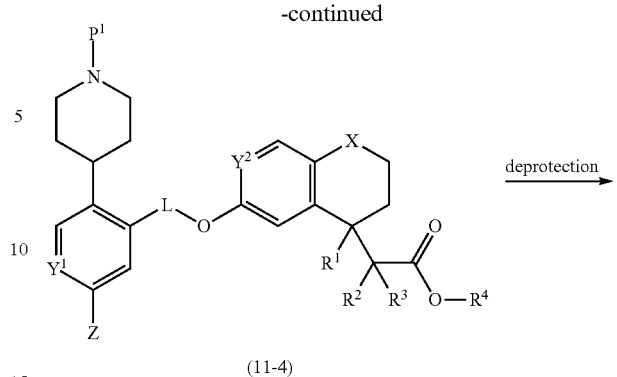

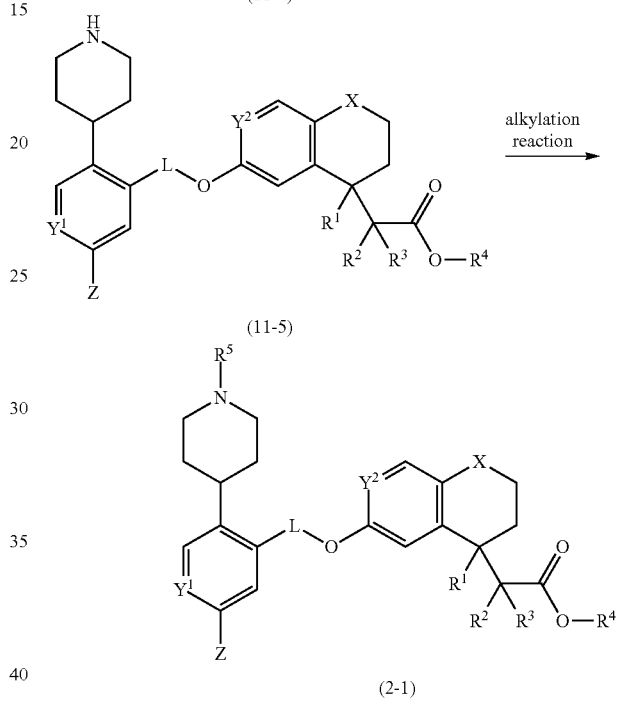

wherein $Y^8$ is a leaving group (e.g., a halogen atom or —$OSO_2Me$, —$OSO_2$ (4-tolyl), —$OSO_2CF_3$ and the like), $R^5$ is an optionally substituted hydrocarbon group, $P^1$ is a protecting group, and other symbols are as defined above.

Compound (2-1) can be produced by an alkylation reaction of compound (11-5). Alkylation reaction can be performed according to the method shown in reaction scheme 2, or according thereto.

Compound (11-4-1) can be produced from compound (11-1) by the method shown in reaction scheme 4.

[Reaction scheme 4]

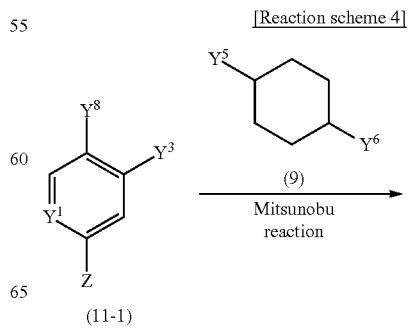

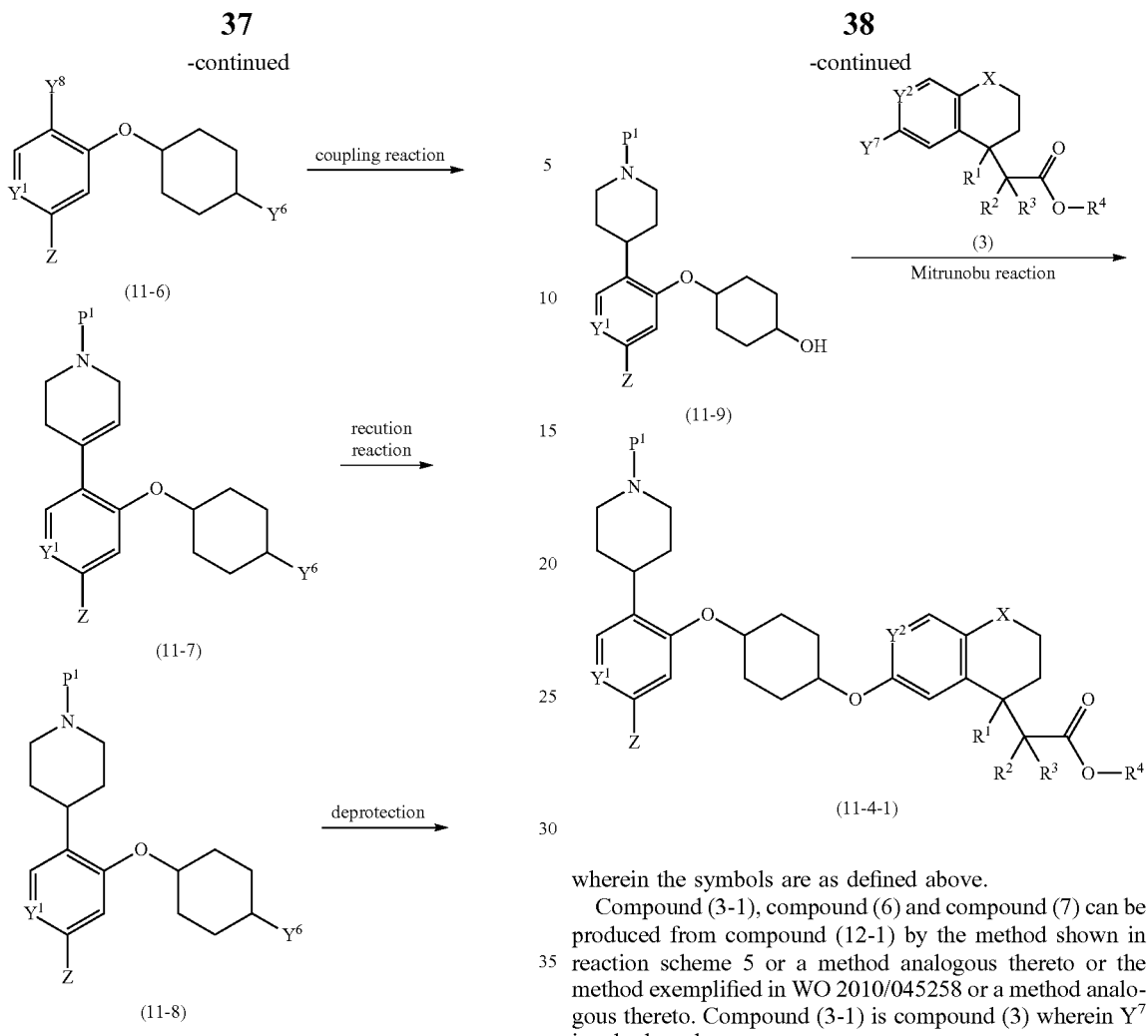
wherein the symbols are as defined above.
Compound (3-1), compound (6) and compound (7) can be produced from compound (12-1) by the method shown in reaction scheme 5 or a method analogous thereto or the method exemplified in WO 2010/045258 or a method analogous thereto. Compound (3-1) is compound (3) wherein $Y^7$ is a hydroxyl group.

[Reaction scheme 5]
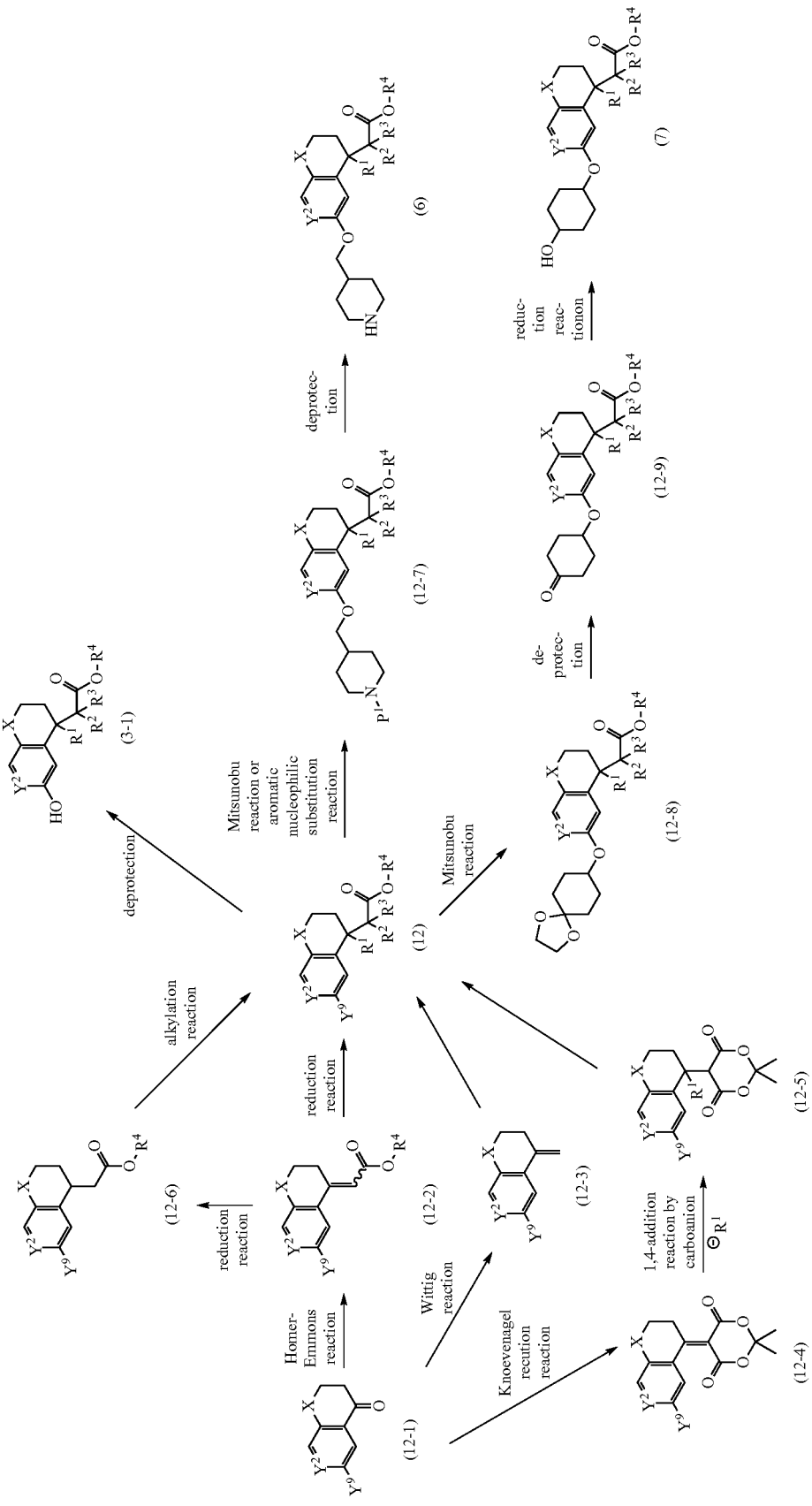

wherein $Y^9$ is a halogen atom, an optionally substituted $C_{1-6}$ alkyl group, an optionally substituted $C_{1-6}$ alkoxy group or an optionally protected hydroxyl group, and other symbols are as defined above.

Compound (12) can be produced by converting the Meldrum's acid moiety of compound (12-5) to an ester. This reaction can be performed by reacting methanol or ethanol in an inert solvent such as DMF and the like.

Compound (12) can be produced by an alkylation reaction of compound (12-6). Alkylation reaction can be performed according to the method shown in reaction scheme 2, or according thereto.

Compound (12) can be produced by a cyclopropanation reaction of the olefin moiety of compound (12-3). This reaction can be performed according to a method including reacting compound (12-3) and a diazoacetic acid ester in the presence of a catalyst (e.g., rhodium catalyst, ruthenium catalyst, copper catalyst etc.).

Compound (12-1-1) can be produced from compound (13-1) by the method shown in reaction scheme 6. Compound (12-1-1) is compound (12-1) wherein $Y^2$ is a nitrogen atom and X is an oxygen atom.

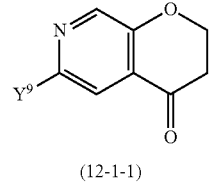

(12-1-1)

wherein $Y^{10}$ is an optionally protected hydroxyl group, and other symbols are as defined above.

Compound (13-3) can be produced by a homologation reaction of compound (13-2) with N,N-dimethylformamide dimethyl acetal and the like.

Compound (13-4) can be produced by an intramolecular cyclization reaction of compound (13-3) using an acid. As the acid to be used, hydrochloric acid and the like can be mentioned.

Compound (12-1-2) can be produced from compound (13-6) by the method shown in reaction scheme 7 or a method analogous thereto or the method exemplified in WO 2010/045258 or a method analogous thereto. Compound (12-1-2) is compound (12-1) wherein $Y^2$ is a nitrogen atom and X is a bond.

[Reaction scheme 6]

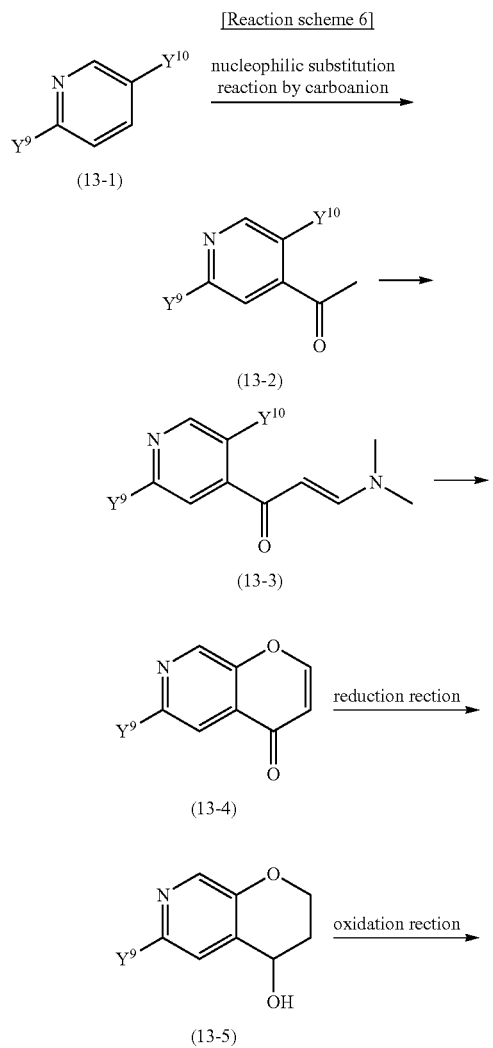

[Reaction scheme 7]

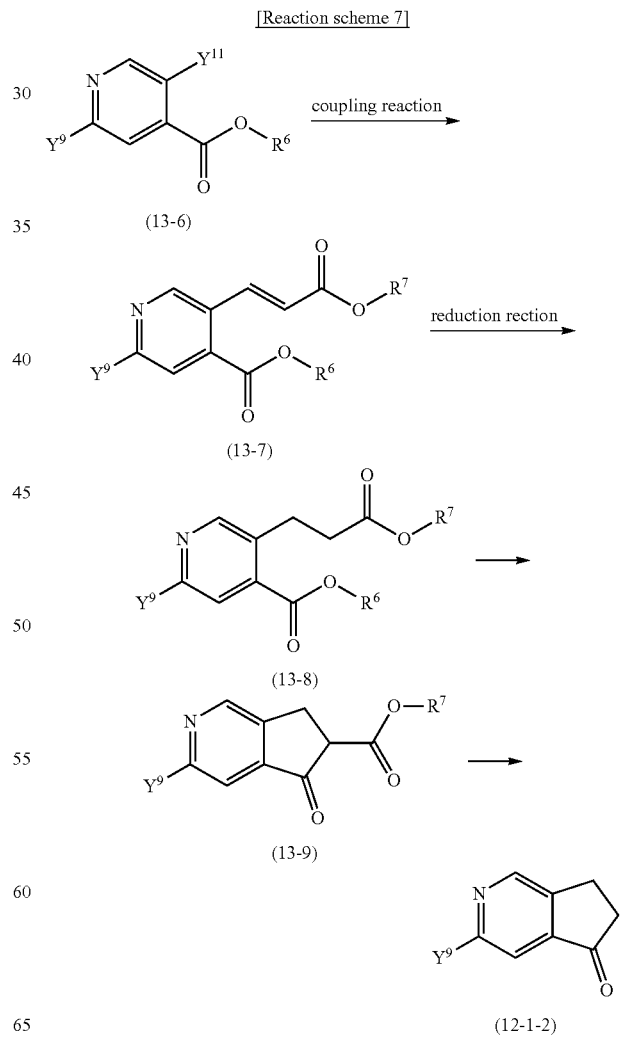

wherein $R^6$, $R^7$ are each an optionally substituted $C_{1-6}$ alkyl group or an optionally substituted $C_{7-16}$ aralkyl group, $Y^{11}$ is a leaving group, and other symbols are as defined above.

Compound (13-9) can be produced by an intramolecular cyclization reaction of compound (13-8) using a base. The base to be used includes sodium hydride and the like.

Compound (12-1-2) can be produced by a decarboxylation reaction of compound (13-9) by heating in DMSO/water solvent.

Compound (4-1) can be produced from compound (10) by the method shown in reaction scheme 8. Compound (4-1) is compound (4) wherein $Y^4$ is a hydroxyl group.

[Reaction scheme 8]

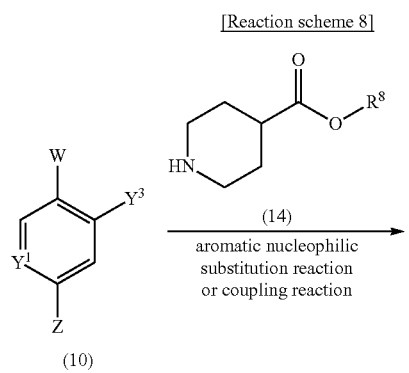

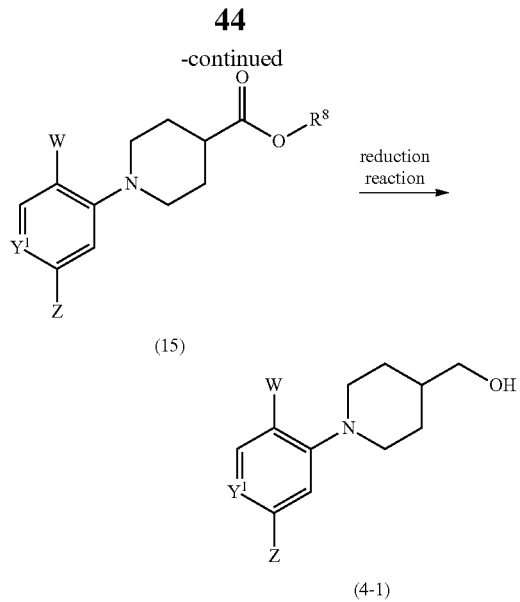

wherein $R^8$ is an optionally substituted $C_{1-6}$ alkyl group or an optionally substituted $C_{7-16}$ aralkyl group, and other symbols are as defined above.

Compound (15-1) and compound (4-1-1) can be produced from compound (11-1) by the method shown in reaction scheme 9.

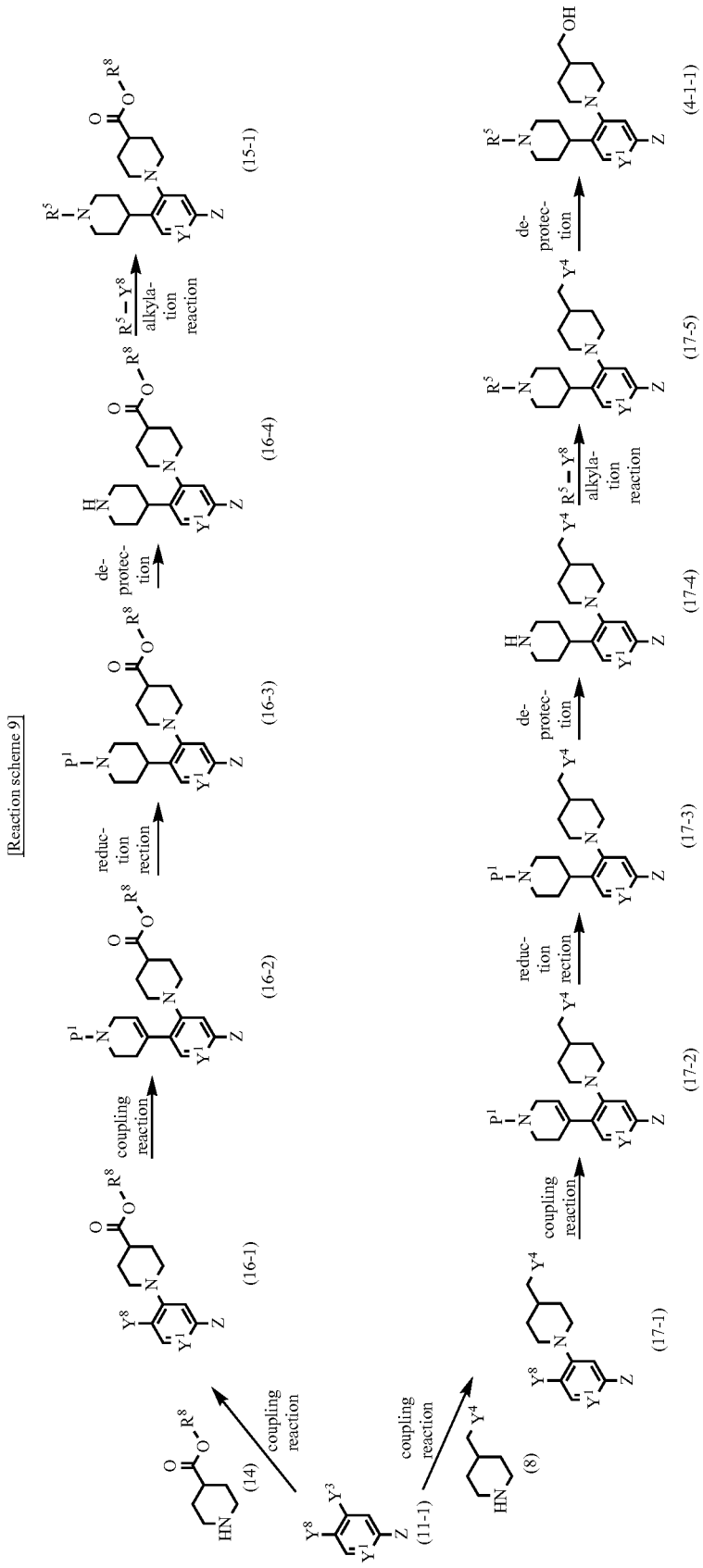

wherein the symbols are as defined above.

Compound (15-1) and compound (17-5) can be produced by an alkylation reaction of compound (16-4) and compound (17-4). Alkylation reaction can be performed according to the method shown in reaction scheme 2, or according thereto.

Compound (4-1-2) can be produced from compound (18-1) by the method shown in reaction scheme 10.

[Reaction scheme 10]

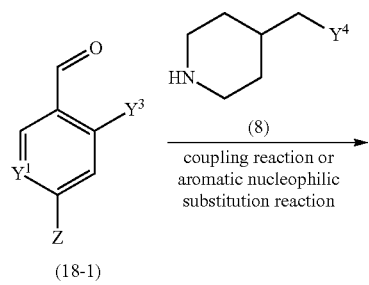

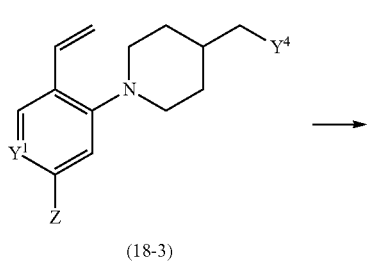

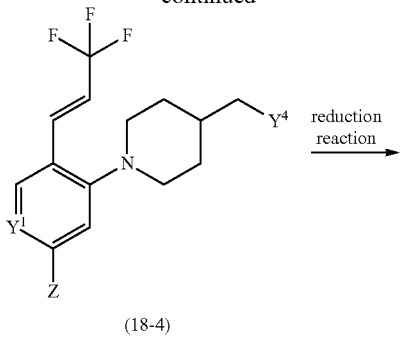

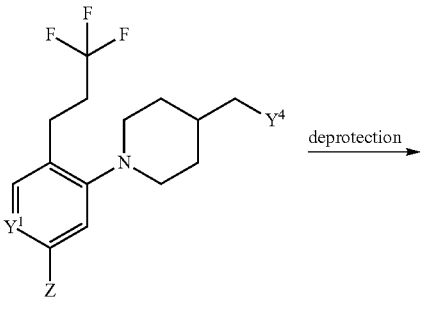

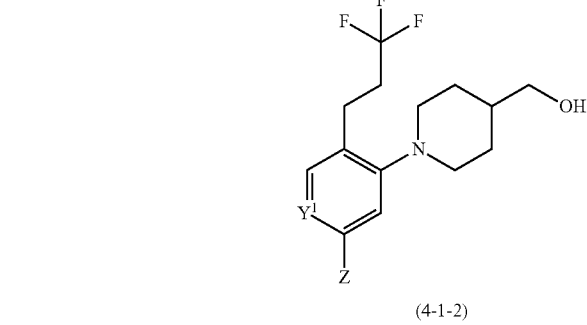

wherein the symbols are as defined above.

Compound (18-4) can be produced from compound (18-3) by, for example, the method described in Tetrahedron Letters, 2012, 53, pages 5503-5506 or according thereto. As the trifluoromethylating agent to be used, 1-trifluoromethyl-1,2-benzoiodoxol-3(1H)-one and the like can be mentioned. As the catalyst, copper(I) iodide, tetrakis(acetonitrile)copper (I) hexafluorophosphate and the like can be mentioned. Furthermore, an acid may be added to the reaction and, as such acid, p-toluenesulfonic acid and the like can be mentioned.

Compound (5-1) and compound (4-1-3) can be produced from compound (11-6) and compound (17-1) by the method shown in reaction scheme 11. Compound (5-1) and compound (4-1-3) are compound (5) and compound (4-1) wherein W is Ar. Here, Ar is an optionally substituted heterocyclic group or an optionally substituted $C_{6-14}$ aryl group.

[Reaction scheme 11]
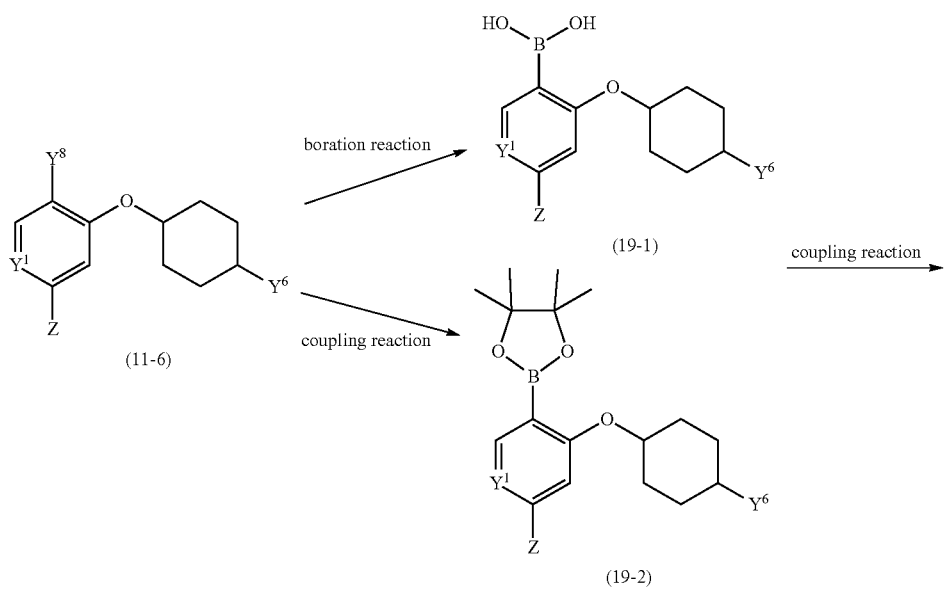
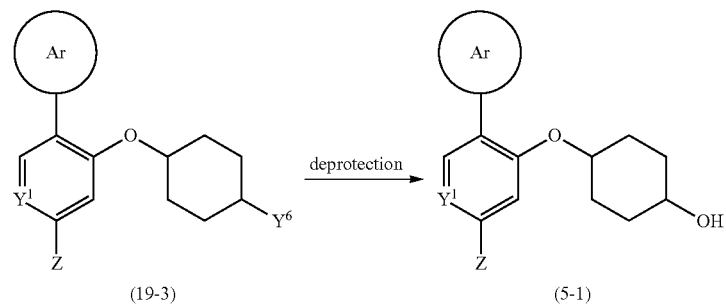
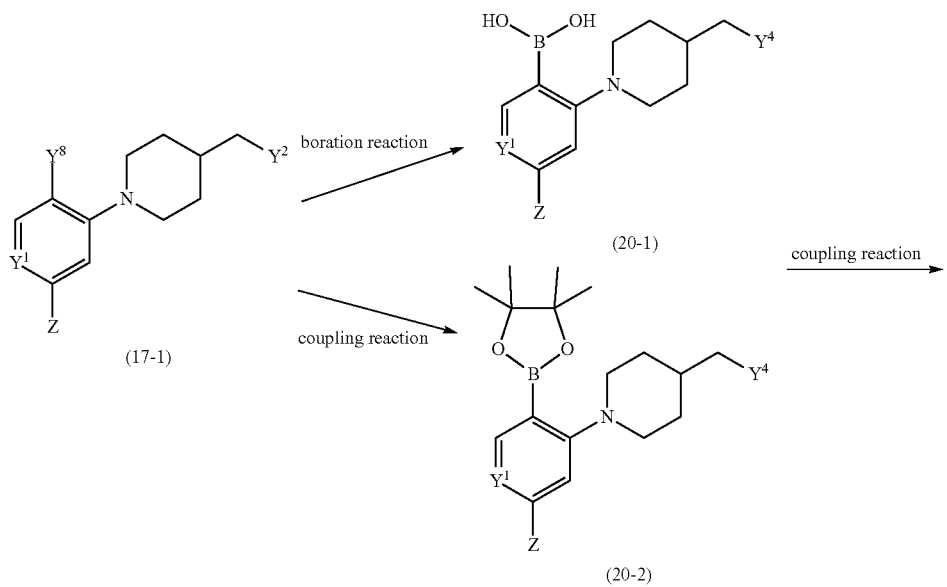

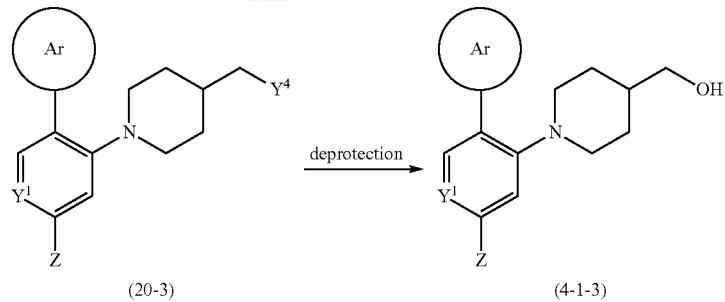

wherein the symbols are as defined above.

Compound (19-1) and compound (20-1) can be produced by a boration reaction of compound (11-6) and compound (17-1). As the base to be used, organic lithiums and the like can be mentioned. As the borating agent to be used, trimethyl borate, triisopropyl borate and the like can be mentioned.

Compound (4-1-4) can be produced from compound (18-2) by the method shown in reaction scheme 12.

[Reaction scheme 12]
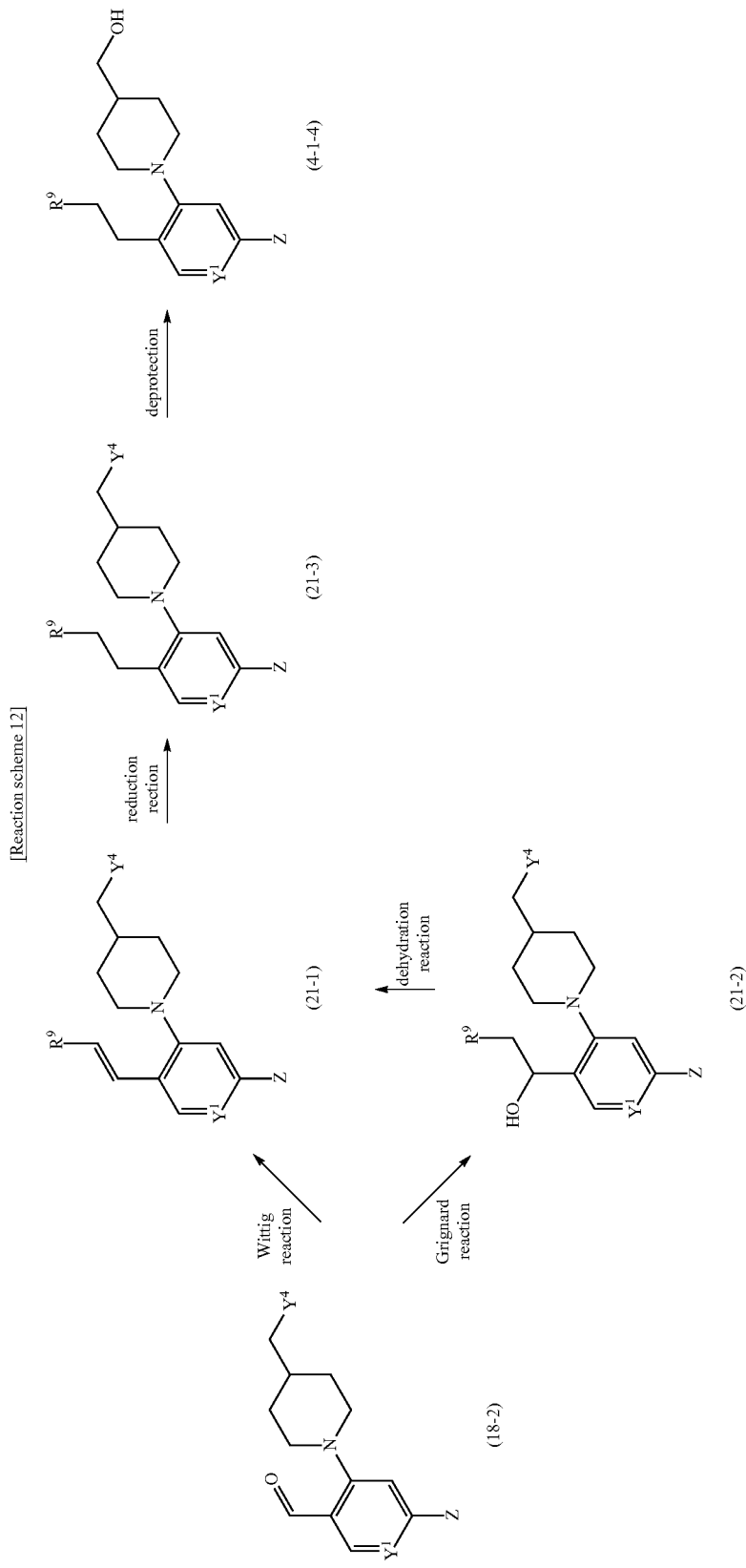

wherein R⁹ is an optionally substituted hydrocarbon group, and other symbols are as defined above.

Compound (21-1) can be produced by a dehydration reaction of compound (21-2). As the dehydrating agent to be used, methyl N-(triethylammoniumsulfonyl)carbamate and the like can be mentioned.

Compound (4-1-5) can be produced from compound (22-1) by the method shown in reaction scheme 13.

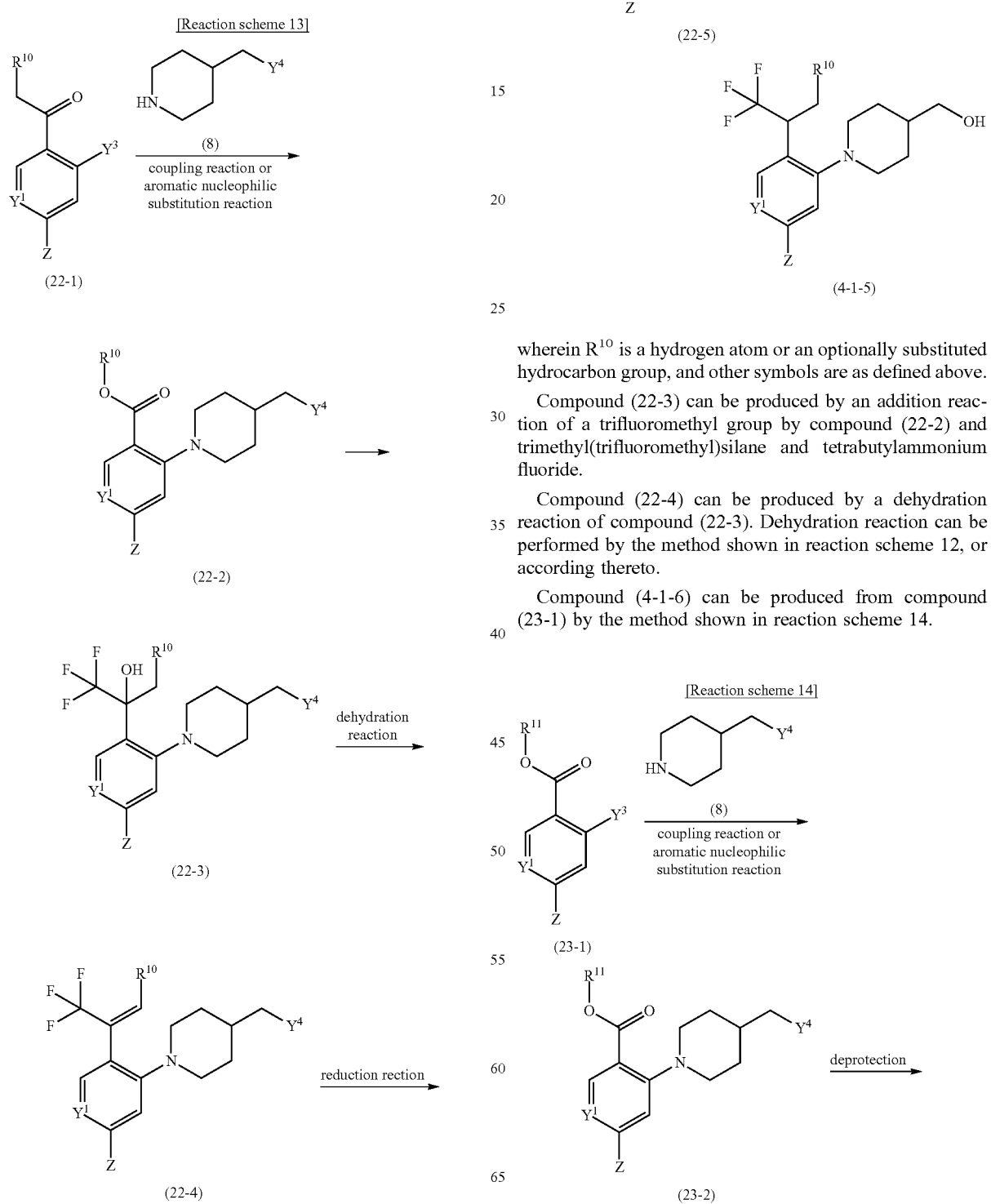

wherein $R^{10}$ is a hydrogen atom or an optionally substituted hydrocarbon group, and other symbols are as defined above.

Compound (22-3) can be produced by an addition reaction of a trifluoromethyl group by compound (22-2) and trimethyl(trifluoromethyl)silane and tetrabutylammonium fluoride.

Compound (22-4) can be produced by a dehydration reaction of compound (22-3). Dehydration reaction can be performed by the method shown in reaction scheme 12, or according thereto.

Compound (4-1-6) can be produced from compound (23-1) by the method shown in reaction scheme 14.

-continued

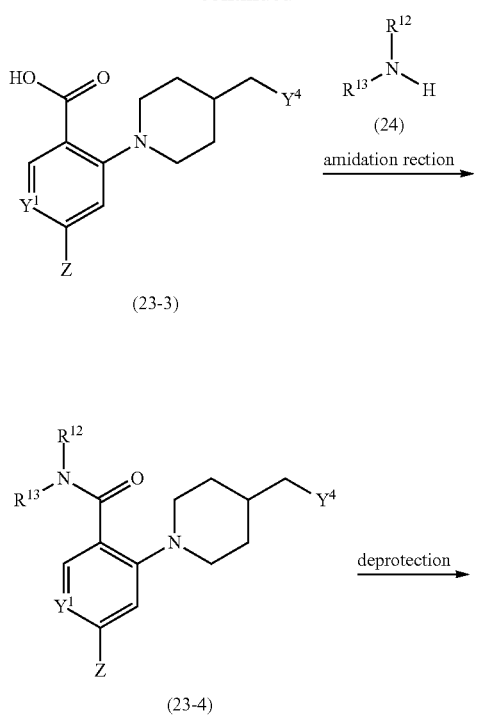

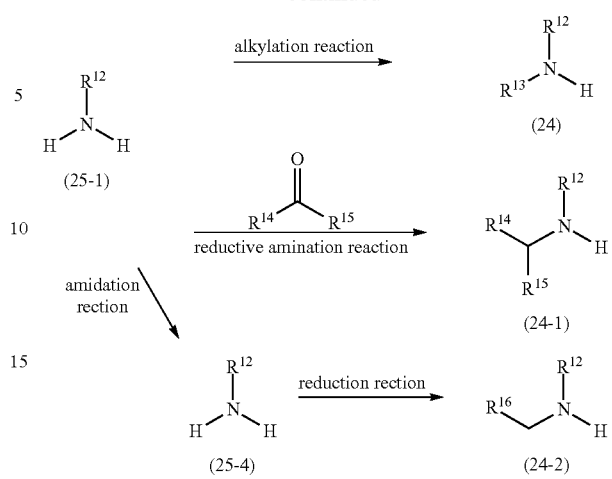

wherein $P^2$ is a protecting group, $R^{14}$, $R^{15}$ and $R^{16}$ are each a hydrogen atom, an optionally substituted $C_{1-6}$ alkyl group, an optionally substituted $C_{7-16}$ aralkyl group or an optionally substituted $C_{6-14}$ aryl group, and other symbols are as defined above.

Compound (25-3) and compound (24) can be produced by an alkylation reaction of compound (25-2) and compound (25-1). Alkylation reaction can be performed according to the method shown in reaction scheme 2, or according thereto.

Compound (24-3) can be produced from compound (25-5) by the method shown in reaction scheme 16.

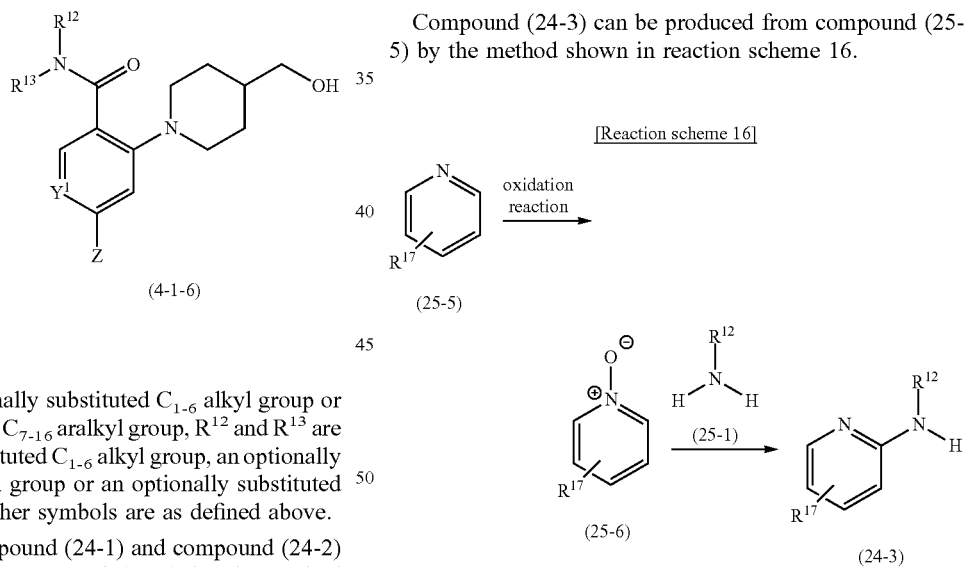

wherein $R^{11}$ is an optionally substituted $C_{1-6}$ alkyl group or an optionally substituted $C_{7-16}$ aralkyl group, $R^{12}$ and $R^{13}$ are each an optionally substituted $C_{1-6}$ alkyl group, an optionally substituted $C_{7-16}$ aralkyl group or an optionally substituted $C_{6-14}$ aryl group, and other symbols are as defined above.

Compound (24), compound (24-1) and compound (24-2) can be produced from compound (25-1) by the method shown in reaction scheme 15.

wherein $R^{17}$ is a substituent, and other symbols are as defined above.

Compound (24-3) can be produced by the reaction of compound (25-6) with compound (25-1). The reaction is performed in the presence of phosphate represented by bromotris(pyrrolidino)phosphonium hexafluorophosphate (PyBrop) and a base. Examples of the base include alkali metal hydride, inorganic base, basic salt, alkali metal alkoxide, organic base, organic lithium, metal amide and the like.

Compound (10-1) can be produced from compound (26-1) by the method shown in reaction scheme 17.

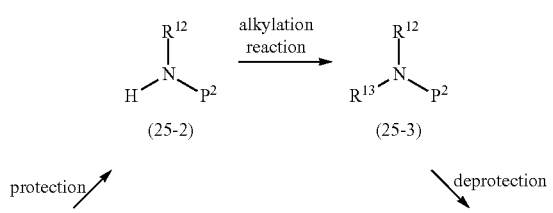

[Reaction scheme 17]

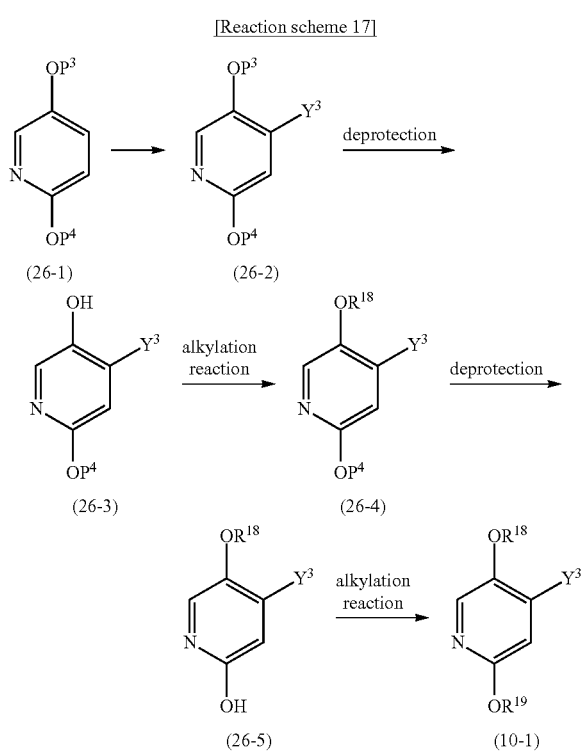

wherein $P^3$ and $P^4$ are protecting groups, $R^{18}$ and $R^{19}$ are each an optionally substituted hydrocarbon group, and other symbols are as defined above.

Compound (26-2) can be produced by halogenation reaction of compound (26-1). As the base to be used, organic lithiums and the like can be mentioned; and as the halogenating agent, iodine, bromine, N-iodosuccinimide, N-bromosuccinimide (NBS), N-chlorosuccinimide (NCS), 1,2-dibromo-1,1,2,2-tetrafluoroethane and the like can be mentioned.

Compound (10-1) can be produced by alkylation of the hydroxyl group of compound (26-5). In this reaction, alkyl halide and the like are reacted in the presence of silver oxide and the like in an inert solvent such as toluene and the like.

Compound (10-2) can be produced from compound (27) by the method shown in reaction scheme 18.

[Reaction scheme 18]

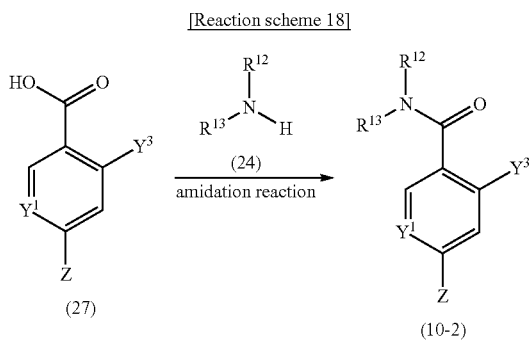

wherein the symbols are as defined above.

In each of the aforementioned reactions, when the starting compound has an amino group, a carboxy group, a hydroxy group, a carbonyl group or a mercapto group as a substituent, a protecting group generally used in the peptide chemistry and the like may be introduced into these groups, and the object compound can be obtained by eliminating the protecting group as necessary after the reaction.

Examples of the amino-protecting group include a formyl group; a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-11}$ aralkyl group (e.g., benzyl), a phenyl group, a trityl, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_7$-10 aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl), and the like. These groups are optionally substituted by 1 to 3 substituents selected from a halogen atom, a $C_{1-6}$ alkyl group, a $C_{1-6}$ alkoxy group and a nitro group.

Examples of the carbonyl-protecting group include a cyclic acetal (e.g., 1,3-dioxane), a non-cyclic acetal (e.g., a di-$C_{1-6}$ alkylacetal) and the like.

Examples of the mercapto-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylaminocarbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

The above-mentioned protecting groups can be removed by a method known per se, for example, the method described in Protective Groups in Organic Synthesis, John Wiley and Sons (1980) and the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method and the like can be mentioned.

In compound (I) obtained by each of the above-mentioned production methods, a functional group in a molecule can also be converted to a desired functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

Compound (I) obtained by each of the above-mentioned production methods can be isolated and purified by a known means such as concentration, concentration under reduced pressure, solvent extraction, crystallization, recrystallization, phase transfer, chromatography and the like. In addition, the starting compounds used for each of the above-mentioned production methods can be isolated and purified by a known means similar to the aforementioned methods. These starting compounds may be used in the form of a reaction mixture without isolation, as a starting material for the next step.

When compound (I) contains an isomer such as an optical isomer, a stereoisomer, a regioisomer or a rotamer, any one of them and a mixture thereof are also encompassed in compound (I) For example, when compound (I) contains an optical isomer, an optical isomer resolved from racemate is also encompassed in compound (I). Each of these isomers can be obtained as a single product by a synthesis means, separation means (e.g., concentration, solvent extraction, column chromatography, recrystallization etc.), optical resolution means (e.g., fractional recrystallization method, chiral column method, diastereomer method etc.) and the like, which are known per se.

Compound (I) may be a crystal, and the crystal form may be single or a mixture of crystal forms, both of which are encompassed in compound (I). The crystal can be produced by a crystallization method known per se.

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

In the present specification, the melting point means that measured using, for example, a micromelting point apparatus (Yanako, MP-500D or Buchi, B-545), a DSC (differential scanning calorimetry) device (SEIKO, EXSTAR6000) or the like.

In general, the melting points vary depending on the measurement apparatuses, the measurement conditions and the like. The crystal in the present specification may show different values from the melting point described in the present specification, as long as they are within each of a general error range.

The crystal of the present invention is superior in physicochemical properties (e.g., melting point, solubility, stability) and biological properties (e.g., pharmacokinetics (absorption, distribution, metabolism, excretion), efficacy expression), and thus it is extremely useful as a medicament.

Compound (I) may be a solvate (e.g., hydrate etc.), or a non-solvate (e.g., non-hydrate etc.), and both are encompassed in compound (I).

A compound labeled with an isotope (e.g., $^3$H, $^{13}$C, $^{14}$C, $^{18}$F, $^{35}$S, $^{125}$I etc.) and the like is also encompassed in compound (I).

Compound (I) also encompasses a deuterium conversion form wherein $^1$H is converted to $^2$H(D).

Compound (I) labeled or substituted with an isotope can be used as, for example, a tracer (PET tracer) used for Positron Emission Tomography (PET), and may be useful in the fields of medical diagnosis and the like.

Compound (I) and a prodrug thereof (hereinafter, these are collectively abbreviated as the compound of the present invention) may have a GPR40 receptor function modulating action, particularly, a GPR40 agonist activity. GPR40 agonist activates GPR40 expressed in pancreatic β cells to promote insulin secretion, and may activate GPR40 expressed in the intestine to promote glucagon-like peptide-1 (glucagon-like peptide-1; GLP-1) secretion. That is, the compound of the present invention may have a hypoglycemic action, an insulin secretagogue action, a GLP-1 secretagogue action and a pancreatic β cell protecting action. The GLP-1 secretagogue action of the compound of the present invention can be measured using, for example, an ELISA kit containing a GLP-1 antibody. Moreover, the compound of the present invention may have a glucose-dependent insulinotropic polypeptide (GIP) secretagogue action, a food ingestion suppressive action and a glucagon secretion suppressive action.

The compound of the present invention may be expected to show low toxicity (e.g., acute toxicity, chronic toxicity, genetic toxicity, reproductive toxicity, cardiotoxicity, carcinogenicity, cytotoxicity) and can be safely administered a mammal (e.g., mouse, rat, hamster, rabbit, cat, dog, bovine, sheep, monkey, human) directly or as a pharmaceutical composition by mixing same with a pharmacologically acceptable carrier and the like.

The compound of the present invention may be useful as modulators of physiological function in which GPR40 receptor is involved or as agents for the prophylaxis or treatment of pathology or disease in which GPR40 receptor is involved.

To be specific, the compound of the present invention may be useful as an agent for the prophylaxis or treatment of diabetes (e.g., type 1 diabetes, type 2 diabetes, gestational diabetes, obese diabetes), an insulin secretagogue, a pancreatic β cell protector, a GLP-1 secretion promoter, a GIP secretion promoter, an agent for the prophylaxis or treatment of impaired glucose tolerance (IGT) and an agent for preventing progression of impaired glucose tolerance to diabetes.

Particularly, the compound of the present invention may be useful as blood glucose level-dependent insulin secretagogues based on the GPR40 agonist activity thereof. That is different from sulfonylureas, the compound of the present invention may be useful as insulin secretagogues that do not cause hypoglycemia.

Furthermore, the compound of the present invention may be used as an agent for the prophylaxis or treatment of obesity, hyperlipidemia (e.g., hypertriglyceridemia, hypercholesterolemia, high LDL-cholesterolemia, hypo HDL-cholesterolemia, postprandial hyperlipidemia), hypertension, cardiac failure, diabetic complications [e.g., neuropathy, nephropathy, diabetic retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (according to the diagnostic criteria for Japanese people as reported in 2005 by the Japan Society for the Study of Obesity and the like, the metabolic syndrome refers to males having an abdominal circumference of 85 cm or above and females having an abdominal circumference of 90 cm or above and satisfying two items out of three items of: systolic blood pressure of not less than 130 or diastolic blood pressure of not less than 85 mmHg, neutral triglyceride not less than 150 mg/dl or HDLc less than 40 mg/dl, and fasting blood sugar level (venous plasma glucose concentration) not less than 110 mg/dl) and the like.

For diagnostic criteria of diabetes, Japan Diabetes Society reported diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) and WHO reported diagnostic criteria of diabetes.

According to these reports, diabetes is a condition showing a fasting blood glucose level (glucose concentration of intravenous plasma) of not less than 126 mg/dl, or a 75 g oral glucose tolerance test 2 h level (glucose concentration of intravenous plasma) of not less than 200 mg/dl.

According to the above-mentioned reports by ADA and WHO, impaired glucose tolerance is a condition showing a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a fasting blood glucose level (glucose concentration of intravenous plasma) of not less than 110 mg/dl and less than 126 mg/dl is called IFG (Impaired Fasting Glycemia).

The compound of the present invention may also be useful as an agent for the prophylaxis or treatment of diabetes, borderline type, impaired glucose tolerance, IFG (Impaired Fasting Glucose) and IFG (Impaired Fasting Glycemia), as determined according to the above-mentioned diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention may also be useful as a therapeutic agent for diabetes with sulfonylurea secondary failure and may afford a superior insulin secretion effect and a hypoglycemic effect for diabetic patients for whom sulfonylurea compounds and fast-acting insulin secretagogues fail to provide an insulin secretion effect, and therefore, fail to provide a sufficient hypoglycemic effect.

As the sulfonylurea compound here, a compound having a sulfonylurea skeleton or a derivative thereof (e.g., tolbutamide, glibenclamide, gliclazide, chlorpropamide, tolazamide, acetohexamide, glyclopyramide, glimepiride, glipizide, glybuzole and the like) can be mentioned.

As the fast-acting insulin secretagogue, a compound that promotes insulin secretion from pancreatic B cell in the same manner as a sulfonylurea compound, though it does not have a sulfonylurea skeleton, such as glinide compounds (e.g., repaglinide, senaglinide, nateglinide, mitiglinide or a calcium salt hydrate thereof etc.), and the like, can be mentioned.

The compound of the present invention may also be useful as an agent for the prophylaxis or treatment of, for example, cognitive impairment, osteoporosis, cachexia (e.g., cancerous cachexia, tuberculous cachexia, diabetic cachexia, hemopathic cachexia, endocrinopathic cachexia, infectious cachexia or cachexia induced by acquired immunodeficiency syndrome), fatty liver, polycystic ovary syndrome, renal disease (e.g., diabetic nephropathy, glomerulonephritis, glomerulosclerosis, nephrotic syndrome, hypertensive nephrosclerosis, end-stage renal disorder), muscular dystrophy, myocardial infarction, angina pectoris, cerebrovascular disorder (e.g., cerebral infarction, cerebral apoplexy), insulin resistance syndrome, syndrome X, hyperinsulinemia, perception disorder in hyperinsulinemia, tumor (e.g., leukemia, breast cancer, prostate cancer, skin cancer), irritable bowel syndrome, acute or chronic diarrhea, inflammatory disease (e.g., arteriosclerosis (e.g., atherosclerosis), rheumatoid arthritis, spondylitis deformans, osteoarthritis, lumbago, gout, postoperative or post-traumatic inflammation, swelling, neuralgia, pharyngolaryngitis, bladder inflammation, hepatitis (including nonalcoholic steatohepatitis), pneumonia, pancreatitis, inflammatory colitis, ulcerative colitis, chronic obstructive pulmonary diseases (COPD)), visceral fat syndrome, foot ulcer, sepsis, psoriasis and the like.

In addition, the compound of the present invention can also be used for the improvement of the symptoms of abdominal pain, nausea, vomiting, uncomfortable feeling in the upper abdomen and the like, which are associated with peptic ulcer, acute or chronic gastritis, biliary dyskinesia, cholecystitis and the like, and the like.

Based on a pancreatic β cell protection action of the compound of the present invention, it can be used for the prognosis improvement in pancreatic islet transplantation.

The compound of the present invention may also be useful for decreasing the visceral fat, suppressing visceral fat accumulation, improving sugar metabolism, improving lipid metabolism, insulin sensitizing, suppressing oxidized LDL production, improving lipoprotein metabolism, improving coronary metabolism, preventing or treating cardiovascular complication, preventing or treating heart failure complication, decreasing blood remnant, preventing or treating anovulation, preventing or treating hirsutism, preventing or treating hyperandrogenism and the like.

The compound of the present invention may also be used for the secondary prevention and the suppression of progression of the above-mentioned various diseases (e.g., cardiovascular event such as myocardial infarction and the like).

A medicament containing the compound of the present invention can be safely administered solely to a mammal or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal tablet and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The content of the compound of the present invention in a pharmaceutical preparation is about 0.01 to about 100% by weight relative to the whole preparation. While the dose of the compound of the present invention varies depending on the administration subject, administration route, diseases, condition and the like, for example, the compound of the present invention (as an active ingredient) can be orally administered to a patient with diabetes (body weight about 60 kg) in about 0.01 to about 30 mg/kg body weight per day, preferably about 0.1 to about 20 mg/kg body weight per day, more preferably about 1 to about 20 mg/kg body weight per day, which may be given at once or in several portions (e.g., 1-3 portions) a day.

As the above-mentioned pharmacologically acceptable carrier, various organic or inorganic carrier substances conventionally used as a preparation material can be mentioned. For example, excipient, lubricant, binder and disintegrant for solid preparations; solvent, solubilizing agents, suspending agent, isotonic agent, buffer and soothing agent for liquid preparations and the like can be mentioned. Where necessary, conventional additives such as preservatives, antioxidants, colorants, sweetening agents, adsorbing agents, wetting agents and the like can be used.

As the excipient, for example, lactose, sucrose, D-mannitol, starch, corn starch, crystalline cellulose, light anhydrous silicic acid and the like can be mentioned.

As the lubricant, for example, magnesium stearate, calcium stearate, talc, colloidal silica and the like can be mentioned.

As the binder, for example, crystalline cellulose, sucrose, D-mannitol, dextrin, hydroxypropylcellulose, hydroxypropylmethylcellulose, polyvinylpyrrolidone, starch, saccharose, gelatin, methylcellulose, carboxymethylcellulose sodium and the like can be mentioned.

As the disintegrant, for example, starch, carboxymethylcellulose, carboxymethylcellulose calcium, carboxymethylstarch sodium, L-hydroxypropylcellulose and the like can be mentioned.

As the solvent, for example, water for injection, alcohol, propylene glycol, macrogol, sesame oil, corn oil, olive oil and the like can be mentioned.

As the solubilizing agents, for example, polyethylene glycol, propylene glycol, D-mannitol, benzyl benzoate, ethanol, trisaminomethane, cholesterol, triethanolamine, sodium carbonate, sodium citrate and the like can be mentioned.

As the suspending agent, for example, surfactants such as stearyltriethanolamine, sodium lauryl sulfate, lauryl aminopropionate, lecithin, benzalkonium chloride, benzethonium chloride, glycerol monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like, and the like can be mentioned.

As the isotonic agent, for example, glucose, D-sorbitol, sodium chloride, glycerin, D-mannitol and the like can be mentioned.

As the buffer, for example, buffers such as phosphates, acetates, carbonates, citrates and the like, and the like can be mentioned.

As the soothing agent, for example, benzyl alcohol and the like can be mentioned.

As the preservative, for example, p-hydroxybenzoates, chlorobutanol, benzyl alcohol, phenethyl alcohol, dehydroacetic acid, sorbic acid and the like can be mentioned.

As the antioxidant, for example, sulfites, ascorbic acid, α-tocopherol and the like can be mentioned.

As the colorant, for example, water-soluble edible tar pigments (e.g., food colors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment and the like), natural pigments (e.g., β-carotene, chlorophil, red iron oxide etc.) and the like can be mentioned.

As the sweetening agent, for example, saccharin sodium, dipotassium glycyrrhizinate, aspartame, stevia and the like can be mentioned.

Moreover, the compound of the present invention can be used in combination with drugs other than the compound of the present invention.

As the drugs that can be used in combination with the compound of the present invention (hereinafter sometimes to be abbreviated as a concomitant drug), for example, therapeutic agents for diabetes, therapeutic agents for diabetic complications, therapeutic agents for hyperlipidemia, antihypertensive agents, antiobesity agents, diuretics, chemotherapeutic agents, immunotherapeutic agents, antiinflammatory agents, antithrombotic agents, therapeutic agents for osteoporosis, vitamins, antidementia agents, erectile dysfunction improving drugs, therapeutic agents for pollakisuria or anischuria, therapeutic agents for dysuria and the like can be mentioned. Specifically, the following agents can be mentioned.

Examples of therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, the compound described in WO 2007/013694, WO 2007/018314, WO 2008/093639 and WO 2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl-peptidase IV inhibitors (e.g., Alogliptin or a salt thereof (preferably benzoate), Vildagliptin, Sitagliptin, Saxagliptin, BI1356, GRC8200, MP-513, PF-00734200, PHX1149, SK-0403, ALS2-0426, TA-6666, TS-021, KRP-104, Trelagliptin or a salt thereof (preferably, succinate)), β3 agonist (e.g., N-5984), GPR40 agonist (e.g., Fasiglifam or a hydrate thereof (preferably, 0.5 hydrate), the compound described in WO 2004/041266, WO 2004/106276, WO 2005/063729, WO 2005/063725, WO 2005/087710, WO 2005/095338, WO 2007/013689 and WO 2008/001931), GLP-1 receptor agonists (e.g., GLP-1, GLP-1 MR agent, Liraglutide, Exenatide, AVE-0010, BIM-51077, Aib(8,35)hGLP-1(7,37)NH$_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, Canagliflozin, Empagliflozin, Ipragliflozin, Tofogliflozin, PF-04971729, TS-071), SGLT1 inhibitor, 11β-hydroxysteroid dehydrogenase inhibitors (e.g., BVT-3498, INCB-13739), adiponectin or agonist thereof, IKK inhibitors (e.g., AS-2868), leptin resistance improving drugs, somatostatin receptor agonists, glucokinase activators (e.g., Piragliatin, AZD1656, AZD6370, TTP-355, the compound described in WO 2006/112549, WO 2007/028135, WO 2008/047821, WO 2008/050821, WO 2008/136428 and WO 2008/156757), GIP (Glucose-dependent insulinotropic peptide), GPR119 agonists (e.g., PSN821, MBX-2982, APD597), FGF21, FGF analogue and the like.

Examples of the therapeutic agents for diabetic complications include aldose reductase inhibitors (e.g., Tolrestat, Epalrestat, Zopolrestat, Fidarestat, CT-112, ranirestat (AS-3201), Lidorestat), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole), compound described in WO 2004/039365), PKC inhibitors (e.g., ruboxistaurin mesylate), AGE inhibitors (e.g., ALT-946, N-phenacylthiazolium bromide (ALT-766), EXO-226, Pyridorin, Pyridoxamine), GABA receptor agonists (e.g., gabapentin, Pregabalin), serotonin•noradrenaline reuptake inhibitors (e.g., duloxetine), sodium channel inhibitors (e.g., Lacosamide), active oxygen scavengers (e.g., thioctic acid), cerebral vasodilators (e.g., tiapuride, mexiletine), somatostatin receptor agonists (BIM23190), apoptosis signal regulating kinase-1 (ASK-1) inhibitors and the like.

Examples of the therapeutic agent for hyperlipidemia include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterol (e.g., soysterol, gamma oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like.

Examples of the antihypertensive agent include angiotensin converting enzyme inhibitors (e.g., captopril, enalapril, delapril and the like), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil and the like), calcium antagonists (e.g., manidipine, nifedipine, amlodipine, efonidipine, nicardipine, cilnidipine and the like), R blockers (e.g., metoprolol, atenolol, propranolol, carvedilol, pindolol and the like), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor modulator, GABA modulator (e.g., topiramate), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β agonists (e.g., N-5984), diacylglycerol acyltransferase 1 (DGAT1) inhibitors, acetyl-CoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, remogliflozin), NFK inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN821, MBX-2982, APD597), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine or swine; human GLP-1 preparations genetically synthesized using *Escherichia coli* or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine or swine; human FGF21 preparations genetically synthesized using *Escherichia coli* or yeast; fragments or derivatives of FGF21), anorexigenic agents (e.g., P-57) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil), antitumor antibiotics (e.g., mitomycin, adriamycin), plant-derived antitumor drugs (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivatives, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

Examples of the antiinflammatory agents include non-steroidal antiinflammatory agents such as aspirin, acetaminophen, indomethacin and the like.

Examples of the antithrombotic agents include heparin (e.g., heparin sodium, heparin calcium, enoxaparin sodium, dalteparin sodium), warfarins (e.g., warfarin potassium), anti-thrombin drugs (e.g., argatroban, dabigatran)), FXa inhibitors (e.g., rivaroxaban, apixaban, edoxaban, YM150, the compound described in WO 02/06234, WO 2004/048363, WO 2005/030740, WO 2005/058823 and WO 2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, pamidronate disodium, alendronate sodium hydrate, incadronate disodium, risedronate disodium and the like.

Examples of the vitamins include vitamin $B_1$, vitamin $B_{12}$ and the like.

Examples of the antidementia drugs include tacrine, donepezil, rivastigmine, galanthamine and the like.

Examples of the erectile dysfunction improving drug include apomorphine, sildenafil citrate and the like.

Examples of the therapeutic agents for pollakisuria or anischuria include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like, can be used in combination with the compound of the present invention.

Furthermore, glycosylation inhibitors (e.g., ALT-711), nerve regeneration promoting drugs (e.g., Y-128, VX853, prosaptide), antidepressants (e.g., desipramine, amitriptyline, imipramine), antiepileptics (e.g., lamotrigine, Trileptal, Keppra, Zonegran, Pregabalin, Harkoseride, carbamazepine), antiarrhythmic agents (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin, gabapentin MR agent), $\alpha_2$ receptor agonists (e.g., clonidine), local analgesics (e.g., capsaicin), antianxiety drugs (e.g., benzothiazepines), phosphodiesterase inhibitors (e.g., sildenafil), dopamine receptor agonists (e.g., apomorphine), midazolam, Ketoconazole and the like can also be used in combination with the compound of the present invention.

The concomitant drug is preferably an insulin preparation, an insulin sensitizer (preferably pioglitazone or its hydrochloride), an α-glucosidase inhibitor (preferably voglibose), a biguanide (preferably metformin or hydrochloride thereof), a sulfonylurea (preferably glibenclamide, glimepiride), mitiglinide or calcium salt hydrate thereof, nateglinide, a dipeptidyl peptidase IV inhibitor (preferably alogliptin or benzoate thereof, trelagliptin or succinate thereof), SGLT2 inhibitor, GLP-1 receptor agonist and the like. For enhancing the food ingestion suppressive action, a combined use with a dipeptidyl peptidase IV inhibitor (preferably, alogliptin or a salt thereof) is more preferable. Two or more kinds of the above-mentioned concomitant drugs may be used in combination at an appropriate ratio.

When the compound of the present invention is used in combination with a concomitant drug, the amounts thereof can be increased or decreased within the safe range in consideration of the counter effect thereof. Particularly, the doses of insulin sensitizer, dipeptidyl peptidase IV inhibitor, α-glucosidase inhibitor, biguanide, insulin secretagogue, SGLT2 inhibitor and GLP-1 receptor agonist can be reduced from the general doses. Therefore, the counter effects that will be caused by these agents can be prevented safely. In addition, the doses of therapeutic agents for diabetic complications, therapeutic agents for hyperlipidemia, and antihypertensive agents can be reduced and, as a result, the counter effects that will be caused by these agents can be prevented effectively.

By combining the compound of the present invention with a concomitant drug, superior effects such as (1) decreasable dose of the compound of the present invention or a concomitant drug as compared to single administration of the compound of the present invention or a concomitant drug, (2) possible setting of a long treatment period by selecting a concomitant drug having different action and mechanism from those of the compound of the present invention, (3) possible designing of a sustained treatment effect by selecting a concomitant drug having different action and mechanism from those of the compound of the present invention, (4) a synergistic effect possibly afforded by a combined use of the compound of the present invention and a concomitant drug, and the like may be achieved.

When the compound of the present invention and a concomitant drug are used in combination, the administration time of the compound of the present invention and the concomitant drug is not restricted, and the compound of the present invention and the concomitant drug may be administered simultaneously, or may be administered at staggered times, to an administration subject. The dosage of the concomitant drug may be determined according to the dose clinically used, and can be appropriately selected depending on an administration subject, administration route, disease, combination and the like.

As the administration mode of the compound of the present invention and the concomitant drug, the following methods can be mentioned: (1) The compound of the present invention and the concomitant drug are simultaneously formulated to give a single preparation which is administered. (2) The compound of the present invention and the concomitant drug are separately formulated to give two kinds of preparations which are administered simultaneously by the same administration route. (3) The compound of the present invention and the concomitant drug are separately formulated to give two kinds of preparations which are administered by the same administration route at staggered times. (4) The compound of the present invention and the concomitant drug are separately formulated to give two kinds of preparations which are administered simultaneously by the different administration routes. (5) The compound of the present invention and the concomitant drug are separately formulated to give two kinds of preparations which are administered by the different administration routes at staggered times (e.g., the compound of the present invention and the concomitant drug are administered in this order, or in the reverse order), and the like.

EXAMPLES

The present invention is explained in detail in the following by referring to Examples, Experimental Examples and Formulation Examples. However, the examples do not limit the present invention and the present invention can be modified within the scope of the present invention.

The "room temperature" in the following Examples is generally about 10° C. to about 35° C. The ratio for a mixed solvent is, unless otherwise specified, a volume mixing ratio and % means wt % unless otherwise specified.

Elution in column chromatography in the Examples was performed under observation by TLC (Thin Layer Chromatography, thin layer chromatography) unless otherwise specified. In the observation by TLC, 60 $F_{254}$ manufactured by Merck was used as a TLC plate and the solvent used as an elution solvent in the column chromatography was used as an eluent. For detection, a UV detector was adopted. In silica gel column chromatography, the indication of NH means use of aminopropylsilane-bonded silica gel, and the indication of Diol means use of 3-(2,3-dihydroxypropoxy) propylsilane-bonded silica gel. In preparative HPLC (high performance liquid chromatography), the indication of C18 means use of octadecyl-bonded silica gel. The ratio of elution solvents is, unless otherwise specified, a volume mixing ratio.

For the analysis of $^1$H NMR, ACD/SpecManager (trade name) software and the like were used. Very mild peaks for protons of a hydroxy group, an amino group and the like may not be described.

MS was measured by LC/MS. As ionization method, ESI method or APCI method was used. The data indicates those found. Generally, molecular ion peaks are observed but may sometimes be observed as a fragment ion. In the case of a salt, generally, a molecular ion-peak or a fragment ion peak of a free form is observed.

The unit of sample concentration (c) in optical rotation ($[\alpha]_D$) is g/100 mL.

The elemental analytical value (Anal.) is shown by Calculated value (Calcd) and measured value (Found).

The peak in the powder X-ray diffraction in the Examples means a peak measured by Ultima IV (Rigaku Corporation, Japan) at room temperature using Cu Kα radiation as a radiation source. The measurement conditions were as follows.

Electric pressure/Electric current: 40 kV/50 mA
Scan speed: 6 degree/min
Scan range of 2 Theta: 2-35 degree The crystallinity by powder X-ray diffraction in the Examples was calculated by the Hermans method.

In Examples, the following abbreviations are used.
mp: melting point
MS: mass spectrum
M: mol concentration
N: normality
$CDCl_3$: deuterochloroform
DMSO-$d_6$: deuterodimethyl sulfoxide
$^1$H NMR: proton nuclear magnetic resonance
LC/MS: liquid chromatograph mass spectrometer
ESI: electrospray ionization
APCI: atmospheric pressure chemical ionization
SFC: supercritical fluid chromatography
TFA: trifluoroacetic acid
IPE: diisopropyl ether
DIPEA: N,N-diisopropylethylamine
DMF: N,N-dimethylformamide
THF: tetrahydrofuran
DME: 1,2-dimethoxyethane
MeOH: methanol
EtOH: ethanol
DMSO: dimethyl sulfoxide
NMP: 1-methylpyrrolidin-2-one
TEA: triethylamine
$Et_2O$: diethyl ether
BINAP: 1,1'-binaphthalene-2,2'-diylbis(diphenylphosphine)

Example 1

(6-((1-(5-methoxy-2-(3,3,3-trifluoropropyl)phenyl) piperidin-4-yl)methoxy)-3,4-dihydro-2H-pyrano[2,3-c]pyridin-4-yl)acetic acid A) 1-(2-(benzyloxy)-5-(methoxymethoxy)pyridin-4-yl)ethanone To a mixture of 2-(benzyloxy)-5-(methoxymethoxy)pyridine (43.93 g) and THF (400 mL) was added n-butyllithium (1.6 N hexane solution, 146 mL) at −78° C. The mixture was stirred under a nitrogen atmosphere at the same temperature for 1 hr, and N-methoxy-N-methylacetamide (36.9 g) was added. The mixture was stirred under a nitrogen atmosphere at −78° C. for 2 hr. To the mixture was added at 0° C. saturated aqueous sodium hydrogen carbonate solution, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (30.03 g). MS: [M+H]+ 288.0.

B) 1-(2-(benzyloxy)-5-(methoxymethoxy)pyridin-4-yl)-3-(dimethylamino)prop-2-en-1-one A mixture of 1-(2-(benzyloxy)-5-(methoxymethoxy)pyridin-4-yl)ethanone (23.0 g) and N,N-dimethylformamide dimethyl acetal (130 g) was stirred at 100° C. overnight, and the reaction mixture was concentrated. The residue was purified by silica gel column chromatography (NH, ethyl acetate/hexane) to give the title compound (25.38 g). MS: [M+H]+ 343.2.

C) 6-(benzyloxy)-4H-pyrano[2,3-c]pyridin-4-one

To a mixture of 1-(2-(benzyloxy)-5-(methoxymethoxy)pyridin-4-yl)-3-(dimethylamino)prop-2-en-1-one (31.8 g) and THE (300 mL) was added 6N hydrochloric acid (155 mL) at room temperature. The mixture was stirred under a nitrogen atmosphere at the same temperature for 2 hr, and the reaction mixture was concentrated. To the obtained residue was added water, and the mixture was stirred at room temperature for 30 min. The obtained precipitate was collected by filtration, washed with water and dried under reduced pressure to give the title compound (21.18 g). MS: [M+H]+ 254.0.

D) 6-(benzyloxy)-3,4-dihydro-2H-pyrano[2,3-c]pyridin-4-ol

To a mixture of 6-(benzyloxy)-4H-pyrano[2,3-c]pyridin-4-one (13.4 g) and MeOH (400 mL) were added nickel(II) chloride (6.86 g) and sodium borohydride (6.01 g) at room temperature. The mixture was stirred at the same temperature for 3 hr. To the mixture was added at 0° C. saturated aqueous ammonium chloride solution, and the mixture was concentrated under reduced pressure. The residue was extracted with ethyl acetate. The organic layer was separated, washed with saturated brine, dried over anhydrous magnesium sulfate and concentrated under reduced pressure to give the title compound (11.0 g). MS: [M+H]+ 258.1.

E) 6-(benzyloxy)-2,3-dihydro-4H-pyrano[2,3-c]pyridin-4-one

To a mixture of 6-(benzyloxy)-3,4-dihydro-2H-pyrano[2,3-c]pyridin-4-ol (11 g), TEA (19.47 g) and DMSO (250 mL) was added sulfur trioxide-pyridine complex (20.41 g) at room temperature. The mixture was stirred at room temperature for hr. To the mixture was added water, and the mixture was extracted with ethyl acetate. The organic layer was separated, washed successively with 1N hydrochloric acid, saturated aqueous sodium hydrogen carbonate solution, water and saturated brine, dried over anhydrous magnesium sulfate and concentrated under reduced pressure. The residue was washed with IPE to give the title compound (8.21 g). MS: 256.1.

F) ethyl (6-(benzyloxy)-2,3-dihydro-4H-pyrano[2,3-c]pyridine-4-ylidene)acetate To a mixture of ethyl (diethoxyphosphoryl)acetate (17.67 g) and THE (150 mL) was added sodium hydride (60% in oil, 2.52 g) at 0° C. The mixture was stirred at the same temperature for 30 min. To the mixture was added a solution of 6-(benzyloxy)-2,3-dihydro-4H-pyrano[2,3-c]pyridin-4-one (8.05 g) in THE (50 mL). The mixture was stirred under a nitrogen atmosphere at room temperature for 2 hr. To the mixture was added 1N hydrochloric acid at 0° C., and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (8.46 g). MS: [M+H]+ 326.1.

G) ethyl (6-(benzyloxy)-3,4-dihydro-2H-pyrano[2,3-c]pyridin-4-yl)acetate

To a mixture of ethyl (6-(benzyloxy)-2,3-dihydro-4H-pyrano[2,3-c]pyridine-4-ylidene)acetate (450 mg) and MeOH (8 mL) were added nickel(II) chloride (179 mg) and sodium borohydride (157 mg) at room temperature. The mixture was stirred at the same temperature for 2 hr. To the mixture was added sodium borohydride (157 mg) at room temperature. The mixture was stirred at the same temperature for 15 hr. To the mixture was added at 0° C. saturated aqueous ammonium chloride solution, and the mixture was extracted with ethyl acetate. The organic layer was separated, washed with saturated brine, dried over anhydrous magnesium sulfate and concentrated under reduced pressure to give the title compound (340 mg). MS: [M+H]+ 328.1.

H) ethyl (6-hydroxy-3,4-dihydro-2H-pyrano[2,3-c]pyridin-4-yl)acetate

A mixture of ethyl (6-(benzyloxy)-3,4-dihydro-2H-pyrano[2,3-c]pyridin-4-yl)acetate (0.5028 g) and TFA (3 mL) was stirred 60° C. for 6 hr, and the reaction mixture was concentrated. To the obtained residue was added IPE, and the precipitate was collected by filtration and washed with IPE to give the title compound (0.2812 g). MS: [M+H]+ 238.0.

I) 2-(4-(hydroxymethyl)piperidin-1-yl)-4-methoxybenzaldehyde

A mixture of 2-fluoro-4-methoxybenzaldehyde (5 g), piperidin-4-ylmethanol (4.48 g), potassium carbonate (8.97 g), and DMSO (50 mL) was stirred under a nitrogen atmosphere at 120° C. for 1 hr. To the mixture was added water at room temperature, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (7.55 g). $^1$H NMR (400 MHz, DMSO-$d_6$) δ1.37 (2H, q, J=11.8 Hz), 1.45-1.59 (1H, m), 1.77 (2H, d, J=12.4 Hz), 2.81 (2H, t, J=11.8 Hz), 3.26 (2H, d, J=11.4 Hz), 3.31-3.37 (2H, m), 3.83 (3H, s), 4.45-4.53 (1H, m), 6.61 (1H, s), 6.67 (1H, d, J=8.7 Hz), 7.66 (1H, d, J=8.4 Hz), 9.99 (1H, s).

J) 4-methoxy-2-(4-((methoxymethoxy)methyl)piperidin-1-yl)benzaldehyde

To a mixture of 2-(4-(hydroxymethyl)piperidin-1-yl)-4-methoxybenzaldehyde (4.99 g), DIPEA (10.35 g), and THE (50 mL) was-added chloromethyl methyl ether (4.83 g) at room temperature. The mixture was stirred at the same temperature for 5 hr. The mixture was added to water, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (5.2491 g). MS: [M+H]+ 294.2.

K) 4-((methoxymethoxy)methyl)-1-(5-methoxy-2-vinylphenyl)piperidine

To a mixture of methyl(triphenyl)phosphonium iodide (4.76 g) and THF (20 mL) was added potassium tert-butoxide (1.101 g) at 0° C. The mixture was stirred at room temperature for 1 hr. To the mixture was added a solution of 4-methoxy-2-(4-((methoxymethoxy)methyl)piperidin-1-yl)benzaldehyde (1.1515 g) in THF at 0° C. The mixture was stirred at room temperature for 2 hr. To the mixture was added a saturated aqueous ammonium chloride solution at 0° C., and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (1.0777 g). MS: [M+H]+ 292.2.

L) 4-((methoxymethoxy)methyl)-1-(5-methoxy-2-((1E)-3,3,3-trifluoroprop-1-en-1-yl)phenyl)piperidine To a mixture of 1-trifluoromethyl-1,2-benzoiodoxol-3(1H)-one (1.266 g) and tetrakis(acetonitrile)copper(I) hexafluorophosphate (0.249 g) was added a solution of 4-((methoxymethoxy)methyl)-1-(5-methoxy-2-vinylphenyl)piperidine (0.9731 g) in dichloromethane (20 mL) at room temperature. The mixture was stirred at the same temperature for 2 hr. The mixture was added to a saturated aqueous sodium hydrogen carbonate solution, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (0.3373 g). MS: [M+H]+ 360.2.

M) 4-((methoxymethoxy)methyl)-1-(5-methoxy-2-(3,3,3-trifluoropropyl)phenyl)piperidine A mixture of 4-((methoxymethoxy)methyl)-1-(5-methoxy-2-((1E)-3,3,3-trifluoroprop-1-en-1-yl)phenyl)piperidine (0.2888 g), 10% palladium carbon (0.05 g) and EtOH (7 mL) was stirred at normal pressure under a hydrogen atmosphere at 50° C. for 2 hr. The catalyst was filtered off and the filtrate was concentrated under reduced pressure to give the title compound (0.2668 g). MS: [M+H]+ 362.2.

N) (1-(5-methoxy-2-(3,3,3-trifluoropropyl)phenyl)piperidin-4-yl)methanol

To a mixture of 4-((methoxymethoxy)methyl)-1-(5-methoxy-2-(3,3,3-trifluoropropyl)phenyl)piperidine (0.1696 g) and MeOH (7 mL) was added 6N hydrochloric acid (1 mL) at room temperature. The mixture was stirred at 60° C. for 3 hr. The mixture was neutralized with 1N aqueous sodium hydroxide solution and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (0.1468 g). MS: [M+H]+ 318.1.

O) ethyl (6-((1-(5-methoxy-2-(3,3,3-trifluoropropyl)phenyl)piperidin-4-yl)methoxy)-3,4-dihydro-2H-pyrano[2,3-c]pyridin-4-yl)acetate A mixture of (1-(5-methoxy-2-(3,3,3-trifluoropropyl)phenyl)piperidin-4-yl)methanol (0.1395 g), ethyl (6-hydroxy-3,4-dihydro-2H-pyrano[2,3-c]pyridin-4-yl)acetate (0.125 g), (tributylphosphoranylidene)acetonitrile (0.318 g) and toluene (8 mL) was stirred at 100° C. for 3 hr. The mixture was added to water, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (0.1622 g). MS: [M+H]+ 537.4.

P) (6-((1-(5-methoxy-2-(3,3,3-trifluoropropyl)phenyl)piperidin-4-yl)methoxy)-3,4-dihydro-2H-pyrano[2,3-c]pyridin-4-yl)acetic acid To a mixture of ethyl (6-((1-(5-methoxy-2-(3,3,3-trifluoropropyl)phenyl)piperidin-4-yl)methoxy)-3,4-dihydro-2H-pyrano[2,3-c]pyridin-4-yl)acetate (0.072 g), THF (2 mL) and MeOH (2.000 mL) was added 1N aqueous sodium hydroxide solution (1.5 mL) at room temperature. The mixture was stirred at room temperature overnight. The mixture was neutralized with 1N hydrochloric acid and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (0.0587 g). $^1$H NMR (300 MHz, CDCl$_3$) δ1.43-1.59 (2H, m), 1.81-1.98 (4H, m), 2.14-2.26 (1H, m), 2.30-2.48 (2H, m), 2.53-2.74 (3H, m), 2.77-2.93 (3H, m), 3.00-3.10 (2H, m), 3.30-3.40 (1H, m), 3.78 (3H, s), 4.10-4.25 (4H, m), 6.55 (1H, s), 6.58 (1H, dd, J=8.4, 2.6 Hz), 6.69 (1H, d, J=2.6 Hz), 7.06 (1H, d, J=8.4 Hz), 7.76 (1H, s).

Example 2

(6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetic acid

A) 2-(benzyloxy)-4-bromo-5-(methoxymethoxy)pyridine

To a mixture of 2-(benzyloxy)-5-(methoxymethoxy)pyridine (3.0295 g) and THF (60 mL) was added n-butyllithium (1.6 M hexane solution, 11.58 mL) at −78° C. The mixture was stirred at the same temperature for 1 hr. 1,2-Dibromo-1,1,2,2-tetrafluoroethane (16.05 g) was added to the mixture at −78° C. The mixture was stirred at the same temperature for 2 hr. The mixture was added to a saturated aqueous sodium thiosulfate solution, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (2.6277 g). MS: [M+H]+ 324.0.

B) 6-(benzyloxy)-4-bromopyridin-3-ol

To a mixture of 2-(benzyloxy)-4-bromo-5-(methoxymethoxy)pyridine (0.8015 g) and THF (12 mL) was added 6N hydrochloric acid (6 mL) at room temperature. The mixture was stirred at the same temperature for 6 hr. The mixture was added to water, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (0.5957 g). MS: [M+H]$^+$ 280.0.

C) 2-(benzyloxy)-4-bromo-5-(2,2,3,3,3-pentafluoropropoxy)pyridine

A mixture of 6-(benzyloxy)-4-bromopyridin-3-ol (0.5751 g), 2,2,3,3,3-pentafluoropropyl trifluoromethanesulfonate (1.158 g), cesium carbonate (2.007 g) and DMF (10 mL) was stirred at room temperature overnight. The mixture was added to water, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (0.8111 g). MS: [M+H]$^+$ 412.0.

D) 4-bromo-5-(2,2,3,3,3-pentafluoropropoxy)pyridin-2(1H)-one

A mixture of 2-(benzyloxy)-4-bromo-5-(2,2,3,3,3-pentafluoropropoxy)pyridine (3.1445 g) and TEA (30 mL) was stirred at 60° C. for 5 hr, and the reaction mixture was concentrated. The residue was purified by silica gel column chromatography (ethyl acetate/hexane) to give the title compound (2.3711 g). MS: [M+H]$^+$ 322.0.

E) 4-bromo-2-methoxy-5-(2,2,3,3,3-pentafluoropropoxy)pyridine

A mixture of 4-bromo-5-(2,2,3,3,3-pentafluoropropoxy)pyridin-2(1H)-one (2.3711 g), silver(I) carbonate (3.05 g), methyl iodide (4.58 mL) and toluene (100 mL) was stirred at 60° C. for 3 hr. The mixture was filtered and the filtrate was concentrated. The residue was purified by silica gel column chromatography (ethyl acetate/hexane) to give the title compound (1.9217 g). MS: [M+H]$^+$ 336.0.

F) ethyl 1-(2-methoxy-5-(2,2,3,3,3-pentafluoropropoxy)pyridin-4-yl)piperidine-4-carboxylate A mixture of 4-bromo-2-methoxy-5-(2,2,3,3,3-pentafluoropropoxy)pyridine (0.9233 g), ethyl piperidine-4-carboxylate (0.648 g), 2'-(dicyclohexylphosphino)-N,N-dimethylbiphenyl-2-amine (0.216 g), tris(dibenzylideneacetone)dipalladium(0) (0.126 g), tripotassium phosphate (1.750 g), and DME (15 mL) was subjected to microwave irradiation at 130° C. for 3 hr. The mixture was added to water, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (0.6721 g). MS: [M+H]$^+$ 413.1.

G) (1-(2-methoxy-5-(2,2,3,3,3-pentafluoropropoxy)pyridin-4-yl)piperidin-4-yl)methanol To a mixture of ethyl 1-(2-methoxy-5-(2,2,3,3,3-pentafluoropropoxy)pyridin-4-yl)piperidine-4-carboxylate (0.6721 g) and THF (15 mL) was added lithium borohydride (0.107 g) at room temperature. The mixture was stirred at 60° C. for 3 hr. To the mixture was added saturated aqueous ammonium chloride solution at 0° C., and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (0.5358 g). MS: [M+H]$^+$ 371.1.

H) ethyl (6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetate A mixture of (1-(2-methoxy-5-(2,2,3,3,3-pentafluoropropoxy)pyridin-4-yl)piperidin-4-yl)methanol (0.1972 g), ethyl (6-hydroxy-3,4-dihydro-2H-pyrano[2,3-c]pyridin-4-yl)acetate (0.152 g), (tributylphosphoranylidene)acetonitrile (0.386 g), and toluene (10 mL) was stirred at 100° C. for 3 hr. The mixture was added to water, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (0.2310 g). MS: [M+H]$^+$ 590.4.

I) (6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetic acid To a mixture of ethyl (6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetate (0.0278 g), THF (1.5 mL) and MeOH (1.500 mL) was added 1N aqueous sodium hydroxide solution (0.6 mL) at room temperature. The mixture was stirred at the same temperature overnight. The mixture was neutralized with 1N hydrochloric acid and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (0.0184 g). H NMR (300 MHz, CDCl$_3$) δ 1.40-1.55 (2H, m), 1.81-2.01 (4H, m), 2.13-2.25 (1H, m), 2.52-2.75 (3H, m), 2.87 (1H, dd, J=16.3, 4.7 Hz), 3.28-3.40 (1H, m), 3.64-3.75 (2H, m), 3.87 (3H, s), 4.08-4.25 (4H, m), 4.31-4.43 (2H, m), 6.19 (1H, s), 6.54 (1H, s), 7.70 (1H, s), 7.74 (1H, s).

Example 3

(3-((1-(2-methoxy-5-(2,2,3,3,3-pentafluoropropoxy)pyridin-4-yl)piperidin-4-yl)methoxy)-6,7-dihydro-5H-cyclopenta[c]pyridin-5-yl)acetic acid

A) ethyl 5-(3-butoxy-3-oxoprop-1-en-1-yl)-2-methoxyisonicotinate

A mixture of ethyl 5-bromo-2-methoxyisonicotinate (11.73 g), palladium(II) acetate (1.012 g), tri-tert-butylphosphonium tetrafluoroborate (3.93 g), butyl acrylate (28.9 g), DIPEA (17.49 g) and NMP (30 mL) was stirred under a nitrogen atmosphere at 120° C. for 15 hr. To the mixture was added water, and the mixture was extracted with ethyl acetate. The organic layer was separated, washed successively with water and saturated brine, dried over anhydrous magnesium sulfate and concentrated under reduced pressure. The residue was purified by silica gel column chromatography (ethyl acetate/hexane) to give the title compound (13.3 g). MS: [M+H]$^+$ 308.1.

B) ethyl 5-(3-butoxy-3-oxopropyl)-2-methoxyisonicotinate

A mixture of ethyl 5-(3-butoxy-3-oxoprop-1-en-1-yl)-2-methoxyisonicotinate (7.54 g), 10% palladium carbon (containing 55% water, 3 g) and THF (300 mL) was stirred at normal pressure under a hydrogen atmosphere at room temperature for 15 hr. The catalyst was filtered off and the filtrate was concentrated under reduced pressure. The residue was purified by silica gel column chromatography (ethyl acetate/hexane) to give the title compound (7.08 g). MS: [M+H]$^+$ 310.1.

C) butyl 3-methoxy-5-oxo-6,7-dihydro-5H-cyclopenta[c]pyridine-6-carboxylate

To a mixture of ethyl 5-(3-butoxy-3-oxopropyl)-2-methoxyisonicotinate (10.8 g) and THE (500 mL) was added sodium hydride (60% in oil, 1.676 g) at 0° C. The mixture was stirred at 60° C. for 20 hr. To the mixture was added 0.5N hydrochloric acid (100 mL) at 0° C. To the mixture was added water, and the mixture was extracted with ethyl acetate. The organic layer was separated, washed successively with water and saturated brine, dried over anhydrous magnesium sulfate and concentrated under reduced pressure. The residue was purified by silica gel column chromatography (ethyl acetate/hexane) to give the title compound (7.49 g). The obtained compound was used for the next step without further purification.

D) 3-methoxy-6,7-dihydro-5H-cyclopenta[c]pyridin-5-one

A mixture of butyl 3-methoxy-5-oxo-6,7-dihydro-5H-cyclopenta[c]pyridine-6-carboxylate (7.76 g), DMSO (180 mL) and water (20 mL) was stirred at 150° C. for 1 hr. The mixture was cooled to room temperature, water was added, and the mixture was extracted with ethyl acetate. The organic layer was separated, washed successively with water and saturated brine, dried over anhydrous magnesium sulfate and concentrated under reduced pressure. The residue was purified by silica gel column chromatography (ethyl acetate/hexane) to give the title compound (4.44 g). MS: [M+H]$^+$ 164.0.

E) ethyl (3-methoxy-6,7=dihydro-5H-cyclopenta[c]pyridin-5-ylidene)acetate

To a mixture of sodium hydride (60% in oil, 1.405 g) and toluene (150 mL) was added ethyl (diethoxyphosphoryl)acetate (7.87 g) at 0° C. The mixture was stirred at 0° C. for 30 min and a solution of 3-methoxy-6,7-dihydro-5H-cyclopenta[c]pyridin-5-one (3.82 g) in toluene (30 mL) was added. The mixture was stirred at room temperature for 15 hr. To the mixture was added water, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (4.67 g) as an E/Z mixture. The obtained compound was used in the next step without purification.

F) ethyl (3-methoxy-6,7-dihydro-5H-cyclopenta[c]pyridin-5-yl)acetate

A mixture of ethyl (3-methoxy-6,7-dihydro-5H-cyclopenta[c]pyridin-5-ylidene)acetate (E/Z mixture) (4.67 g), 10% palladium carbon (2 g) and THF (200 mL) was stirred at normal pressure under a hydrogen atmosphere at room temperature for 3 hr. The catalyst was filtered off and the filtrate was concentrated under reduced pressure. The residue was purified by silica gel column chromatography (ethyl acetate/hexane) to give the title compound (4.46 g). MS: [M+H]$^+$ 236.1.

G) ethyl (3-hydroxy-6,7-dihydro-5H-cyclopenta[c]pyridin-5-yl)acetate

A mixture of ethyl (3-methoxy-6,7-dihydro-5H-cyclopenta[c]pyridin-5-yl)acetate (2.47 g), pyridine hydrochloride (12.13 g) and DMF (20 mL) was stirred at 120° C. for 2.5 hr, and the reaction mixture was concentrated. To the residue was added toluene and the mixture was concentrated. The residue was neutralized with saturated aqueous sodium hydrogen carbonate solution and concentrated under reduced pressure. To the obtained solid was added THF (100 mL) and the mixture was stirred at room temperature for 30 min. The mixture was filtered and the filtrate was concentrated. The residue was purified by silica gel column chromatography (ethyl acetate/MeOH) to give the title compound (2.04 g). MS: [M+H]+ 222.1.

H) ethyl (3-((1-(2-methoxy-5-(2,2,3,3,3-pentafluoropropoxy)pyridin-4-yl)piperidin-4-yl)methoxy)-6,7-dihydro-5H-cyclopenta[c]pyridin-5-yl)acetate A mixture of (1-(2-methoxy-5-(2,2,3,3,3-pentafluoropropoxy)pyridin-4-yl)piperidin-4-yl)methanol (0.0296 g), ethyl (3-hydroxy-6,7-dihydro-5H-cyclopenta[c]pyridin-5-yl)acetate (0.027 g), (tributylphosphoranylidene)acetonitrile (0.058 g) and toluene (3 mL) was stirred at 100° C. overnight. The mixture was added to water, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (0.0295 g). MS: [M+H]$^+$ 574.4.

I) (3-((1-(2-methoxy-5-(2,2,3,3,3-pentafluoropropoxy)pyridin-4-yl)piperidin-4-yl)methoxy)-6,7-dihydro-5H-cyclopenta[c]pyridin-5-yl)acetic acid To a mixture of ethyl (3-((1-(2-methoxy-5-(2,2,3,3,3-pentafluoropropoxy)pyridin-4-yl)piperidin-4-yl)methoxy)-6,7-dihydro-5H-cyclopenta[c]pyridin-5-yl)acetate (0.0295 g), THE (1.5 mL) and MeOH (1.500 mL) was added 1N aqueous sodium hydroxide solution (0.6 mL) at room temperature. The mixture was stirred at the same temperature overnight. The mixture was neutralized with 1N hydrochloric acid and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (0.0241 g). $^1$H NMR (300 MHz, CDCl$_3$) δ1.41-1.58 (2H, m), 1.70-1.87 (1H, m), 1.89-2.06 (3H, m), 2.38-2.58 (2H, m), 2.63-2.96 (5H, m), 3.47-3.60 (1H, m), 3.66-3.76 (2H, m), 3.87 (3H, s), 4.16 (2H, d, J=6.3 Hz), 4.31-4.43 (2H, m), 6.20 (1H, s), 6.60 (1H, s), 7.70 (1H, s), 7.98 (1H, d, J=0.8 Hz).

Example 4

(3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetic acid A) ethyl 1-(2-bromo-5-methoxyphenyl)piperidine-4-carboxylate A mixture of 1-bromo-2-iodo-4-methoxybenzene (15.03 g), ethyl piperidine-4-carboxylate (8.31 g), palladium(II) acetate (0.539 g), BINAP (1.794 g), cesium carbonate (23.47 g) and xylene (150 mL) was stirred under an argon atmosphere at 130° C. overnight and at 100° C. for 20 hr. The reaction mixture was filtered and the filtrate was concentrated. To the residue was added water at room temperature and the mixture was extracted with ethyl acetate. The organic layer was separated, washed with aqueous citric acid solution and saturated brine, dried over anhydrous magnesium sulfate and concentrated under reduced pressure. The residue was purified by silica gel column chromatography (ethyl acetate/hexane) to give the title compound (4.38 g). $^1$H NMR (300 MHz, CDCl$_3$) δ1.28 (3H, t, J=7.1 Hz), 1.90-2.08 (4H, m), 2.43 (1H, tt, J=10.2, 5.1 Hz), 2.60-2.74 (2H, m), 3.35 (2H, dt, J=11.8, 3.1 Hz), 3.78 (3H, s), 4.17 (2H, q, J=7.1 Hz), 6.46 (1H, dd, J=8.7, 2.9 Hz), 6.59 (1H, d, J=2.9 Hz), 7.43 (1H, d, J=8.7 Hz).

B) tert-butyl 4-(2-(4-(ethoxycarbonyl)piperidin-1-yl)-4-methoxyphenyl)-3,6-dihydropyridine-1(2H)-carboxylate A mixture of ethyl 1-(2-bromo-5-methoxyphenyl)piperidine-4-carboxylate (1.507 g), (1-(tert-butoxycarbonyl)-1,2,3,6-tetrahydropyridin-4-yl)boronic acid (2 g), [1,1'-bis(diphenylphosphino)ferrocene]palladium(II) dichloride (0.322 g), 2 M aqueous sodium carbonate solution (4.84 mL) and DMF (30 mL) was stirred under a nitrogen atmosphere at 100° C. for 2 hr. To the mixture was added water at room temperature and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (1.63 g). $^1$H NMR (300 MHz, CDCl$_3$) δ1.27 (3H, t, J=7.1 Hz), 1.50 (9H, s), 1.69-1.87 (2H, m), 1.91-2.02 (2H, m), 2.36 (1H, tt, J=11.2, 4.0 Hz), 2.52-2.68 (4H, m), 3.32 (2H, d, J=12.0 Hz), 3.59 (2H, t, J=5.6 Hz), 3.79 (3H, s), 4.03 (2H, d, J=2.5 Hz), 4.15 (2H, q, J=7.2 Hz), 5.68 (1H, s), 6.47-6.58 (2H, m), 7.01 (1H, d, J=8.1 Hz).

C) tert-butyl 4-(2-(4-(ethoxycarbonyl)piperidin-1-yl)-4-methoxyphenyl)piperidine-1-carboxylate A mixture of tert-butyl 4-(2-(4-(ethoxycarbonyl)piperidin-1-yl)-4-methoxyphenyl)-3,6-dihydropyridine-1(2H)-carboxylate (1.63 g), 10% palladium carbon (800 mg) and THF (50 mL) was stirred at normal pressure under a hydrogen atmosphere at room temperature overnight. The catalyst was filtered off and the filtrate was concentrated under reduced pressure to give the title compound (1.57 g). H NMR (300 MHz, CDCl$_3$) δ1.25-1.32 (3H, m), 1.49 (9H, s), 1.48-1.63 (2H, m), 1.64-1.75 (2H, m), 1.79-2.08 (4H, m), 2.32-2.50 (1H, m), 2.68 (2H, td, J=11.4, 2.5 Hz), 2.79 (2H, t, J=12.3 Hz), 2.96-3.16 (3H, m), 3.78 (3H, s), 4.07-4.32 (4H, m), 6.58-6.67 (2H, m), 7.08 (1H, d, J=8.3 Hz).

D) ethyl 1-(5-methoxy-2-(1-(2,2,2-trifluoroethyl)piperidin-4-yl)phenyl)piperidine-4-carboxylate To a mixture of tert-butyl 4-(2-(4-(ethoxycarbonyl)piperidin-1-yl)-4-methoxyphenyl)piperidine-1-carboxylate (518 mg) and EtOAc (3 mL) was added 4N hydrogen chloride ethyl acetate solution (4 mL) at room temperature. The mixture was stirred under a nitrogen atmosphere at room temperature for 20 min and the reaction mixture was concentrated. To a mixture of the obtained residue, TEA (1174 mg) and acetonitrile (5 mL) was added 2,2,2-trifluoroethyl trifluoromethanesulfonate (1346 mg) at room temperature. The mixture was stirred under a nitrogen atmosphere at 60° C. for 20 min, and the reaction mixture was concentrated. The residue was purified by silica gel column chromatography (ethyl acetate/hexane) to give the title compound (448.2 mg). $^1$H NMR (400 MHz, CDCl$_3$) δ1.29 (3H, t, J=6.7 Hz), 1.63-1.82 (4H, m), 1.89 (2H, q, J=11.9 Hz), 1.97-2.06 (2H, m), 2.34-2.52 (3H, m), 2.67 (2H, t, J=11.4 Hz), 2.88-3.15 (7H, m), 3.78 (3H, s), 4.15-4.24 (2H, m), 6.60-6.67 (2H, m), 7.16 (1H, d, J=8.0 Hz).

E) (1-(5-methoxy-2-(1-(2,2,2-trifluoroethyl)piperidin-4-yl)phenyl)piperidin-4-yl)methanol To a mixture of lithium aluminum hydride (161 mg) and Et$_2$O (5 mL) was added a solution of ethyl 1-(5-methoxy-2-(1-(2,2,2-trifluoroethyl)piperidin-4-yl)phenyl)piperidine-4-carboxylate (604.9 mg) in diethyl ether at 0° C. The mixture was stirred under a nitrogen atmosphere at 0° C. for 20 min. To the mixture were added water and aqueous sodium hydroxide solution, and the obtained precipitate was removed by filtration. The filtrate was concentrated under reduced pressure to give the title compound (527.4 mg). $^1$H NMR (300 MHz, DMSO-d$_6$) δ1.22-1.37 (2H, m), 1.38-1.53 (1H, m), 1.53-1.70 (4H, m), 1.75 (2H, d, J=12.4 Hz), 2.40 (2H, td, J=10.7, 3.9 Hz), 2.53-2.64 (2H, m), 2.75-2.96 (3H, m), 3.02 (2H, d, J=11.5 Hz), 3.17 (2H, q, J=10.3 Hz), 3.29-3.34 (2H, m), 3.70 (3H, s), 4.45 (1H, t, J=5.3 Hz), 6.54-6.64 (2H, m), 7.12 (1H, d, J=9.2 Hz).

F) ethyl (3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetate To a mixture of (1-(5-methoxy-2-(1-(2,2,2-trifluoroethyl)piperidin-4-yl)phenyl)piperidin-4-yl)methanol (178 mg), ethyl (3-hydroxy-6,7-dihydro-5H-cyclopenta[c]pyridin-5-yl)acetate (102 mg) and toluene (3 mL) was added (tributylphosphoranylidene)acetonitrile (222 mg) at room temperature. The mixture was stirred under a nitrogen atmosphere at 100° C. for 3 hr. The mixture was purified by silica gel column chromatography (ethyl acetate/hexane) to give the title compound (174.9 mg). H NMR (300 MHz, CDCl$_3$) δ1.28 (3H, t, J=7.2 Hz), 1.41-1.60 (2H, m), 1.65-1.84 (5H, m), 1.86-2.02 (3H, m), 2.32-2.53 (4H, m), 2.61-

3.16 (12H, m), 3.43-3.59 (1H, m), 3.78 (3H, s), 4.07-4.25 (4H, m), 6.58 (1H, s), 6.62 (1H, dd, J=8.5, 2.6 Hz), 6.67 (1H, d, J=2.6 Hz), 7.15 (1H, d, J=8.5 Hz), 7.97 (1H, d, J=0.8 Hz).

G) (3-((1-(5-methoxy-2-(1-(2,2,2-trifluoroethyl) piperidin-4-yl)phenyl)piperidin-4-yl)methoxy)-6,7-dihydro-5H-cyclopenta[c]pyridin-5-yl)acetic acid To a mixture of ethyl (3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetate (39 mg), THF (1 mL) and MeOH (0.500 mL) was added 1N aqueous sodium hydroxide solution (1 mL) at room temperature. The mixture was stirred at 60° C. for 30 min. The mixture was neutralized with 1N hydrochloric acid at room temperature and extracted with ethyl acetate. The organic layer was separated, washed with water and saturated brine, dried over anhydrous magnesium sulfate and concentrated under reduced pressure. The obtained solid was crystallized from ethyl acetate/hexane to give the title compound (28 mg). $^1$H NMR (300 MHz, DMSO-$d_6$) δ1.35-1.52 (2H, m), 1.53-1.75 (4H, m), 1.77-1.96 (3H, m), 2.22-2.47 (4H, m), 2.63 (2H, t, J=11.0 Hz), 2.70-3.08 (8H, m), 3.17 (2H, q, J=10.3 Hz), 3.29-3.46 (2H, m), 3.70 (3H, s), 4.14 (2H, d, J=6.2 Hz), 6.56-6.65 (2H, m), 6.68 (1H, s), 7.13 (1H, d, J=9.0 Hz), 7.96 (1H, s), 12.35 (1H, brs).

Example 5

(6-((1-(2-methoxy-5-(1-(2,2,2-trifluoroethyl)piperidin-4-yl)pyridin-4-yl)piperidin-4-yl)methoxy)-3,4-dihydro-2H-pyrano[2,3-c]pyridin-4-yl)acetic acid A) tert-butyl 4-(((4-(2-ethoxy-2-oxoethyl)-3,4-dihydro-2H-pyrano[2,3-c]pyridin-6-yl)oxy)methyl) piperidine-1-carboxylate A mixture of tert-butyl 4-(hydroxymethyl)piperidine-1-carboxylate (2.005 g), ethyl (6-hydroxy-3,4-dihydro-2H-pyrano[2,3-c]pyridin-4-yl)acetate (1.7 g), (tributylphosphoranylidene)acetonitrile (3.46 g) and toluene (20 mL) was stirred at 100° C. overnight. The reaction mixture was added to water, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (2.36 g). MS: [M+H]$^+$ 435.2.

B) ethyl (6-(piperidin-4-ylmethoxy)-3,4-dihydro-2H-pyrano[2,3-c]pyridin-4-yl)acetate To a mixture of tert-butyl 4-(((4-(2-ethoxy-2-oxoethyl)-3,4-dihydro-2H-pyrano[2,3-c]pyridin-6-yl)oxy)methyl)piperidine-1-carboxylate (0.4104 g) and toluene (5 mL) was added TFA (3 mL) at room temperature, and the mixture was stirred at the same temperature for 1 hr. The reaction mixture was concentrated, and the residue was diluted with ethyl acetate. Saturated aqueous sodium hydrogen carbonate solution was added and the mixture was extracted with ethyl acetate. The organic layer was separated, washed with saturated brine, dried over anhydrous magnesium sulfate and concentrated under reduced pressure to give the title compound (0.3324 g). MS: [M+H]$^+$ 335.2.

C) ethyl (6-((1-(5-bromo-2-methoxypyridin-4-yl) piperidin-4-yl)methoxy)-3,4-dihydro-2H-pyrano[2,3-c]pyridin-4-yl)acetate A mixture of 5-bromo-4-chloro-2-methoxypyridine (416 mg), ethyl (6-(piperidin-4-ylmethoxy)-3,4-dihydro-2H-pyrano[2,3-c]pyridin-4-yl)acetate (938 mg), potassium carbonate (775 mg) and DMSO (10 mL) was stirred at 100° C. for 40 hr. The reaction mixture was added to water, and the mixture was extracted with ethyl acetate. The organic layer was separated, washed successively with water and saturated brine, dried over anhydrous magnesium sulfate and concentrated under reduced pressure. The residue was purified by silica gel column chromatography (ethyl acetate/hexane) to give the title compound (396.0 mg). MS: [M+H]$^+$ 520.1.

D) tert-butyl 4-(4-(((4-(2-ethoxy-2-oxoethyl)-3,4-dihydro-2H-pyrano[2,3-c]pyridin-6-yl)oxy)methyl) piperidin-1-yl)-6-methoxy-3',6'-dihydro-3,4'-bipyridine-1'(2'H)-carboxylate A mixture of ethyl (6-((1-(5-bromo-2-methoxypyridin-4-yl)piperidin-4-yl)methoxy)-3,4-dihydro-2H-pyrano[2,3-c] pyridin-4-yl)acetate (396.0 mg), tert-butyl 4-(4,4,5,5-tetramethyl-1,3,2-dioxaborolan-2-yl)-3,6-dihydropyridine-1 (2H)-carboxylate (353 mg), 2 M aqueous sodium carbonate solution (0.761 mL), [1,1'-bis(diphenylphosphino)ferrocene]palladium(II) dichloride dichloromethane adduct (62.1 mg) and DME (2.5 mL) was subjected to microwave irradiation at 130° C. for 40 min under a nitrogen atmosphere. The reaction mixture was added to water, and the mixture was extracted with ethyl acetate. The organic layer was separated, washed successively with water and saturated brine, dried over anhydrous magnesium sulfate and concentrated under reduced pressure. The residue was purified by silica gel column chromatography (ethyl acetate/hexane) to give the title compound (379.3 mg). MS: [M+H]$^+$ 623.2.

E) tert-butyl 4-(4-(4-(((4-(2-ethoxy-2-oxoethyl)-3,4-dihydro-2H-pyrano[2,3-c]pyridin-6-yl)oxy)methyl) piperidin-1-yl)-6-methoxypyridin-3-yl)piperidine-1-carboxylate A mixture of tert-butyl 4-(4-(((4-(2-ethoxy-2-oxoethyl)-3,4-dihydro-2H-pyrano[2,3-c]pyridin-6-yl)oxy)methyl)piperidin-1-yl)-6-methoxy-3',6'-dihydro-3,4'-bipyridine-1' (2'H)-carboxylate (379.3 mg), 10% palladium carbon (64.8 mg) and EtOH (4 mL) was stirred at normal pressure under a hydrogen atmosphere at room temperature overnight and at 50° C. for 1.5 hr. The catalyst was filtered off and the filtrate was concentrated under reduced pressure to give the title compound. The obtained compound was used for the next step without further purification. MS: [M+H]$^+$ 625.2.

F) ethyl (6-((1-(2-methoxy-5-(piperidin-4-yl)pyridin-4-yl)piperidin-4-yl)methoxy)-3,4-dihydro-2H-pyrano[2,3-c]pyridin-4-yl)acetate hydrochloride A mixture of tert-butyl 4-(4-(4-(((4-(2-ethoxy-2-oxoethyl)-3,4-dihydro-2H-pyrano[2,3-c]pyridin-6-yl)oxy) methyl)piperidin-1-yl)-6-methoxypyridin-3-yl)piperidine-1-carboxylate obtained in step (E) and 4 M hydrogen chloride ethyl acetate solution (0.5 mL) was stirred at room temperature for 4 hr, and the reaction mixture was concentrated to give the title compound. The obtained compound was used for the next step without further purification.

G) ethyl (6-((1-(2-methoxy-5-(1-(2,2,2-trifluoroethyl)piperidin-4-yl)pyridin-4-yl)piperidin-4-yl)methoxy)-3,4-dihydro-2H-pyrano[2,3-c]pyridin-4-yl)acetate A mixture of ethyl (6-((1-(2-methoxy-5-(piperidin-4-yl)pyridin-4-yl)piperidin-4-yl)methoxy)-3,4-dihydro-2H-pyrano[2,3-c]pyridin-4-yl)acetate hydrochloride obtained in step (F), 2,2,2-trifluoroethyl trifluoromethanesulfonate (0.175 mL), potassium carbonate (253 mg) and DMF (3 mL) was stirred at 80° C. for 4 hr. The reaction mixture was added to water, and the mixture was extracted with ethyl acetate. The organic layer was separated, washed successively with water and saturated brine, dried over anhydrous magnesium sulfate and concentrated under reduced pressure. The residue was separated by silica gel column chromatography (ethyl acetate/hexane) and then HPLC (C18, mobile phase:water/acetonitrile (containing 0.1% TFA)), to the obtained fraction was added saturated aqueous sodium hydrogen carbonate solution, and the mixture was extracted with ethyl acetate. The extract was dried over anhydrous magnesium sulfate and concentrated under reduced pressure to give the title compound (175.3 mg). MS: [M+H]$^+$ 607.2.

H) (6-((1-(2-methoxy-5-(1-(2,2,2-trifluoroethyl)piperidin-4-yl)pyridin-4-yl)piperidin-4-yl)methoxy)-3,4-dihydro-2H-pyrano[2,3-c]pyridin-4-yl)acetic acid To a mixture of ethyl (6-((1-(2-methoxy-5-(1-(2,2,2-trifluoroethyl)piperidin-4-yl)pyridin-4-yl)piperidin-4-yl)methoxy)-3,4-dihydro-2H-pyrano[2,3-c]pyridin-4-yl)acetate (175.3 mg), EtOH (1.000 mL) and THF (1 mL) was added 2N aqueous sodium hydroxide solution (0.5 mL) at room temperature. The mixture was stirred at room temperature for 3 hr and concentrated under reduced pressure. To the residue was added water and the mixture was neutralized with 2N hydrochloric acid and the obtained solid was collected to give the title compound (142.6 mg). $^1$H NMR (300 MHz, DMSO-d$_6$) δ1.31-1.52 (2H, m), 1.58-1.93 (8H, m), 1.96-2.11 (1H, m), 2.32-2.70 (6H, m), 2.81 (1H, dd, J=16.2, 5.0 Hz), 2.97-3.27 (7H, m), 3.78 (3H, s), 4.00-4.22 (4H, m), 6.31 (1H, s), 6.70 (1H, s), 7.66 (1H, s), 7.93 (1H, s), 12.35 (1H, s).

Example 6

(6-((1-(2-methoxy-5-(1-(2,2,2-trifluoroethyl)piperidin-4-yl)pyridin-4-yl)piperidin-4-yl)methoxy)-3,4-dihydro-2H-pyrano[2,3-c]pyridin-4-yl)acetic acid (Optical Isomer)

A racemate (120 mg) of (6-((1-(2-methoxy-5-(1-(2,2,2-trifluoroethyl)piperidin-4-yl)pyridin-4-yl)piperidin-4-yl)methoxy)-3,4-dihydro-2H-pyrano[2,3-c]pyridin-4-yl)acetic acid was separated by SFC (column: CHIRALPAK IA (trade name), 20 mm ID×250 mm L, manufactured by Daicel Corporation, mobile phase: carbon dioxide/methanol=660/340) and the title compound (37.1 mg) with smaller retention time was obtained. $^1$H NMR (300 MHz, CDCl$_3$) δ1.41-1.63 (2H, m), 1.69-2.03 (8H, m), 2.17-2.27 (1H, m), 2.39-2.74 (6H, m), 2.87 (1H, dd, J=16.1, 4.6 Hz), 2.98-3.22 (6H, m), 3.28-3.44 (1H, m), 3.90 (3H, s), 4.06-4.27 (4H, m), 6.31 (1H, s), 6.58 (1H, s), 7.76 (1H, s), 7.96 (1H, s).

Example 7

(6-((1-(2-methoxy-5-(1-(2,2,2-trifluoroethyl)piperidin-4-yl)pyridin-4-yl)piperidin-4-yl)methoxy)-3,4-dihydro-2H-pyrano[2,3-c]pyridin-4-yl)acetic acid (Optical Isomer)

A racemate (120 mg) of (6-((1-(2-methoxy-5-(1-(2,2,2-trifluoroethyl)piperidin-4-yl)pyridin-4-yl)piperidin-4-yl)methoxy)-3,4-dihydro-2H-pyrano[2,3-c]pyridin-4-yl)acetic acid was separated by SFC (column:CHIRALPAK IA (trade name), 20 mm ID×250 mm L, manufactured by Daicel Corporation, mobile phase: carbon dioxide/methanol=660/340) and the title compound (32.7 mg) with longer retention time was obtained. $^1$H NMR (300 MHz, CDCl$_3$) δ1.42-1.62 (2H, m), 1.70-2.01 (8H, m), 2.21 (1H, brs), 2.38-2.76 (6H, m), 2.87 (1H, dd, J=16.1, 4.5 Hz), 2.98-3.22 (6H, m), 3.37 (1H, dd, J=9.1, 4.8 Hz), 3.90 (3H, s), 4.11-4.28 (4H, m), 6.31 (1H, s), 6.58 (1H, s), 7.76 (1H, s), 7.96 (1H, s).

Example 8

(6-((1-(5-methoxy-2-(3,3,3-trifluoropropyl)phenyl)piperidin-4-yl)methoxy)-3,4-dihydro-2H-pyrano[2,3-c]pyridin-4-yl)acetic acid (Optical Isomer)

To a mixture of ethyl (6-((1-(5-methoxy-2-(3,3,3-trifluoropropyl)phenyl)piperidin-4-yl)methoxy)-3,4-dihydro-2H-pyrano[2,3-c]pyridin-4-yl)acetate (optical isomer) (0.0752 g) which is an optical isomer having longer retention time and obtained by separating a racemate of ethyl (6-((1-(5-methoxy-2-(3,3,3-trifluoropropyl)phenyl)piperidin-4-yl)methoxy)-3,4-dihydro-2H-pyrano[2,3-c]pyridin-4-yl)acetate by SFC (column: CHIRALCEL OJH (trade name), 20 mm ID×250 mm L, manufactured by Daicel Corporation, mobile phase: carbon dioxide/MeOH=880/120), THF (2.5 mL) and MeOH (2.500 mL) was added 1N aqueous sodium hydroxide solution (1.5 mL) at room temperature. The mixture was stirred at the same temperature overnight. The mixture was neutralized with 1N hydrochloric acid and extracted with ethyl acetate. The organic layer was separated, washed with saturated brine, dried over anhydrous magnesium sulfate and concentrated under reduced pressure. The residue was suspended in a mixed solvent of IPE and hexane and the precipitate was collected by filtration, washed with a mixed solvent of IPE and hexane, and dried under reduced pressure to give the title compound (0.0676 g). $^1$H NMR (300 MHz, CDCl$_3$) δ1.43-1.59 (2H, m), 1.82-1.98 (4H, m), 2.14-2.27 (1H, m), 2.31-2.49 (2H, m), 2.54-2.74 (3H, m), 2.78-2.94 (3H, m), 3.01-3.10 (2H, m), 3.30-3.41 (1H, m), 3.78 (3H, s), 4.08-4.25 (4H, m), 6.55 (1H, s), 6.59 (1H, dd, J=8.3, 2.6 Hz), 6.69 (1H, d, J=2.6 Hz), 7.06 (1H, d, J=8.3 Hz), 7.76 (1H, s).

Example 9

(6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (Optical Isomer)

A) ethyl (6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetate To a mixture of (1-(5-methoxy-2-(1-(2,2,2-trifluoroethyl)piperidin-4-yl)phenyl)piperidin-4-yl)methanol (266 mg), ethyl (6-hydroxy-3,4-dihydro-2H-pyrano[2,3-c]pyridin-4-yl)acetate (136 mg) and toluene (3 mL) was added (tributylphosphoranylidene)acetonitrile (277 mg) at room temperature. The mixture was stirred under a nitrogen atmosphere at 100° C. overnight and the reaction mixture was concentrated. The residue was purified by silica gel column chromatography (ethyl acetate/hexane) to give the title compound (213.3 mg). H NMR (300 MHz, CDCl$_3$) δ1.28 (3H, t, J=7.2 Hz), 1.40-1.58 (2H, m), 1.62-2.00 (8H, m), 2.09-2.24 (1H, m), 2.38-2.58 (3H, m), 2.67 (2H, t, J=10.9 Hz), 2.80 (1H, dd, J=15.8, 4.9 Hz), 2.87-3.15 (7H, m), 3.28-3.41 (1H, m), 3.78 (3H, s), 4.07-4.26 (6H, m), 6.54 (1H, s), 6.62 (1H, dd, J=8.4, 2.6 Hz), 6.67 (1H, d, J=2.6 Hz), 7.15 (1H, d, J=8.5 Hz), 7.75 (1H, s).

B) (6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (Optical Isomer)

To a mixture of ethyl (6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetate (55.4 mg) which is an optical isomer having longer retention time and obtained by separating a racemate of ethyl (6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetate by HPLC (column: CHIRALPAK IC (trade name), 50 mm ID×500 mm L, manufactured by Daicel Corporation, mobile phase: hexane/2-propanol=600/400), MeOH (1.000 mL) and THF (2 mL) was added 1N sodium hydroxide (2 mL) at room temperature. The mixture was stirred at 60° C. for 20 min. The mixture was neutralized with 1N hydrochloric acid at room temperature and extracted with ethyl acetate. The organic layer was separated, washed with water and saturated brine, dried over anhydrous magnesium sulfate and concentrated under reduced pressure. The obtained solid was crystallized from ethyl acetate/hexane to give the title compound (42.8 mg). $^1$H NMR (400 MHz, DMSO-d$_6$) δ1.30-1.49 (2H, m), 1.54-1.71 (4H, m), 1.71-1.92 (4H, m), 1.95-2.12 (1H, m), 2.29-2.49 (3H, m), 2.63 (2H, t, J=11.5 Hz), 2.74-2.98 (4H, m), 3.02 (2H, d, J=10.9 Hz), 3.11-3.25 (3H, m), 3.70 (3H, s), 3.99-4.23 (4H, m), 6.56-6.66 (2H, m), 6.70 (1H, s), 7.13 (1H, d, J=7.7 Hz), 7.66 (1H, s), 12.35 (1H, brs).

Example 10

(3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetic acid (Optical Isomer)

To a mixture of ethyl (3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetate (61.6 mg) which is an optical isomer having shorter retention time and obtained by separating a racemate of ethyl (3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetate by HPLC (column: CHIRALPAK IC (trade name), 50 mm ID×500 mm L, manufactured by Daicel Corporation, mobile phase: hexane/2-propanol=600/400), MeOH (1 mL) and THF (2 mL) was added 1N aqueous sodium hydroxide solution (2 mL) at room temperature. The mixture was stirred at 60° C. for 30 min. The mixture was neutralized with 1N hydrochloric acid at room temperature and extracted with ethyl acetate. The organic layer was separated, washed with water and saturated brine, dried over anhydrous magnesium sulfate and concentrated under reduced pressure. The obtained residue was crystallized from ethyl acetate/hexane to give the title compound (43.6 mg).

Example 11

(6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetic acid (Optical Isomer)

To a mixture of ethyl (6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetate (0.1150 g) which is an optical isomer having longer retention time and obtained by separating a racemate of ethyl (6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetate by SFC (column: CHIRALPAK IA (trade name), 20 mm ID×250 mm L, manufactured by Daicel Corporation, mobile phase: carbon dioxide/MeOH=860/140), THF (3 mL) and MeOH (3.00 mL) was added 1N aqueous sodium hydroxide solution (2 mL) at room temperature. The mixture was stirred at the same temperature overnight. The mixture was neutralized with 1N hydrochloric acid and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (0.1005 g). $^1$H NMR (300 MHz, CDCl$_3$) δ1.40-1.55 (2H, m), 1.82-2.01 (4H, m), 2.14-2.25 (1H, m), 2.53-2.75 (3H, m), 2.87 (1H, dd, J=16.2, 4.7 Hz), 3.29-3.40 (1H, m), 3.65-3.74 (2H, m), 3.87 (3H, s), 4.07-4.25 (4H, m), 4.31-4.42 (2H, m), 6.19 (1H, s), 6.55 (1H, s), 7.70 (1H, s), 7.75 (1H, s).

Example 17

(6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetic acid (Optical Isomer)

To a mixture of ethyl (6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetate (0.1300 g) which is an optical isomer having shorter retention time and obtained by separating a racemate of ethyl (6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetate by SFC (column: CHIRALPAK IA (trade name), 20 mm ID×250 mm L, manufactured by Daicel Corporation, mobile phase: carbon dioxide/MeOH=860/140), THF (3 mL) and MeOH (3.00 mL) was added 1N aqueous sodium hydroxide solution (2.5 mL) at room temperature. The mixture was stirred at the same temperature overnight. The mixture was neutralized with 1N hydrochloric acid and extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (0.1182 g). $^1$H NMR (300 MHz, CDCl$_3$)

δ1.38-1.56 (2H, m), 1.81-2.02 (4H, m), 2.14-2.26 (1H, m), 2.53-2.75 (3H, m), 2.88 (1H, dd, J=16.2, 4.7 Hz), 3.29-3.40 (1H, m), 3.65-3.74 (2H, m), 3.87 (3H, s), 4.07-4.25 (4H, m), 4.31-4.42 (2H, m), 6.19 (1H, s), 6.55 (1H, s), 7.71 (1H, s), 7.75 (1H, s).

Example 18

(6-((1-(5-methoxy-2-(3,3,3-trifluoropropyl)phenyl) piperidin-4-yl)methoxy)-3,4-dihydro-2H-pyrano[2,3-c]pyridin-4-yl)acetic acid (Optical Isomer)

To a mixture of ethyl (6-((1-(5-methoxy-2-(3,3,3-trifluoropropyl)phenyl)piperidin-4-yl)methoxy)-3,4-dihydro-2H-pyrano[2,3-c]pyridin-4-yl)acetate (0.0716 g) which is an optical isomer having shorter retention time and obtained by separating a racemate of ethyl (6-((1-(5-methoxy-2-(3,3,3-trifluoropropyl)phenyl)piperidin-4-yl)methoxy)-3,4-dihydro-2H-pyrano[2,3-c]pyridin-4-yl)acetate by SFC (column: CHIRALCEL OJH (trade name), 20 mm ID×250 mm L, manufactured by Daicel Corporation, mobile phase: carbon dioxide/MeOH=880/120), THF (2.5 mL) and MeOH (2.500 mL) was added 1N aqueous sodium hydroxide solution (1.5 mL) at room temperature. The mixture was stirred at the same temperature overnight. The mixture was neutralized with 1N hydrochloric acid and extracted with ethyl acetate. The organic layer was separated, washed with saturated brine, dried over anhydrous magnesium sulfate and concentrated under reduced pressure. The residue was suspended in a mixed solvent of IPE and hexane. The precipitate was collected by filtration, washed with a mixed solvent of IPE and hexane and dried under reduced pressure to give the title compound (0.0597 g).

Example 28

(6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (Optical Isomer)

To a mixture of ethyl (6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetate (56.2 mg) which is an optical isomer having shorter retention time and obtained by separating a racemate of ethyl (6-((1-(5-methoxy-2-(1-(2,2,2-trifluoroethyl)piperidin-4-yl)phenyl) piperidin-4-yl)methoxy)-3,4-dihydro-2H-pyrano[2,3-c] pyridin-4-yl)acetate by HPLC (column: CHIRALPAK IC (trade name), 50 mm ID×500 mm L, manufactured by Daicel Corporation, mobile phase: hexane/2-propanol=600/400), THF (2 mL) and MeOH (1.000 mL) was added 1N aqueous sodium hydroxide solution (2 mL) at room temperature. The mixture was stirred at 60° C. for 20 min. The mixture was neutralized with 1N hydrochloric acid and extracted with ethyl acetate. The organic layer was separated, washed with water and saturated brine, dried over anhydrous magnesium sulfate and concentrated under reduced pressure. The obtained residue was crystallized from ethyl acetate/hexane to give the title compound (43 mg). $^1$H NMR (400 MHz, DMSO-d$_6$) δ1.32-1.49 (2H, m), 1.53-1.68 (4H, m), 1.82 (4H, d, J=10.4 Hz), 2.00 (1H, d, J=10.8 Hz), 2.34-2.46 (2H, m), 2.62 (2H, t, J=11.1 Hz), 2.76 (1H, d, J=15.2 Hz), 2.82-2.97 (3H, m), 3.01 (2H, d, J=10.4 Hz), 3.11-3.24 (4H, m), 3.70 (3H, s), 3.95-4.25 (4H, m), 6.53-6.66 (2H, m), 6.70 (1H, s), 7.13 (1H, d, J=7.8 Hz), 7.65 (1H, s), 12.53 (1H, brs).

Example 29

(3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetic acid (Optical Isomer))

To a mixture of ethyl (3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetate (61.0 mg) which is an optical isomer having longer retention time and obtained by separating a racemate of ethyl (3-((1-(5-methoxy-2-(1-(2,2,2-trifluoroethyl)piperidin-4-yl)phenyl) piperidin-4-yl)methoxy)-6,7-dihydro-5H-cyclopenta[c] pyridin-5-yl)acetate by HPLC (column: CHIRALPAK IC (trade name), 50 mm ID×500 mm L, manufactured by Daicel Corporation, mobile phase: hexane/2-propanol=600/400), THF (2 mL) and MeOH (1.000 mL) was added 1N aqueous sodium hydroxide solution (2 mL) at room temperature. The mixture was stirred at 60° C. for 30 min. The mixture was neutralized with 1N hydrochloric acid at room temperature and extracted with ethyl acetate. The organic layer was separated, washed with water and saturated brine, dried over anhydrous magnesium sulfate and concentrated under reduced pressure. The obtained residue was crystallized from ethyl acetate/hexane to give the title compound (44.8 mg).

Example 36

(6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid To a mixture of ethyl (6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetate (35 mg), THF (1 mL) and MeOH (0.500 mL) was added 1N aqueous sodium hydroxide solution (1 mL) at room temperature. The mixture was stirred at 60° C. for 30 min. The mixture was neutralized with 1N hydrochloric acid at room temperature and extracted with ethyl acetate. The organic layer was separated, washed with water and saturated brine, dried over anhydrous magnesium sulfate and concentrated under reduced pressure. The obtained residue was crystallized from ethyl acetate/hexane to give the title compound (24.5 mg). $^1$H NMR (300 MHz, DMSO-d$_6$) δ1.32-1.50 (2H, m), 1.52-1.70 (4H, m), 1.70-1.93 (4H, m), 1.96-2.13 (1H, m), 2.34-2.48 (2H, m), 2.63 (2H, t, J=11.2 Hz), 2.70-2.97 (4H, m), 3.02 (2H, d, J=11.2 Hz), 3.17 (4H, q, J=10.3 Hz), 3.70 (3H, s), 3.99-4.23 (4H, m), 6.56-6.65 (2H, m), 6.70 (1H, s), 7.13 (1H, d, J=9.1 Hz), 7.66 (1H, s), 12.34 (1H, brs).

Example 49

(6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (optical isomer) (compound of Example 9) can also be produced by the following method.

A) ethyl (6-(benzyloxy)-3,4-dihydro-2H-pyrano[2,3-c]pyridin-4-yl)acetate (optical isomer)

A racemate (20.0 g) of ethyl (6-(benzyloxy)-3,4-dihydro-2H-pyrano[2,3-c]pyridin-4-yl)acetate was separated by SFC (column: Alcyon SFC CSP Amylose-C (5 μm) 150×4.6 mm I.D., mobile phase: carbon dioxide/ethanol=90/10) to give the title compound (9.70 g) having longer retention time.

B) ethyl (6-hydroxy-3,4-dihydro-2H-pyrano[2,3-c]pyridin-4-yl)acetate (optical isomer)

A mixture of ethyl (6-(benzyloxy)-3,4-dihydro-2H-pyrano[2,3-c]pyridin-4-yl)acetate (optical isomer) (9.70 g), 10% palladium carbon (2.20 g).and ethyl acetate (240 mL) was stirred under a hydrogen atmosphere at normal pressure at room temperature for 1 hr. The catalyst was removed by filtration and the filtrate was concentrated under reduced pressure to give the title compound (6.93 g). MS: [M+H]$^+$ 238.1.

C) ethyl 1-(5-methoxy-2-nitrophenyl)piperidine-4-carboxylate

To a mixture of 2-fluoro-4-methoxy-1-nitrobenzene (45.9 g), potassium carbonate (44.5 g) and DMF (300 mL) was added ethyl piperidine-4-carboxylate (50.6 g) at room temperature. The mixture was stirred under a nitrogen atmosphere at 60° C. for 1 hr. To the reaction mixture was added water at room temperature, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (83.0 g). MS: [M+H]$^+$ 309.1.

D) ethyl 1-(2-amino-5-methoxyphenyl)piperidine-4-carboxylate

A mixture of ethyl 1-(5-methoxy-2-nitrophenyl)piperidine-4-carboxylate (83.0 g), 10% palladium carbon (10.0 g), EtOH (250 mL) and TH (250 mL) was stirred under a hydrogen atmosphere at normal pressure at room temperature for 5 hr. The catalyst was removed by filtration and the filtrate was concentrated under reduced pressure. The residue was purified by silica gel column chromatography (ethyl acetate/hexane) to give the title compound (71.0 g). MS: [M+H]$^+$ 279.1.

E) ethyl 1-(2-iodo-5-methoxyphenyl)piperidine-4-carboxylate

To a mixture of ethyl 1-(2-amino-5-methoxyphenyl)piperidine-4-carboxylate (71.0 g) and acetonitrile (300 mL) was added 2N hydrochloric acid (400 mL) at 0° C., and the mixture was stirred at the same temperature for 30 min. To the mixture was added a mixture of sodium nitrite (22.9 g) and water (50 mL) at 0° C. and the mixture was stirred under a nitrogen atmosphere at the same temperature for 30 min. To the mixture was added a mixture of potassium iodide (127 g) and water (150 mL) at 0° C., and the mixture was stirred under a nitrogen atmosphere at 60° C. for 1 hr. To the reaction mixture was added saturated aqueous sodium hydrogen carbonate solution at room temperature, and the mixture was extracted with ethyl acetate. The organic layer was separated, washed with saturated aqueous sodium thiosulfate solution and saturated brine, dried over anhydrous magnesium sulfate and concentrated under reduced pressure. The residue was purified by silica gel column chromatography (ethyl acetate/hexane) to give the title compound (79.0 g). MS: [M+H]$^+$ 390.0.

F) tert-butyl 4-(2-(4-(ethoxycarbonyl)piperidin-1-yl)-4-methoxyphenyl)-3,6-dihydropyridine-1(2H)-carboxylate A mixture of ethyl 1-(2-iodo-5-methoxyphenyl)piperidine-4-carboxylate (12.0 g), tert-butyl 4-(4,4,5,5-tetramethyl-1,3,2-dioxaborolan-2-yl)-3,6-dihydropyridine-1(2H)-carboxylate (17.8 g), [1,1'-bis(diphenylphosphino)ferrocene]palladium(II) dichloride (2.26 g), 2 M aqueous sodium carbonate solution (33.9 mL) and DMF (200 mL) was stirred under a nitrogen atmosphere at 100° C. for 2 hr. The reaction mixture was filtered, water was added to the filtrate at room temperature, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (12.5 g). MS: [M+H]$^+$ 445.3.

G) tert-butyl 4-(2-(4-(ethoxycarbonyl)piperidin-1-yl)-4-methoxyphenyl)piperidine-1-carboxylate A mixture of tert-butyl 4-(2-(4-(ethoxycarbonyl)piperidin-1-yl)-4-methoxyphenyl)-3,6-dihydropyridine-1(2H)-carboxylate (12.5 g), 10% palladium carbon (5.00 g) and THE (200 mL) was stirred under a hydrogen atmosphere at normal pressure at room temperature for 5 hr. The catalyst was removed by filtration and the filtrate was concentrated under reduced pressure to give the title compound (12.4 g). MS: [M+H]$^+$ 447.3.

H) ethyl 1-(5-methoxy-2-(1-(2,2,2-trifluoroethyl)piperidin-4-yl)phenyl)piperidine-4-carboxylate To a mixture of tert-butyl 4-(2-(4-(ethoxycarbonyl)piperidin-1-yl)-4-methoxyphenyl)piperidine-1-carboxylate (12.4 g) and ethyl acetate (60 mL) was added 4N hydrogen chloride ethyl acetate solution (104 mL) at room temperature. The mixture was stirred under a nitrogen atmosphere at the same temperature for 40 min, and the reaction mixture was concentrated. To a mixture of the obtained residue, TEA (38.7 mL) and acetonitrile (120 mL) was added 2,2,2-trifluoroethyl trifluoromethanesulfonate (14.0 mL) at room temperature. After stirring under a nitrogen atmosphere at 60° C. for 20 min, the reaction mixture was concentrated. To the residue was added ethyl acetate, insoluble material was removed by filtration, and the filtrate was concentrated under reduced pressure. The residue was purified by silica gel column chromatography (ethyl acetate/hexane) to give the title compound (10.9 g). MS: [M+H]$^+$ 429.2.

I) (1-(5-methoxy-2-(1-(2,2,2-trifluoroethyl)piperidin-4-yl)phenyl)piperidin-4-yl)methanol To a mixture of lithium aluminum hydride (2.68 g) and Et$_2$O (110 mL) was added a solution of ethyl 1-(5-methoxy-2-(1-(2,2,2-trifluoroethyl)piperidin-4-yl)phenyl)piperidine-4-carboxylate (10.1 g) in Et$_2$O (45 mL) at 0° C. The mixture was stirred under a nitrogen atmosphere at the same temperature for 20 min. To the mixture were added water and 1N aqueous sodium hydroxide solution, the obtained precipitate was removed by filtration, and the filtrate was concentrated under reduced pressure to give the title compound (8.66 g). MS: [M+H]$^+$ 387.2.

J) ethyl (6-((1-(5-methoxy-2-(1-(2,2,2-trifluoro-
ethyl)piperidin-4-yl)phenyl)piperidin-4-yl)methoxy)-
3,4-dihydro-2H-pyrano[2,3-c]pyridin-4-yl)acetate
(Optical Isomer)

To a mixture of (1-(5-methoxy-2-(1-(2,2,2-trifluoroethyl) piperidin-4-yl)phenyl)piperidin-4-yl)methanol (6.71 g), ethyl (6-hydroxy-3,4-dihydro-2H-pyrano[2,3-c]pyridin-4-yl)acetate (optical isomer) (3.43 g) and toluene (70 mL) was added (tributylphosphoranylidene)acetonitrile (6.98 g) at room temperature. The mixture was stirred under a nitrogen atmosphere at 100° C. for 2 hr. The reaction mixture was concentrated under reduced pressure, and the residue was purified by silica gel column chromatography (ethyl acetate/hexane) to give the title compound (5.28 g). MS: [M+H]$^+$ 606.4.

K) (6-((1-(5-methoxy-2-(1-(2,2,2-trifluoroethyl)
piperidin-4-yl)phenyl)piperidin-4-yl)methoxy)-3,4-
dihydro-2H-pyrano[2,3-c]pyridin-4-yl)acetic acid
(Optical Isomer)

To a mixture of ethyl (6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetate (optical isomer) (9.84 g), THF (200 mL) and MeOH (100 mL) was added 1N aqueous sodium hydroxide solution (195 mL) at room temperature. The mixture was stirred at 60° C. for 1 hr. The reaction mixture was neutralized with 1N hydrochloric acid at room temperature and extracted with ethyl acetate. The organic layer was separated, washed with water and saturated brine, dried over anhydrous magnesium sulfate and concentrated under reduced pressure. The obtained solid was crystallized from ethyl acetate/hexane to give the title compound (8.08 g). $^1$H NMR (300 MHz, CDCl$_3$) δ 1.44-1.64 (2H, m), 1.65-1.74 (3H, m), 1.75-1.95 (4H, m), 2.12-2.26 (1H, m), 2.43-2.74 (6H, m), 2.80-2.90 (1H, m), 2.82-3.14 (7H, m), 3.37 (1H, br dd, J=8.5, 5.7 Hz), 3.78 (3H, s), 4.08-4.25 (4H, m), 6.56-6.68 (3H, m), 7.14 (1H, d, J=8.4 Hz), 7.76 (1H, s).

Example 50

(6-((1-(2-(4,4-difluorocyclohexyl)-5-methoxyphe-
nyl)piperidin-4-yl)methoxy)-3,4-dihydro-2H-pyrano
[2,3-c]pyridin-4-yl)acetic acid (Optical Isomer)

A) ethyl 1-(2-(4,4-difluorocyclohex-1-en-1-yl)-5-
methoxyphenyl)piperidine-4-carboxylate A mixture of ethyl 1-(2-iodo-5-methoxyphenyl)piperidine-4-carboxylate (250 mg), 2-(4,4-difluorocyclohex-1-en-1-yl)-4,4,5,5-tetramethyl-1,3,2-dioxaborolane (270 mg), [1,1'-bis(diphenylphosphino)ferrocene]palladium(II) dichloride (94.0 mg), 2 M aqueous sodium carbonate solution (0.71 mL) and DMF (4 mL) was stirred under a nitrogen atmosphere at 100° C. for 2 hr. To the reaction mixture was added water at room temperature, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (180 mg). MS: [M+H]$^+$ 380.2.

B) ethyl 1-(2-(4,4-difluorocyclohexyl)-5-methoxy-
phenyl)piperidine-4-carboxylate A mixture of ethyl 1-(2-(4,4-difluorocyclohex-1-en-1-yl)-5-methoxyphenyl)piperidine-4-carboxylate (90.0 mg), 10% palladium carbon (30.0 mg) and THF (5 mL) was stirred under a hydrogen atmosphere at normal pressure at room temperature for 3 hr. The catalyst was removed by filtration and the filtrate was concentrated under reduced pressure to give the title compound (94.0 mg). MS: [M+H]$^+$ 382.3.

C) (1-(2-(4,4-difluorocyclohexyl)-5-methoxyphenyl)
piperidin-4-yl)methanol

To a mixture of lithium aluminum hydride (28.1 mg) and Et$_2$O (3 mL) was added a solution of ethyl 1-(2-(4,4-difluorocyclohexyl)-5-methoxyphenyl)piperidine-4-carboxylate (94.0 mg) in Et$_2$O (3 mL) at 0° C. The mixture was stirred under a nitrogen atmosphere at 0° C. for 20 min. To the reaction mixture were added water and aqueous sodium hydroxide solution, and the obtained precipitate was removed by filtration. The filtrate was concentrated under reduced pressure to give the title compound (80.0 mg). MS: [M+H]$^+$ 340.2.

D) ethyl (6-((1-(2-(4,4-difluorocyclohexyl)-5-
methoxyphenyl)piperidin-4-yl)methoxy)-3,4-di-
hydro-2H-pyrano[2,3-c]pyridin-4-yl)acetate (optical
isomer)

To a mixture of (1-(2-(4,4-difluorocyclohexyl)-5-methoxyphenyl)piperidin-4-yl)methanol (80.0 mg), ethyl (6-hydroxy-3,4-dihydro-2H-pyrano[2,3-c]pyridin-4-yl)acetate (optical isomer) (50.0 mg) and toluene (3 mL) was added (tributylphosphoranylidene)acetonitrile (102 mg) at room temperature. The mixture was stirred under a nitrogen atmosphere at 80° C. for 5 hr. The reaction mixture was concentrated under reduced pressure and the residue was purified by silica gel-column chromatography (ethyl acetate/hexane) to give the title compound (68.0 mg). MS: [M+H]$^+$ 559.4.

E) (6-((1-(2-(4,4-difluorocyclohexyl)-5-methoxy-
phenyl)piperidin-4-yl)methoxy)-3,4-dihydro-2H-
pyrano[2,3-c]pyridin-4-yl)acetic acid (Optical Iso-
mer)

To a mixture of ethyl (6-((1-(2-(4,4-difluorocyclohexyl)-5-methoxyphenyl)piperidin-4-yl)methoxy)-3,4-dihydro-2H-pyrano[2,3-c]pyridin-4-yl)acetate (optical isomer) (68.0 mg), THF (2 mL) and MeOH (1 mL) was added 1N aqueous sodium hydroxide solution (1.46 mL) at room temperature. The mixture was stirred at 60° C. for 2 hr. The reaction mixture was neutralized with 1N hydrochloric acid at room temperature and extracted with ethyl acetate. The organic layer was separated, washed with water and saturated brine, dried over anhydrous magnesium sulfate and concentrated under reduced pressure. The obtained solid was crystallized from ethyl acetate/hexane to give the title compound (54.0 mg). $^1$H NMR (300 MHz, DMSO-d$_6$) δ1.37-1.53 (2H, m), 1.57-1.71 (2H, m), 1.72-1.93 (7H, m), 1.95-2.16 (4H, m), 2.60-2.69 (3H, m), 2.88-3.09 (3H, m), 3.12-3.26 (2H, m), 3.70 (3H, s), 4.02-4.19 (4H, m), 6.60-6.71 (3H, m), 7.09 (1H, d, J=8.4 Hz), 7.65 (1H, s).

Example 51

(6-((1-(5-(4,4-difluorocyclohexyl)-2-methoxypyri-
din-4-yl)piperidin-4-yl)methoxy)-3,4-dihydro-2H-
pyrano[2,3-c]pyridin-4-yl)acetic acid (Optical Iso-
mer)

A) ethyl 1-(2-methoxy-5-nitropyridin-4-yl)piperi-
dine-4-carboxylate

A mixture of 4-chloro-2-methoxy-5-nitropyridine (913 mg), ethyl piperidine-4-carboxylate (0.784 mL) and EtOH (15 mL) was stirred at 80° C. overnight. To the reaction mixture was added water, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (1.50 g). MS: [M+H]$^+$ 310.1.

B) ethyl 1-(5-amino-2-methoxypyridin-4-yl)piperidine-4-carboxylate

A mixture of ethyl 1-(2-methoxy-5-nitropyridin-4-yl)piperidine-4-carboxylate (1.50 g), 10% palladium carbon (200 mg), EtOH (12 mL) and THF (12 mL) was stirred under a hydrogen atmosphere at normal pressure at room temperature overnight. The catalyst was removed by filtration and the filtrate was concentrated under reduced pressure. The residue was purified by silica gel column chromatography (ethyl acetate/hexane) to give the title compound (1.24 g). MS: [M+H]$^+$ 280.2.

C) ethyl 1-(5-iodo-2-methoxypyridin-4-yl)piperidine-4-carboxylate

To a mixture of ethyl 1-(5-amino-2-methoxypyridin-4-yl)piperidine-4-carboxylate (604 mg), 2N hydrochloric acid (3.5 mL) and acetonitrile (10 mL) was added a mixture of sodium nitrite (194 mg) and water (2.5 mL) at 0° C., and the mixture was stirred at the same temperature for 30 min. To the mixture was added a mixture of potassium iodide (1.08 g) and water (4.5 mL) at 0° C., and the mixture was stirred at 60° C. for 1 hr. To the reaction mixture was added saturated aqueous sodium hydrogen carbonate solution at 0° C., and the mixture, was extracted with ethyl acetate. The organic layer was separated, washed with saturated aqueous sodium thiosulfate solution and saturated brine, dried over anhydrous magnesium sulfate and concentrated under reduced pressure. The residue was purified by silica gel column chromatography (ethyl acetate/hexane) to give the title compound (822 mg). MS: [M+H]$^+$ 391.1.

D) ethyl 1-(5-(4,4-difluorocyclohex-1-en-1-yl)-2-methoxypyridin-4-yl)piperidine-4-carboxylate A mixture of ethyl 1-(5-iodo-2-methoxypyridin-4-yl)piperidine-4-carboxylate (200 mg), 2-(4,4-difluorocyclohex-1-en-1-yl)-4,4,5,5-tetramethyl-1,3,2-dioxaborolane (150 mg), [1,1'-bis(diphenylphosphino)ferrocene]palladium(II) dichloride (37.5 mg), 2 M aqueous sodium carbonate solution (0.384 mL) and DMF (5 mL) was stirred at 100° C. for 5 hr. To the reaction mixture was added water, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (80.1 mg). MS: [M+H]$^+$ 381.2.

E) ethyl 1-(5-(4,4-difluorocyclohexyl)-2-methoxypyridin-4-yl)piperidine-4-carboxylate A mixture of ethyl 1-(5-(4,4-difluorocyclohex-1-en-1-yl)-2-methoxypyridin-4-yl)piperidine-4-carboxylate (80.1 mg), 10% palladium carbon (20.0 mg) and THF (5 mL) was stirred under a hydrogen atmosphere at normal pressure at room temperature overnight. The catalyst was removed by filtration and the filtrate was concentrated under reduced pressure. The residue was purified by silica gel column chromatography (ethyl acetate/hexane) to give the title compound (54.4 mg). MS: [M+H]$^+$ 383.2.

F) (1-(5-(4,4-difluorocyclohexyl)-2-methoxypyridin-4-yl)piperidin-4-yl)methanol

A mixture of ethyl 1-(5-(4,4-difluorocyclohexyl)-2-methoxypyridin-4-yl)piperidine-4-carboxylate (54.4 mg), lithium borohydride (17.2 mg) and THF (7 mL) was stirred at 60° C. for 3 hr. To the reaction mixture was added saturated aqueous ammonium chloride solution at 0° C., and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (44.5 mg). MS: [M+H]$^+$ 341.2.

G) ethyl (6-((1-(5-(4,4-difluorocyclohexyl)-2-methoxypyridin-4-yl)piperidin-4-yl)methoxy)-3,4-dihydro-2H-pyrano[2,3-c]pyridin-4-yl)acetate (optical isomer)

A mixture of (1-(5-(4,4-difluorocyclohexyl)-2-methoxypyridin-4-yl)piperidin-4-yl)methanol (44.5 mg), ethyl (6-hydroxy-3,4-dihydro-2H-pyrano[2,3-c]pyridin-4-yl)acetate (optical isomer) (34.1 mg), (tributylphosphoranylidene)acetonitrile (0.171 mL) and toluene (5 mL) was stirred at 100° C. for 6 hr. To the reaction mixture was added water, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (42.6 mg). MS: [M+H]$^+$ 560.3.

H) (6-((1-(5-(4,4-difluorocyclohexyl)-2-methoxypyridin-4-yl)piperidin-4-yl)methoxy)-3,4-dihydro-2H-pyrano[2,3-c]pyridin-4-yl)acetic acid (Optical Isomer)

To a mixture of ethyl (6-((1-(5-(4,4-difluorocyclohexyl)-2-methoxypyridin-4-yl)piperidin-4-yl)methoxy)-3,4-dihydro-2H-pyrano[2,3-c]pyridin-4-yl)acetate (optical isomer) (42.6 mg), THF (1.5 mL) and MeOH (1.5 mL) was added 1N aqueous sodium hydroxide solution (0.800 mL) at room temperature. The mixture was stirred at room temperature overnight. The reaction mixture was neutralized with 1N hydrochloric acid and extracted with ethyl acetate. The organic layer was separated, washed with saturated brine, dried over anhydrous magnesium sulfate and concentrated under reduced pressure. The obtained solid was crystallized from ethyl acetate/hexane to give the title compound (34.4 mg). $^1$H NMR (300 MHz, DMSO-d$_6$) δ 1.21-1.34 (2H, m), 1.37-1.55 (2H, m), 1.58-1.93 (7H, m), 1.97-2.21 (4H, m), 2.57-2.70 (2H, m), 2.71-2.86 (2H, m), 3.03-3.14 (2H, m), 3.16-3.28 (2H, m), 3.77 (3H, s), 4.00-4.24 (4H, m), 6.33 (1H, s), 6.70 (1H, s), 7.65 (1H, s), 7.90 (1H, s).

Example 52

(6-((1-(2-methoxy-5-(3,3,3-trifluoropropyl)pyridin-4-yl)piperidin-4-yl)methoxy)-3,4-dihydro-2H-pyrano[2,3-c]pyridin-4-yl)acetic acid (Optical Isomer)

A) ethyl 6-chloro-4-(4-(hydroxymethyl)piperidin-1-yl)nicotinate

A mixture of ethyl 4,6-dichloronicotinate (5.24 g), 4-piperidylmethanol (4.11 g), N,N-diisopropylethylamine (12.4 mL) and THF (60 mL) was stirred at room temperature for 2 days. The reaction mixture was concentrated under reduced pressure and the residue was diluted with ethyl acetate. The obtained mixture was washed with water and saturated brine, dried over anhydrous magnesium sulfate and concentrated under reduced pressure. The residue was purified by silica gel column chromatography (ethyl acetate/hexane) to give the title compound (6.69 g). MS: [M+H]$^+$ 299.2.

B) ethyl 6-chloro-4-(4-((methoxymethoxy)methyl)piperidin-1-yl)nicotinate

A mixture of ethyl 6-chloro-4-(4-(hydroxymethyl)piperidin-1-yl)nicotinate (6.69 g), chloro(methoxy)methane (5.10 mL), N,N-diisopropylethylamine (15.6 mL) and THF (100 mL) was heated under reflux for 3 hr. The reaction mixture was concentrated under reduced pressure and the residue was diluted with ethyl acetate. The obtained mixture was washed with water and saturated brine, dried over anhydrous magnesium sulfate and concentrated under reduced pressure. The residue was purified by silica gel column chromatography (ethyl acetate/hexane) to give the title compound (5.62 g). MS: [M+H]$^+$ 343.2.

C) methyl 6-methoxy-4-(4-((methoxymethoxy)methyl)piperidin-1-yl)nicotinate

A mixture of ethyl 6-chloro-4-(4-((methoxymethoxy)methyl)piperidin-1-yl)nicotinate (5.62 g), sodium methoxide (28% methanol solution, 15.8 g) and methanol (60 mL) was heated under reflux for 9 hr. The reaction mixture was diluted with ethyl acetate, washed with saturated aqueous ammonium chloride solution, water and saturated brine, dried over anhydrous magnesium sulfate and concentrated under reduced pressure. The residue was purified by silica gel column chromatography (ethyl acetate/hexane) to give the title compound (4.43 g). MS: [M+H]$^+$ 325.2.

D) (6-methoxy-4-(4-((methoxymethoxy)methyl)piperidin-1-yl)pyridin-3-yl)methanol To a mixture of lithium aluminum hydride (0.777 g) and THF (50 mL) was added a solution of methyl 6-methoxy-4-(4-((methoxymethoxy)methyl)piperidin-1-yl)nicotinate (4.43 g) in THF (20 mL) at 0° C., and the mixture was stirred at the same temperature for 20 min. To the reaction mixture was added sodium sulfate 10 hydrate at 0° C., and the mixture was stirred at room temperature for 1 hr. The solid was removed by filtration and the filtrate was concentrated under reduced pressure to give the title compound (4.16 g). MS: [M+H]$^+$ 297.2.

E) 6-methoxy-4-(4-((methoxymethoxy)methyl)piperidin-1-yl)nicotinaldehyde

A mixture of (6-methoxy-4-(4-((methoxymethoxy)methyl)piperidin-1-yl)pyridin-3-yl)methanol (4.07 g), manganese dioxide (85%, 7.02 g) and toluene (70 mL) was stirred at 60° C. for 1.5 hr. The solid was removed by filtration and the filtrate was concentrated under reduced pressure to give the title compound (4.12 g). MS: [M+H]$^+$ 295.2.

F) 2-methoxy-4-(4-((methoxymethoxy)methyl)piperidin-1-yl)-5-vinylpyridine

To a mixture of methyltriphenylphosphonium iodide (8.24 g) and THF (30 mL) was added potassium tert-butoxide (85%, 2.24 g) at 0° C., and the mixture was stirred at room temperature for 1 hr. To the mixture was added a solution of 6-methoxy-4-(4-((methoxymethoxy)methyl)piperidin-1-yl)nicotinaldehyde (2.00 g) in THF (5 mL) at 0° C., and the mixture was stirred at room temperature for 30 min. To the reaction mixture was added saturated aqueous ammonium chloride and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (1.81 g). MS: [M+H]$^+$ 293.2.

G) 3,3,3-trifluoro-1-(6-methoxy-4-(4-((methoxymethoxy)methyl)piperidin-1-yl)pyridin-3-yl)propyl 2-iodobenzoate A mixture of 2-methoxy-4-(4-((methoxymethoxy)methyl)piperidin-1-yl)-5-vinylpyridine (1.81 g), 1-trifluoromethyl-1,2-benzoiodoxol-3(1H)-one (containing 60% diatomaceous earth, 5.87 g), tetrakis(acetonitrile)copper(I) hexafluorophosphate (0.461 g) and dichloromethane (40 mL) was stirred at room temperature overnight. The solid was removed by filtration and the filtrate was concentrated under reduced pressure. The residue was diluted with ethyl acetate, washed with saturated aqueous sodium hydrogen carbonate solution, water and saturated brine, dried over anhydrous magnesium sulfate and concentrated under reduced pressure. The residue was purified by silica gel column chromatography (ethyl acetate/hexane) to give the title compound (1.65 g). MS: [M+H]$^+$ 609.2.

H) 3,3,3-trifluoro-1-(6-methoxy-4-(4-((methoxymethoxy)methyl)piperidin-1-yl)pyridin-3-yl)propan-1-ol To a mixture of 3,3,3-trifluoro-1-(6-methoxy-4-(4-((methoxymethoxy)methyl)piperidin-1-yl)pyridin-3-yl)propyl 2-iodobenzoate (1.61 g) and ethanol (15 mL) was added 2N aqueous sodium hydroxide solution (5 mL) at room temperature, and the mixture was stirred at the same temperature for 3.5 hr. To the reaction mixture was added water at room temperature, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (0.880 g). MS: [M+H]$^+$ 379.2.

I) S-methyl 0-(3,3,3-trifluoro-1-(6-methoxy-4-(4-((methoxymethoxy)methyl)piperidin-1-yl)pyridin-3-yl)propyl) carbonodithioate To a mixture of 3,3,3-trifluoro-1-(6-methoxy-4-(4-((methoxymethoxy)methyl)piperidin-1-yl)pyridin-3-yl)propan-1-ol (0.760 g) and THF (20 mL) was added sodium hydride (60% in oil, 0.241 g) at 0° C., and the mixture was stirred at room temperature for 10 min. To the mixture was added carbon disulfide (0.604 mL) at 0° C., and the mixture was stirred at room temperature for 2 hr. To the mixture was added methyl iodide (0.625 mL) at room temperature, and the mixture was stirred at the same temperature overnight. To the reaction mixture was added saturated aqueous ammonium chloride solution, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (0.910 g). MS: [M+H]$^+$ 469.2.

J) 2-methoxy-4-(4-((methoxymethoxy)methyl)piperidin-1-yl)-5-(3,3,3-trifluoropropyl)pyridine A mixture of S-methyl 0-(3,3,3-trifluoro-1-(6-methoxy-4-(4-((methoxymethoxy)methyl)piperidin-1-yl)pyridin-3-yl)propyl) carbonodithioate (0.910 g), tributyltin hydride (1.57 mL), azobisisobutyronitrile (0.159 g) and toluene (20 mL) was stirred at 100° C. overnight. The solvent was evaporated under reduced pressure and the residue was purified by silica gel column chromatography (ethyl acetate/hexane) to give the title compound (0.460 g). MS: [M+H]$^+$ 363.2.

K) (1-(2-methoxy-5-(3,3,3-trifluoropropyl)pyridin-4-yl)piperidin-4-yl)methanol A mixture of 2-methoxy-4-(4-((methoxymethoxy)methyl) piperidin-1-yl)-5-(3,3,3-trifluoropropyl)pyridine (0.460 g), concentrated hydrochloric acid (1.06 mL) and methanol (10 mL) was stirred at 60° C. for 1.5 hr. To the reaction mixture was added saturated aqueous sodium hydrogen carbonate solution, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (0.400 g). MS: [M+H]$^+$ 319.2.

L) ethyl (6-((1-(2-methoxy-5-(3,3,3-trifluoropropyl) pyridin-4-yl)piperidin-4-yl)methoxy)-3,4-dihydro-2H-pyrano[2,3-c]pyridin-4-yl)acetate (optical isomer)

A mixture of (1-(2-methoxy-5-(3,3,3-trifluoropropyl) pyridin-4-yl)piperidin-4-yl)methanol (0.221 g), ethyl (6-hydroxy-3,4-dihydro-2H-pyrano[2,3-c]pyridin-4-yl)acetate (optical isomer) (0.150 g), (tributylphosphoranylidene)acetonitrile (0.332 mL) and toluene (4 mL) was stirred at 100° C. overnight. The reaction mixture was purified by silica gel column chromatography (ethyl acetate/hexane) to give the title compound (0.230 g). MS: [M+H]$^+$ 538.3.

M) (6-((1-(2-methoxy-5-(3,3,3-trifluoropropyl)pyridin-4-yl)piperidin-4-yl)methoxy)-3,4-dihydro-2H-pyrano[2,3-c]pyridin-4-yl)acetic acid (Optical Isomer)

To a mixture of ethyl (6-((1-(2-methoxy-5-(3,3,3-trifluoropropyl)pyridin-4-yl)piperidin-4-yl)methoxy)-3,4-dihydro-2H-pyrano[2,3-c]pyridin-4-yl)acetate (optical isomer) (0.230 g), THF (2 mL) and ethanol (2 mL) was added 2N aqueous sodium hydroxide solution (1.0 mL) at room temperature, and the mixture was stirred at the same temperature for 4 hr. The reaction mixture was concentrated under reduced pressure, diluted with water (15 mL) and neutralized with 1N hydrochloric acid (pH 5). The precipitated solid was collected by filtration and washed with water to give the title compound (0.200 g). $^1$H NMR (300 MHz, DMSO-d$_6$) δ 1.27-1.50 (2H, m), 1.67-1.95 (4H, m), 1.98-2.14 (1H, m), 2.52-2.93 (8H, m), 3.17 (3H, br d, J=10.9 Hz), 3.78 (3H, s), 3.99-4.27 (4H, m), 6.34 (1H, s), 6.69 (1H, s), 7.65 (1H, s), 7.93 (1H, s), 12.51 (1H, br s).

Reference Example 1

6-(benzyloxy)-2,3-dihydro-4H-pyrano[2,3-c]pyridin-4-one (compound of Example 1, E)) can also be produced by the following method.

To a mixture of 6-(benzyloxy)-4H-pyrano[2,3-c]pyridin-4-one (45.8 g) and THF (900 mL) was added dropwise diisobutylaluminum hydride (1.5 M toluene solution, 241 mL) at −78° C. over 1 hr. The mixture was stirred at the same temperature for 1 hr. To the reaction mixture was added a mixture of silica gel (50 g) and water (50 mL) over 5 hr, and the mixture was heated to room temperature and stirred at the same temperature for 3 hr. The obtained precipitate was removed by filtration, washed with ethyl acetate, and the filtrate was concentrated under reduced pressure. The residue was purified by silica gel column chromatography (ethyl acetate/hexane) to give the title compound (23.6 g). MS: [M+H]$^+$ 256.0.

Reference Example 2

Ethyl (6-(benzyloxy)-3,4-dihydro-2H-pyrano[2,3-c]pyridin-4-yl)acetate (compound of Example 1, G)) can also be produced by the following method.

A) 2-(benzyloxy)-4-iodo-5-(methoxymethoxy)pyridine

To a mixture of 2-(benzyloxy)-5-(methoxymethoxy)pyridine (3.81 g) and THF (70 mL) was added n-butyllithium (1.6 M hexane solution, 14.6 mL) at −78° C. The mixture was stirred at the same temperature for 30 min, and a solution of iodine (11.8 g) in THF was added at −78° C. The mixture was stirred at the same temperature for 1 hr. To the reaction mixture was added saturated aqueous sodium thiosulfate solution at −78° C., and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (4.40 g). MS: [M+H]$^+$ 372.0.

B) 6-(benzyloxy)-4-iodopyridin-3-ol

To a mixture of 2-(benzyloxy)-4-iodo-5-(methoxymethoxy)pyridine (5.48 g) and THF (60 mL) was added 6N hydrochloric acid (40 mL) at room temperature. The mixture was stirred at the same temperature for 6 hr. To the reaction mixture was added water, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (4.19 g). MS: [M+H]+ 328.0.

C) 3-((6-(benzyloxy)-4-iodopyridin-3-yl)oxy)propan-1-ol

A mixture of 6-(benzyloxy)-4-iodopyridin-3-ol (1.37 g), potassium carbonate (871 mg), 3-bromo-1-propanol (0.455 mL) and DMF (15 mL) was stirred at room temperature overnight. To the reaction mixture was added water, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (1.53 g). MS: [M+H]+ 386.0.

D) ethyl (2E)-5-((6-(benzyloxy)-4-iodopyridin-3-yl)oxy)pent-2-enoate

A mixture of 3-((6-(benzyloxy)-4-iodopyridin-3-yl)oxy)propan-1-ol (1.28 g), ethyl (triphenylphosphoranylidene)acetate (1.39 g), manganese dioxide (2.88 g) and 1,2-dichloroethane (30 mL) was stirred at 90° C. overnight. The reaction mixture was filtered and the filtrate was concentrated. The residue was purified by silica gel column chromatography (ethyl acetate/hexane) to give the title compound (1.10 g). MS: [M+H]+ 454.2.

E) ethyl (6-(benzyloxy)-3,4-dihydro-2H-pyrano[2,3-c]pyridin-4-yl)acetate

To a mixture of ethyl (2E)-5-((6-(benzyloxy)-4-iodopyridin-3-yl)oxy)pent-2-enoate (1.10 g), N,N-diisopropylethylamine (0.508 mL), tris(trimethylsilyl)silane (1.50 mL) and benzotrifluoride (15 mL) was added azobisisobutyronitrile (120 mg) at room temperature. The mixture was stirred at 80° C. for 2 hr. To the reaction mixture was added saturated aqueous sodium hydrogen carbonate solution, and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (754 mg). MS: [M+H]+ 328.3.

Reference Example 3

Ethyl (6-(benzyloxy)-3,4-dihydro-2H-pyrano[2,3-c]pyridin-4-yl)acetate (optical isomer) (compound of Example 49, A)) can also be produced by the following method.

A) (6-(benzyloxy)-3,4-dihydro-2H-pyrano[2,3-c]pyridin-4-yl)acetic acid

To a mixture of ethyl (6-(benzyloxy)-3,4-dihydro-2H-pyrano[2,3-c]pyridin-4-yl)acetate (5.00 g), EtOH (25 mL) and THF (25 mL) was added 2N aqueous sodium hydroxide solution (19.1 mL) at room temperature. The mixture was stirred at the same temperature overnight and concentrated under reduced pressure. The residue was neutralized (pH 6) with 2N hydrochloric acid at 0° C., and the obtained solid was collected by filtration and washed with water to give the title compound (4.56 g). MS: [M+H]+ 300.2.

B) (1S)-1-(1-naphthyl)ethanaminium (6-(benzyloxy)-3,4-dihydro-2H-pyrano[2,3-c]pyridin-4-yl)acetate (optical isomer)

To a mixture of a racemate (1.00 g) of (6-(benzyloxy)-3,4-dihydro-2H-pyrano[2,3-c]pyridin-4-yl)acetic acid and EtOH (15 mL) was added (1S)-1-(1-naphthyl)ethanamine (572 mg) at room temperature. The mixture was gradually heated to 70° C. and water (1.1 mL) was added. The mixture was gradually cooled to room temperature and stirred overnight. The mixture was stirred at 0° C. for 1 hr, and the precipitate was collected by filtration and washed with EtOH and ethyl acetate to give the title compound (700 mg, d.r.=94.8:5.2). A mixture of the obtained solid, EtOH (12 mL) and water (0.7 mL) was dissolved at 70-75° C., the solution was gradually cooled to room temperature and stirred overnight. The mixture was stirred at 0° C. for 2 hr, and the precipitate was collected by filtration and washed with ethyl acetate and EtOH to give the title compound (559 mg, d.r.=99.6:0.4).

The diastereomer ratio was analyzed by chiral HPLC (CHIRALPAK IC (trade name), 4.6 mm ID×250 mm L, manufactured by Daicel Corporation, mobile phase: 0.1% TFA containing hexane/0.1% TFA containing 2-propanol=80/20). MS: [M+H]+ 300.0.

C) (6-(benzyloxy)-3,4-dihydro-2H-pyrano[2,3-c]pyridin-4-yl)acetic acid (Optical Isomer)

To a mixture of (1S)-1-(1-naphthyl)ethanaminium (6-(benzyloxy)-3,4-dihydro-2H-pyrano[2,3-c]pyridin-4-yl)acetate (optical isomer) (322 mg) and water (10 mL) was added 2N aqueous sodium hydroxide solution (5 mL). The reaction mixture was washed with diethyl ether. The aqueous layer was neutralized with 2N hydrochloric acid (pH 6-7), the mixture was stirred at 0° C. for 30 min, and the precipitate was collected by filtration and washed with water to give the title compound (191 mg). MS: [M+H]+ 300.2.

D) ethyl (6-(benzyloxy)-3,4-dihydro-2H-pyrano[2,3-c]pyridin-4-yl)acetate (optical isomer)

To a mixture of (6-(benzyloxy)-3,4-dihydro-2H-pyrano[2,3-c]pyridin-4-yl)acetic acid (Optical Isomer) (300 mg) and EtOH (12 mL) was added concentrated sulfuric acid (0.2 mL). The mixture was heated under reflux for 7 hr. To the reaction mixture was added saturated aqueous sodium hydrogen carbonate solution at room temperature, and the mixture was extracted with ethyl acetate. The organic layer was separated, washed with saturated brine, dried over anhydrous magnesium sulfate and concentrated under reduced pressure to give the title compound (316 mg). MS: [M+H]+ 328.2.

The Example compounds are shown in the following Tables. In the Tables, MS shows Found. The compounds of Examples 12-16, 19-27, 30-35, 37-48 and 53-59 in the following Tables were produced according to the methods shown in the above-mentioned Examples or methods analogous thereto.

TABLE 1-1

| Ex. No. | IUPAC name | structural formula | salt | MS |
|---|---|---|---|---|
| 1 | (6-((1-(5-methoxy-2-(3,3,3-trifluoropropyl)phenyl-piperidin-4-yl)methoxy)-3,4-dihydro-2H-pyrano[2,3-c]pyridin-4-yl)acetic acid | | | 509.3 |
| 2 | (6-((1-(2-methoxy-5-(2,2,3,3,3-pentafluoropropoxy)pyridin-4-yl)piperidin-4-yl)methoxy)-3,4-dihydro-2H-pyrazo[2,3-c]pyridin-4-yl)acetic acid | | | 562.1 |
| 3 | (3-((1-(2-methoxy-5-(2,2,3,3,3-pentafluoropropoxy)pyridin-4-yl)piperidin-4-yl)methoxy)-6,7-dihydro-5H-cyclopenta[c]pyridin-5-yl)acetic acid | | | 546.1 |
| 4 | (3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetic acid | | | 562.2 |

TABLE 1-1-continued

| Ex. No. | IUPAC name | structural formula | salt | MS |
|---|---|---|---|---|
| 5 | (6-((1-(2-methoxy-5-(1-(2,2,2-trifluoroethyl)piperidin-4-yl)pyridin-4-yl)piperidin-4-yl)methoxy)-3,4-dihydro-2H-pyrano[2,3-c]pyridin-4-yl)acetic acid | 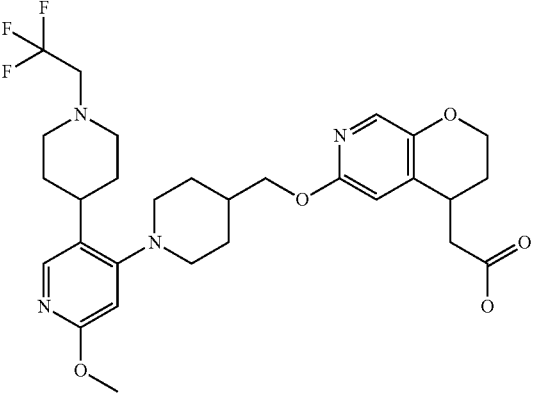 [SMILES: COc1cc(N2CCC(COc3cc4c(cn3)OCCC4CC(=O)O)CC2)c(C2CCN(CC(F)(F)F)CC2)cn1] | | 579.4 |

TABLE 1-2

| Ex. No. | IUPAC name | structural formula | salt | MS |
|---|---|---|---|---|
| 6 | (6-((1-(2-methoxy-5-(1-(2,2,2-trifluoroethyl)piperidin-4-yl)pyridin-4-yl)piperidin-4-yl)methoxy)-3,4-dihydro-2H-pyrano[2,3-c]pyridin-4-yl)acetic acid (optical isomer) | 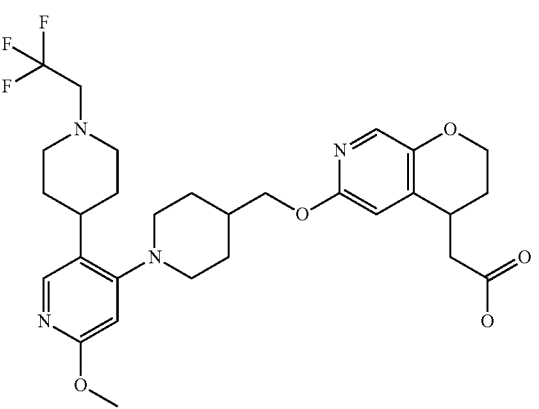 [SMILES: COc1cc(N2CCC(COc3cc4c(cn3)OCCC4CC(=O)O)CC2)c(C2CCN(CC(F)(F)F)CC2)cn1] | | 579.2 |
| 7 | (6-((1-(2-methoxy-5-(1-(2,2,2-trifluoroethyl)piperidin-4-yl)pyridin-4-yl)piperidin-4-yl)methoxy)-3,4-dihydro-2H-pyrano[2,3-c]pyridin-4-yl)acetic acid (optical isomer) | 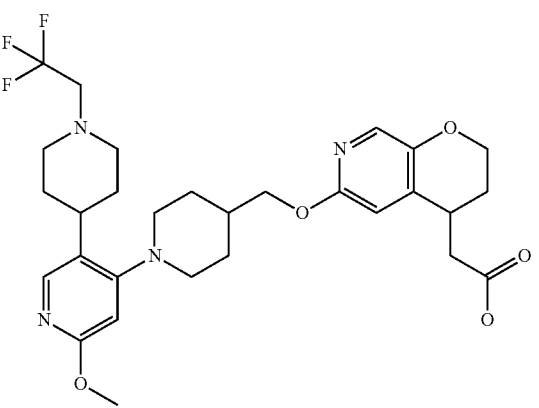 [SMILES: COc1cc(N2CCC(COc3cc4c(cn3)OCCC4CC(=O)O)CC2)c(C2CCN(CC(F)(F)F)CC2)cn1] | | 579.2 |

TABLE 1-2-continued

| Ex. No. | IUPAC name | structural formula | salt | MS |
|---|---|---|---|---|
| 8 | (6-((1-(5-methoxy-2-(3,3,3-trifluoropropyl)phenyl)-piperidin-4-yl)methoxy)-3,4-dihydro-2H-pyrano[2,3-c]pyridin-4-yl)acetic acid (optical isomer) | 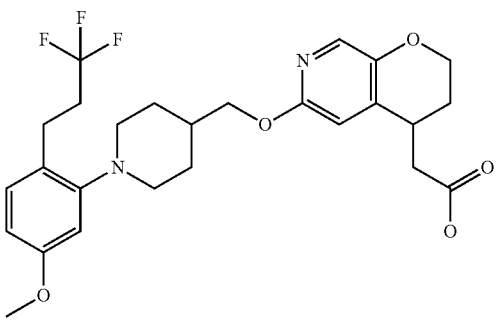 [SMILES: COc1ccc(CCC(F)(F)F)c(N2CCC(COc3cc4c(cn3)OCCC4CC(=O)O)CC2)c1] | | 509.2 |
| 9 | (6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (optical isomer) | 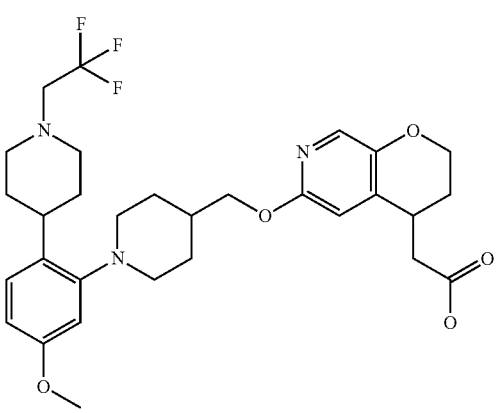 [SMILES: COc1ccc(C2CCN(CC(F)(F)F)CC2)c(N2CCC(COc3cc4c(cn3)OCCC4CC(=O)O)CC2)c1] | | 578.2 |
| 10 | (3-((1-(5-methoxy-2-(1-(2,2,2-trifluoroethyl)piperidin-4-yl)phenyl)piperidin-4-yl)methoxy)-6,7-dihydro-5H-cyclopenta[c]pyridin-5-yl)acetic acid (optical isomer) | 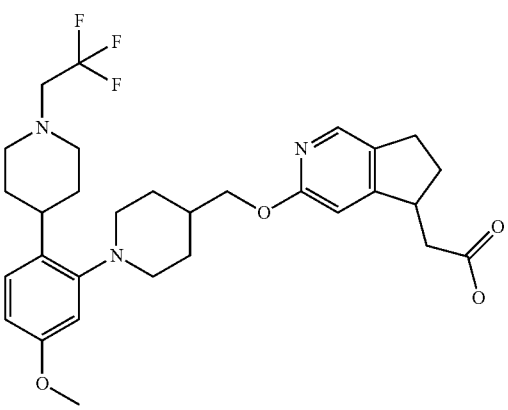 [SMILES: COc1ccc(C2CCN(CC(F)(F)F)CC2)c(N2CCC(COc3cc4c(cn3)CCC4CC(=O)O)CC2)c1] | | 562.2 |

TABLE 1-3

| Ex. No. | IUPAC name | structural formula | salt | MS |
|---|---|---|---|---|
| 11 | (6-((1-(2-methoxy-5-(2,2,3,3,3-pentafluoro-propoxy)pyridin-4-yl)piperidin-4-yl)methoxy)-3,4-dihydro-2H-pyrano[2,3-c]pyridin-4-yl)acetic acid (optical isomer) | | | 562.1 |
| 12 | (6-((1-(4-methoxy-4'-(morpholin-4-yl)biphenyl-2-yl)piperidin-4-yl)methoxy)-3,4-dihydro-2H-pyrano[2,3-c]pyridin-4-yl)acetic acid | | | 574.3 |
| 13 | (6-((1-(4-methoxy-4'-(trifluoromethoxy)biphenyl-2-yl)piperidin-4-yl)methoxy)-3,4-dihydro-2H-pyrano[2,3-c]pyridin-4-yl)acetic acid | | | 573.2 |
| 14 | (3-((1-(4-methoxy-4'-(trifluoromethoxy)biphenyl-2-yl)piperidin-4-yl)methoxy)-6,7-dihydro-5H-cyclopenta[c]pyridin-5-yl)acetic acid | | | 557.2 |

TABLE 1-3-continued

| Ex. No. | IUPAC name | structural formula | salt | MS |
|---|---|---|---|---|
| 15 | (3-((trans-4-(5-methoxy-2-(2-(2,2,2-trifluoroethoxy)pyrimidin-5-yl)phenoxy)cyclohexyl)oxy)-6,7-dihydro-5H-cyclopenta[c]pyridin-5-yl)acetic acid | | | 574.2 |
| 16 | (6-((trans-4-(5-methoxy-2-(2-(2,2,2-trifluoroethoxy)pyrimidin-5-yl)phenoxy)cyclohexyl)oxy)-3,4-dihydro-2H-pyrano[2,3-c]pyridin-4-yl)acetic acid | | | 590.2 |

TABLE 1-4

| Ex. No. | IUPAC name | structural formula | salt | MS |
|---|---|---|---|---|
| 17 | (6-((1-(2-methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetic acid (optical isomer) | | | 562.1 |

TABLE 1-4-continued

| Ex. No. | IUPAC name | structural formula | salt | MS |
|---|---|---|---|---|
| 18 | (6-((1-(5-methoxy-2-(3,3,3-trifluoropropoxy)phenyl)-piperidin-4-yl)methoxy)-3,4-dihydro-2H-pyrano[2,3-c]pyridin-4-yl)acetic acid (optical isomer) | 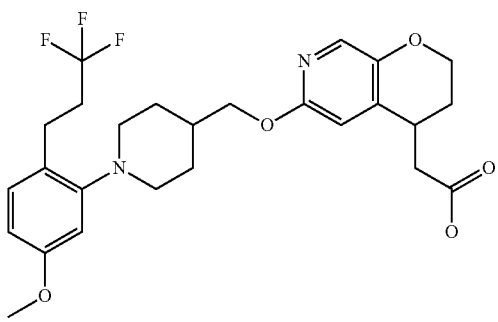 [SMILES: COc1ccc(CCC(F)(F)F)c(N2CCC(COc3cc4c(cn3)OCCC4CC(=O)O)CC2)c1] | | 509.2 |
| 19 | (3-((trans-4-(5-methoxy-2-(1-(2,2,3,3,3-pentafluoropropyl)piperidin-4-yl)phenoxy)cyclohexyl)-oxy)-6,7-dihydro-5H-cyclopenta[c]pyridin-5-yl)acetic acid | 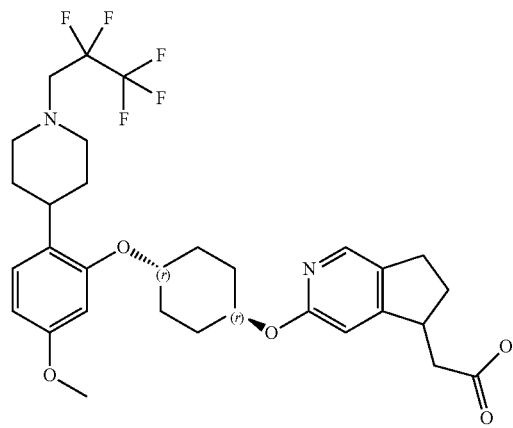 | | 613.1 |
| 20 | (3-((trans-4-(5-methoxy-2-(1-(2,2,2-trifluoroethyl)piperidin-4-yl)phenoxy)cyclohexyl)oxy)-6,7-dihydro-5H-cyclopenta[c]pyridin-5-yl)acetic acid | 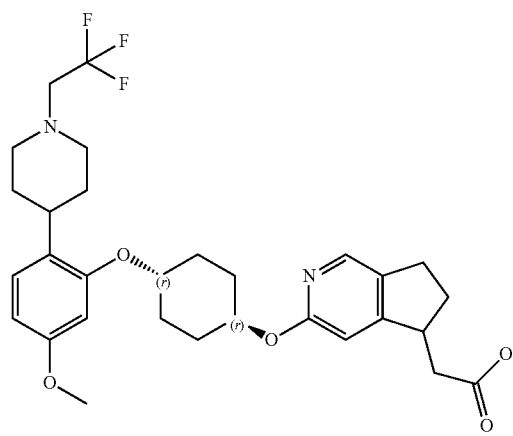 | | 563.2 |

TABLE 1-4-continued

| Ex. No. | IUPAC name | structural formula | salt | MS |
|---|---|---|---|---|
| 21 | (6-((trans-4-(5-methoxy-2-(1-(2,2,3,3,3-pentafluoropropyl)piperidin-4-yl)phenoxy)cyclohexyl)-oxy)-3,4-dihydro-2H-pyrano[2,3-c]pyridin-4-yl)acetic acid | | | 629.2 |

TABLE 1-5

| Ex. No. | IUPAC name | structural formula | salt | MS |
|---|---|---|---|---|
| 22 | (6-((trans-4-(5-methoxy-2-(1-(2,2,2-trifluoroethyl)piperidin-4-yl)phenoxy)cyclohexyl)oxy)-3,4-dihydro-2H-pyrano[2,3-c]pyridin-4-yl)acetic acid | | | 579.2 |
| 23 | (6-((1-(5-methoxy-2-(5-(trifluoromethyl)pyridin-2-yl)phenyl)piperidin-4-yl)methoxy)-3,4-dihydro-2H-pyrano[2,3-c]pyridin-4-yl)acetic acid | | | 558.1 |

TABLE 1-5-continued

| Ex. No. | IUPAC name | structural formula | salt | MS |
|---|---|---|---|---|
| 24 | (3-((1-(5-methoxy-2-(5-(trifluoromethyl)pyridin-2-yl)phenyl)piperidin-4-yl)methoxy)-6,7-dihydro-5H-cyclopenta[c]pyridin-5-yl)acetic acid | | | 542.2 |
| 25 | (6-((1-(5-methoxy-2-(6-(trifluoromethyl)pyridin-3-yl)phenyl)piperidin-4-yl)methoxy)-3,4-dihydro-2H-pyrano[2,3-c]pyridin-4-yl)acetic acid | | | 558.1 |
| 26 | (3-((1-(5-methoxy-2-(6-(trifluoromethyl)pyridin-3-yl)phenyl)piperidin-4-yl)methoxy)-6,7-dihydro-5H-cyclopenta[c]pyridin-5-yl)acetic acid | | | 542.2 |
| 27 | (6-((1-(5-methoxy-2-(1,1,1-trifluoropropan-2-yl)phenyl)piperidin-4-yl)methoxy)-3,4-dihydro-2H-pyrano[2,3-c]pyridin-4-yl)acetic acid | | | 509.2 |

TABLE 1-6

| Ex. No. | IUPAC name | structural formula | salt | MS |
|---|---|---|---|---|
| 28 | (6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (optical isomer) | | | 578.2 |
| 29 | (3-((1-(5-methoxy-2-(1-(2,2,2,-trifluoroethyl)-piperidin-4-yl)phenyl)-piperidin-4-yl)methoxy)-6,7-dihydro-5H-cyclopenta[c]-pyridin-5-yl)acetic acid (optical isomer)) | | | 562.4 |
| 30 | (3-((1-(5-methoxy-2-(3,3,3-trifluoropropyl)phenyl)-piperidin-4-yl)methoxy)-6,7-dihydro-5H-cyclopenta[c]pyridin-5-yl)acetic acid | | | 493.2 |
| 31 | (3-((1-(5-methoxy-2-(1,1,1-trifluoropropan-2-yl)phenyl)piperidin-4-yl)methoxy)-6,7-dihydro-5H-cyclopenta[c]pyridin-5-yl)acetic acid | | | 493.2 |

TABLE 1-6-continued

| Ex. No. | IUPAC name | structural formula | salt | MS |
|---|---|---|---|---|
| 32 | (3-((1-(5-methoxy-2-(1,1,1-trifluoropropan-2-yl)phenyl)piperidin-4-yl)methoxy)-6,7-dihydro-5H-cyclopenta[c]pyridin-5-yl)acetic acid | | | 493.2 |
| 33 | (6-((1-(5-methoxy-2-(4,4,4-trifluorobutyl)phenyl)-piperidin-4-yl)methoxy)-3,4-dihydro-2H-pyrano[2,3-c]pyridin-4-yl)acetic acid | | | 523.2 |

TABLE 1-7

| Ex. No. | IUPAC name | structural formula | salt | MS |
|---|---|---|---|---|
| 34 | (3-((1-(5-methoxy-2-(4,4,4-trifluorobutyl)phenyl)-piperidin-4-yl)methoxy)-6,7-dihydro-5H-cyclopenta[c]pyridin-5-yl)acetic acid | | | 507.2 |
| 35 | (3-((1-(5-methoxy-2-(1,1,1-trifluoropropan-2-yl)phenyl)piperidin-4-yl)methoxy)-6,7-dihydro-5H-cyclopenta[c]pyridin-5-yl)acetic acid | | | 493.2 |

TABLE 1-7-continued

| Ex. No. | IUPAC name | structural formula | salt | MS |
|---|---|---|---|---|
| 36 | (6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid | | | 578.2 |
| 37 | (6-((1-(5-methoxy-2-(1-(2,2,3,3,3-pentafluoropropyl)piperidin-4-yl)phenyl)piperidin-4-yl)methoxy)-3,4-dihydro-2H-pyrano[2,3-c]pyridin-4-yl)acetic acid | | | 628.2 |
| 38 | (3-((1-(5-methoxy-2-(1-(2,2,3,3,3-pentafluoropropyl)piperidin-4-yl)phenyl)piperidin-4-yl)methoxy)-6,7-dihydro-5H-cyclopenta[c]pyridin-5-yl)acetic acid | | | 612.2 |

TABLE 1-7-continued

| Ex. No. | IUPAC name | structural formula | salt | MS |
|---|---|---|---|---|
| 39 | (6-((1-(2-((2,2-dimethylpropyl)(6-methylpyridin-2-yl)carbamoyl)-5-methoxyphenyl)piperidin-4-yl)methoxy)-3,4-dihydro-2H-pyrano[2,3-c]pyridin-4-yl)acetic acid | | | 617.2 |

TABLE 1-8

| Ex. No. | IUPAC name | structural formula | salt | MS |
|---|---|---|---|---|
| 40 | (6-((1-(2-((2,2-dimethylpropyl)(6-methylpyridin-2-yl)carbamoyl)-5-methoxyphenyl)piperidin-4-yl)methoxy)-3,4-dihydro-2H-pyrano[2,3-c]pyridin-4-yl)acetic acid (optical isomer) | | | 617.2 |
| 41 | (3-((1-(2-((2,2-dimethylpropyl)(4,6-dimethylpyrimidin-2-yl)carbamoyl)-5-methoxyphenyl)piperidin-4-yl)methoxy)-6,7-dihydro-5H-cyclopenta[c]pyridin-5-yl)acetic acid | | | 616.3 |
| 42 | (3-((1-(2-((2,2-dimethylpropyl)(6-methylpyridin-2-yl)carbamoyl)-5-methoxyphenyl)piperidin-4-yl)methoxy)-6,7-dihydro-5H-cyclopenta[c]pyridin-5-yl)acetic acid | | | 601.2 |

TABLE 1-8-continued

| Ex. No. | IUPAC name | structural formula | salt | MS |
|---|---|---|---|---|
| 43 | (6-((1-(2-((2,2-dimethylpropyl)(6-methylpyridin-2-yl)carbamoyl)-5-methoxyphenyl)piperidin-4-yl)methoxy)-3,4-dihydro-2H-pyrano[2,3-c]pyridin-4-yl)acetic acid | | | 617.3 |
| 44 | (6-((1-(2-((2,2-dimethylpropyl)(4,6-dimethylpyrimidin-2-yl)carbamoyl)-5-methoxyphenyl)piperidin-4-yl)methoxy)-2,3-dihydro-1H-inden-1-yl)acetic acid | | | 615.3 |

TABLE 1-9

| Ex. No. | IUPAC name | structural formula | salt | MS |
|---|---|---|---|---|
| 45 | (6-((1-(2-((2,2-dimethylpropyl)(6-methylpyridin-2-yl)carbamoyl)-5-methoxyphenyl)piperidin-4-yl)methoxy)-2,3-dihydro-1H-inden-1-yl)acetic acid | | | 600.2 |
| 46 | (6-((1-(2-((2,2-dimethylpropyl)(pyridin-2-yl)carbamoyl)-5-methoxyphenyl)piperidin-4-yl)methoxy)-3,4-dihydro-2H-chromen-4-yl)acetic acid | | | 602.3 |

TABLE 1-9-continued

| Ex. No. | IUPAC name | structural formula | salt | MS |
|---|---|---|---|---|
| 47 | (6-((1-(2-(4,4-dimethylpentyl)-5-methoxyphenyl)piperidin-4-yl)methoxy)-1-methyl-2,3-dihydro-1H-inden-1-yl)acetic acid | | | 508.4 |
| 48 | (6-((1-(2-(4,4-dimethylpentyl)-5-methoxyphenyl)piperidin-4-yl)methoxy)-2,3-dihydro-1H-inden-1-yl)acetic acid | | | 494.3 |

TABLE 1-10

| Ex. No. | IUPAC name | structural formula | salt | MS |
|---|---|---|---|---|
| 49 | (6-((1-(5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (optical isomer) | | | 578.3 |

TABLE 1-10-continued

| Ex. No. | IUPAC name | structural formula | salt | MS |
|---|---|---|---|---|
| 50 | (6-((1-(2-(4,4-diflurocyclohexyl)-5-methoxyphenyl)piperidin-4-yl)methoxy)-3,4-dihydro-2H-pyrano[2,3-c]pyridin-4-yl)acetic acid (optical isomer) | | | 531.3 |
| 51 | (6-((1-(5-(4,4-difluorocyclohexyl)-2-methoxypyridin-4-yl)piperidin-4-yl)methoxy)-3,4-dihydro-2H-pyrano[2,3-c]pyridin-4-yl)acetic acid (optical isomer) | | | 532.4 |
| 52 | (6-((1-(2-methoxy-5-(3,3,3-trifluoropropyl)pyridin-4-yl)piperidin-4-yl)methoxy)-3,4-dihydro-2H-pyrano[2,3-c]pyridin-4-yl)acetic acid (optical isomer) | | | 510.3 |
| 53 | (6-((1-(5-methyl-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (optical isomer) | | | 562.3 |

TABLE 1-10-continued

| Ex. No. | IUPAC name | structural formula | salt | MS |
|---|---|---|---|---|
| 54 | (6-((1-(5-methoxy-2-(4-methoxy-1-(2,2,2-trifluoroethyl)piperidin-4-yl)phenyl)piperidin-4-yl)methoxy)-3,4-dihydro-2H-pyrano[2,3-c]pyridin-4-yl)acetic acid (optical isomer) | | | 608.4 |

TABLE 1-11

| Ex. No. | IUPAC name | structural formula | salt | MS |
|---|---|---|---|---|
| 55 | (6-((1-(2-methoxy-5-(4,4,4-trifluorobutyl)pyridin-4-yl)piperidin-4-yl)methoxy)-3,4-dihydro-2H-pyrano[2,3-c]pyridin-4-yl)acetic acid (optical isomer) | | | 524.3 |
| 56 | (6-((1-(5-ethyl-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (optical isomer) | | | 576.3 |

TABLE 1-11-continued

| Ex. No. | IUPAC name | structural formula | salt | MS |
|---|---|---|---|---|
| 57 | (6-((1-(5-chloro-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (optical isomer) | | | 582.4 |
| 58 | (6-((1-(2-(2,2-dimethyltetrahydro-2H-pyran-4-yl)-5-methoxyphenyl)piperidin-4-yl)methoxy)-3,4-dihydro-2H-pyrano[2,3-c]pyridin-4-yl)acetic acid | | | 525.3 |
| 59 | (6-((1-(5-methoxy-2-((3,3,4,4-tetrafluoropyrrolidin-1-yl)methyl)phenyl)piperidin-4-yl)methoxy)-3,4-dihydro-2H-pyrano[2,3-c]pyridin-4-yl)acetic acid (optical isomer) | | | 568.3 |

Reference Example 4

(6-((1-(2-fluoro-3-methoxy-6-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (Optical Isomer)

A) ethyl 1-(2-fluoro-3-methoxy-6-nitrophenyl)piperidine-4-carboxylate

To a mixture of 2,3-difluoro-1-methoxy-4-nitrobenzene (4.92 g), potassium carbonate (3.09 g) and DMF (30 mL) was added ethyl piperidine-4-carboxylate (4.91 g), and the mixture was stirred under a nitrogen atmosphere at 60° C. for 1 hr. To the reaction mixture was added water at room temperature, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (8.48 g). MS: [M+H]$^+$ 327.2.

B) ethyl 1-(6-amino-2-fluoro-3-methoxyphenyl)piperidine-4-carboxylate

A mixture of ethyl 1-(2-fluoro-3-methoxy-6-nitrophenyl)piperidine-4-carboxylate (2.00 g), 10% palladium carbon (240 mg), THF (10 mL) and EtOH (10 mL) was stirred under a hydrogen atmosphere at normal pressure at room temperature for 4 hr. The catalyst was removed by filtration and the filtrate was concentrated under reduced pressure. The residue was purified by silica gel column chromatography (ethyl acetate/hexane) to give the title compound (1.72 g). MS: [M+H]$^+$ 297.2.

C) ethyl 1-(2-fluoro-6-iodo-3-methoxyphenyl)piperidine-4-carboxylate

To a mixture of ethyl 1-(6-amino-2-fluoro-3-methoxyphenyl)piperidine-4-carboxylate (1.72 g) and acetonitrile (10 mL) was added 2N hydrochloric acid (9.1 mL) at 0° C., and the mixture was stirred at the same temperature for 30 min. To the mixture was added a mixture of sodium nitrite (521 mg) and water (2 mL) at 0° C., and the mixture was stirred under a nitrogen atmosphere at the same temperature for 30 min. To the mixture was added a mixture of potassium iodide (2.89 g) and water (4 mL) at 0° C., and the mixture was stirred under a nitrogen atmosphere at 60° C. for 1 hr. To the reaction mixture was added saturated aqueous sodium hydrogen carbonate solution at room temperature, and the mixture was extracted with ethyl acetate. The organic layer was separated, washed with saturated aqueous sodium thiosulfate solution and saturated brine, dried over anhydrous magnesium sulfate and concentrated under reduced pressure. The residue was purified by silica gel column chromatography (ethyl acetate/hexane) to give the title compound (2.19 g). MS: [M+H]$^+$408.0.

D) tert-butyl 4-(2-(4-(ethoxycarbonyl)piperidin-1-yl)-3-fluoro-4-methoxyphenyl)-3,6-dihydropyridine-1(2H)-carboxylate A mixture of ethyl 1-(2-fluoro-6-iodo-3-methoxyphenyl)piperidine-4-carboxylate (500 mg), tert-butyl 4-(4,4,5,5-tetramethyl-1,3,2-dioxaborolan-2-yl)-3,6-dihydropyridine-1(2H)-carboxylate (759 mg), [1,1'-bis(diphenylphosphino)ferrocene]palladium(II) dichloride (180 mg), 2 M aqueous sodium carbonate solution (1.35 mL) and DMF (10 mL) was stirred under a nitrogen atmosphere at 100° C. for 4 hr. To the reaction mixture was added water at room temperature, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (440 mg). MS: [M+H]$^+$ 463.3.

E) tert-butyl 4-(2-(4-(ethoxycarbonyl)piperidin-1-yl)-3-fluoro-4-methoxyphenyl)piperidine-1-carboxylate A mixture of tert-butyl 4-(2-(4-(ethoxycarbonyl)piperidin-1-yl)-3-fluoro-4-methoxyphenyl)-3,6-dihydropyridine-1(2H)-carboxylate (440 mg), 10% palladium carbon (150 mg) and THF (10 mL) was stirred under a hydrogen atmosphere at normal pressure at room temperature for 10 hr. The catalyst was removed by filtration and the filtrate was concentrated under reduced pressure to give the title compound (500 mg). MS: [M+H]$^+$ 465.3.

F) ethyl 1-(2-fluoro-3-methoxy-6-(1-(2,2,2-trifluoroethyl)piperidin-4-yl)phenyl)piperidine-4-carboxylate To a mixture of tert-butyl 4-(2-(4-(ethoxycarbonyl)piperidin-1-yl)-3-fluoro-4-methoxyphenyl)piperidine-1-carboxylate (500 mg) and ethyl acetate (6 mL) was added 4N hydrogen chloride ethyl acetate solution (4 mL) at room temperature. The mixture was stirred under a nitrogen atmosphere at the same temperature for 40 min, and the reaction mixture was concentrated. To a mixture of the obtained residue, TEA (1.50 mL) and acetonitrile (10 mL) was added 2,2,2-trifluoroethyl trifluoromethanesulfonate (0.773 mL) at room temperature. The mixture was stirred under a nitrogen atmosphere at 60° C. for 20 min, and the reaction mixture was concentrated under reduced pressure. To the residue was added ethyl acetate, insoluble material was removed by filtration, and the filtrate was concentrated under reduced pressure. The residue was purified by silica gel column chromatography (ethyl acetate/hexane) to give the title compound (36.0 mg). MS: [M+H]$^+$ 447.2.

G) (1-(2-fluoro-3-methoxy-6-(1-(2,2,2-trifluoroethyl)piperidin-4-yl)phenyl)piperidin-4-yl)methanol To a mixture of lithium aluminum hydride (92.0 mg) and Et$_2$O (5 mL) was added a solution of ethyl 1-(2-fluoro-3-methoxy-6-(1-(2,2,2-trifluoroethyl)piperidin-4-yl)phenyl)piperidine-4-carboxylate (360 mg) in Et$_2$O (4 mL) at 0° C. The mixture was stirred at the same temperature for 20 min. To the mixture were added water and 1N aqueous sodium hydroxide solution, the obtained precipitate was removed by filtration, and the filtrate was concentrated under reduced pressure. The residue was purified by silica gel column chromatography (ethyl acetate/hexane) to give the title compound (270 mg). MS: [M+H]$^+$ 405.3.

H) ethyl (6-((1-(2-fluoro-3-methoxy-6-(1-(2,2,2-trifluoroethyl)piperidin-4-yl)phenyl)piperidin-4-yl)methoxy)-3,4-dihydro-2H-pyrano[2,3-c]pyridin-4-yl)acetate (Optical Isomer)

To a mixture of (1-(2-fluoro-3-methoxy-6-(1-(2,2,2-trifluoroethyl)piperidin-4-yl)phenyl)piperidin-4-yl)methanol (150 mg), ethyl (6-hydroxy-3,4-dihydro-2H-pyrano[2,3-c]pyridin-4-yl)acetate (optical isomer) (60.0 mg) and toluene (3 mL) was added (tributylphosphoranylidene)acetonitrile (122 mg) at room temperature. The mixture was stirred under a nitrogen atmosphere at 100° C. for 5 hr. The reaction mixture was concentrated under reduced pressure and the residue was purified by silica gel column chromatography (ethyl acetate/hexane) to give the title compound (102 mg). MS: [M+H]$^+$ 624.3.

I) (6-((1-(2-fluoro-3-methoxy-6-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (Optical Isomer)

To a mixture of ethyl (6-((1-(2-fluoro-3-methoxy-6-(1-(2,2,2-trifluoroethyl)piperidin-4-yl)phenyl)piperidin-4-yl)methoxy)-3,4-dihydro-2H-pyrano[2,3-c]pyridin-4-yl)acetate (optical isomer) (102 mg), THF (3 mL) and MeOH (1.5 mL) was added 1N aqueous sodium hydroxide solution (2.19 mL) at room temperature. The mixture was stirred at 60° C. for 2 hr. The reaction mixture was neutralized with 1N hydrochloric acid at room temperature and extracted with ethyl acetate. The organic layer was separated, washed with water and saturated brine, dried over anhydrous magnesium sulfate and concentrated under reduced pressure. The obtained solid was crystallized from ethyl acetate/hexane to give the title compound (84 mg). $^1$H NMR (300 MHz, DMSO-d$_6$) δ 1.19-1.40 (2H, m), 1.60 (4H, br s), 1.80 (4H, br d, J=10.5 Hz), 1.99-2.09 (1H, m), 2.37-2.47 (2H, m), 2.76-3.27 (12H, m), 3.77 (3H, s), 3.99-4.20 (4H, m), 6.69 (1H, s), 6.87-6.98 (2H, m), 7.66 (1H, s), 12.10-12.80 (1H, m).

The Reference Example compounds are shown in the following Tables. In the Tables, MS shows Found. The compounds of Reference Examples 5-7 in the following Tables were produced according to the methods shown in the above-mentioned Examples or Reference Examples or methods analogous thereto.

TABLE 2

| Ref. Ex. No. | IUPAC name | structural formula | salt | MS |
|---|---|---|---|---|
| 4 | (6-((1-(2-fluoro-3-methoxy-6-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (optical isomer) | 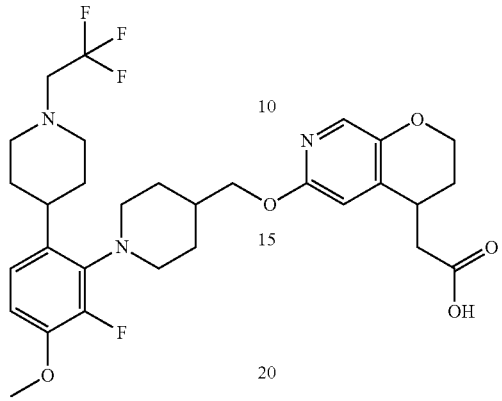 [SMILES: COc1ccc(C2CCN(CC(F)(F)F)CC2)c(N2CCC(COc3cc4c(cn3)OCCC4CC(=O)O)CC2)c1F] | | 596.3 |
| 5 | (6-((1-(3-fluoro-5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (optical isomer) | 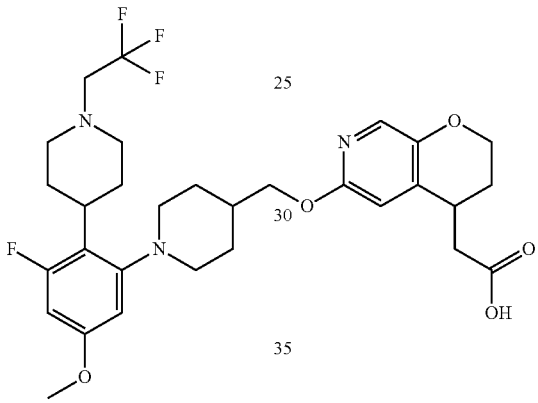 [SMILES: COc1cc(F)c(C2CCN(CC(F)(F)F)CC2)c(N2CCC(COc3cc4c(cn3)OCCC4CC(=O)O)CC2)c1] | | 596.3 |
| 6 | (6-((1-(2-((dicyclopropylmethyl)-sulfonyl)-5-methoxyphenyl)piperidin-4-yl)methoxy)-3,4-dihydro-2H-pyrano[2,3-c]pyridin-4-yl)acetic acid (optical isomer) | 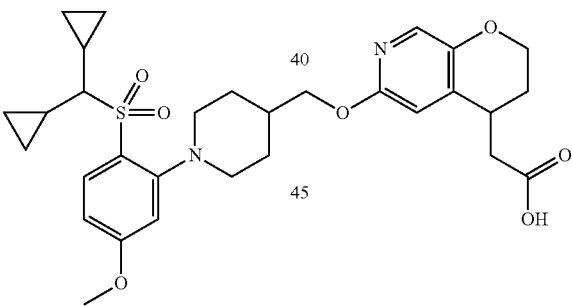 [SMILES: COc1ccc(S(=O)(=O)C(C2CC2)C2CC2)c(N2CCC(COc3cc4c(cn3)OCCC4CC(=O)O)CC2)c1] | | 571.3 |
| 7 | (6-((1-(4-fluoro-5-methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid (optical isomer) | 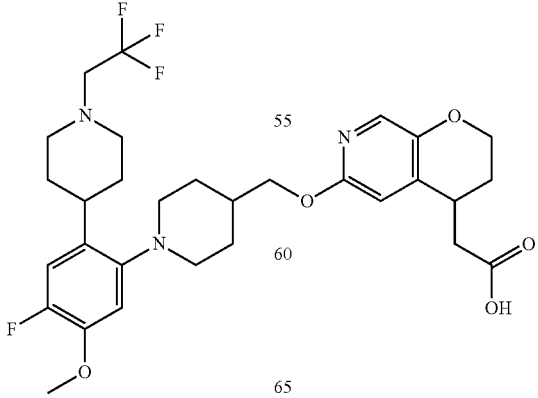 [SMILES: COc1cc(N2CCC(COc3cc4c(cn3)OCCC4CC(=O)O)CC2)c(C2CCN(CC(F)(F)F)CC2)cc1F] | | 596.3 |

Experimental Example 1

Evaluation of Human GPR40 Agonist Activity with Increase in Intracellular $Ca^{2+}$ Concentration as an Index CHO(dhfr−) cells that stably expressed human GPR40 were suspended in MEMα (Wako Pure Chemical Industries, Ltd.) containing 10% dialyzed serum (Thermo Fisher Scientific), 10 mM HEPES (Thermo Fisher Scientific), 100 U/mL penicillin, 100 μg/mL streptomycin (Wako Pure Chemical Industries, Ltd.), and plated on a 384 well black/clear cell culture plate at 10,000 cells/well. After culture overnight in a $CO_2$ incubator at 37° C., the culture supernatant was removed, and loading buffer [$Ca^{2+}$ probe attached to Calcium Kit II-iCellux (DOJINDO) was dissolved in assay buffer (20 mM HEPES, 0.1% fatty acid-free BSA (Wako Pure Chemical Industries, Ltd.), 2.5 mM probenecid (DOJINDO)-containing HBSS (Thermo Fisher Scientific))] was added at 30 μL/well. After leaving for 1 hr at room temperature under light shielding, assay buffer containing the test compound at a final concentration of 1 μM was added at 10 μL/well in fluorescence plate reader FLIPR Tetra (Molecular Devices), and the fluorescence amount was successively measured. Human GPR40 agonist activity was calculated using an increase in the intracellular $Ca^{2+}$ concentration as an index, wherein the activity of 10 μM of the compound of WO 2015/020184 (Example 153: 3-cyclopropyl-3-(2-((1-(2-((2-fluoro-2-methylpropyl)(4-methylpyridin-2-yl)carbamoyl)-5-methoxyphenyl)piperidin-4-yl)methoxy)pyridin-4-yl)propanoic acid) was 100%, and the activity when DMSO was added instead of the test compound was 0%. The results are shown in Table 3.

TABLE 3

| Ex. No. | activity |
|---|---|
| 1 | 107% |
| 2 | 108% |
| 3 | 109% |
| 4 | 108% |
| 5 | 111% |
| 6 | 59% |
| 7 | 107% |
| 8 | 103% |
| 9 | 104% |
| 10 | 105% |
| 11 | 107% |
| 17 | 58% |
| 18 | 41% |
| 28 | 54% |
| 29 | 65% |
| 36 | 110% |

Formulation Example 1 (Production of Capsule)

| | |
|---|---|
| 1) compound of Example 1 | 30 mg |
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2 (Production of Tablets)

| | |
|---|---|
| 1) compound of Example 1 | 33 g |
| 2) lactose | 50 g |
| 3) cornstarch | 15 g |
| 4) calcium carboxymethylcellulose | 44 g |
| 5) magnesium stearate | 1 g |
| 1000 tablets | total 140 g |

The entire amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Ex. 1 per tablet are obtained.

INDUSTRIAL APPLICABILITY

The compound of the present invention may have superior GPR40 agonist activity and GLP-1 secretagogue action, and may be useful as an agent for the prophylaxis or treatment of diabetes and the like.

This application is based on a patent application No. 2017-072813 filed in Japan, the contents of which are incorporated in full herein.

The invention claimed is:

1. A compound represented by the formula (I):

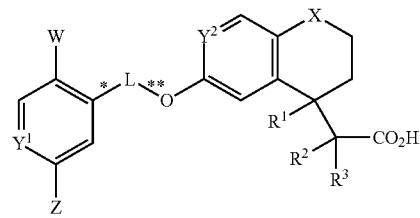

wherein X is an oxygen atom or a bond;
$Y^1$ and $Y^2$ are each independently CH or N;
Z is an optionally substituted alkyl group, an optionally substituted alkoxy group or a halogen atom;
W is an optionally substituted alkyl group, an optionally substituted alkoxy group, —$NR^{W1}R^{W2}$, an optionally substituted carbamoyl group or an optionally substituted cyclic group;
$R^{W1}$ is an optionally substituted alkyl group or an acyl group;
$R^{W2}$ is a hydrogen atom or a substituent;
L is

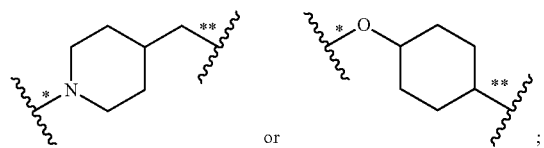 [SMILES: *CC1CCN(*)CC1 ; *OC1CCC(*)CC1]

and
$R^1$, $R^2$ and $R^3$ are each independently a hydrogen atom or a substituent; or
$R^1$ and $R^2$ are optionally bonded to each other to form, together with each adjacent carbon atom, an optionally further substituted 3- to 6-membered ring,
or a salt thereof.

2. The compound according to claim 1, wherein
Z is a $C_{1-6}$ alkoxy group;
W is
(1) a $C_{1-10}$ alkyl group optionally substituted by 1 to 5 halogen atoms,
(2) a $C_{1-10}$ alkoxy group optionally substituted by 1 to 5 halogen atoms,
(3) a $C_{6-14}$ aryl group optionally substituted by 1 to 5 substituents selected from
  (a) a $C_{1-6}$ alkoxy group optionally substituted by 1 to 5 halogen atoms, and
  (b) a 3- to 14-membered non-aromatic heterocyclic group,
(4) a 5- to 14-membered aromatic heterocyclic group optionally substituted by 1 to 5 substituents selected from
  (a) a $C_{1-6}$ alkyl group optionally substituted by 1 to 5 halogen atoms, and
  (b) a $C_{1-6}$ alkoxy group optionally substituted by 1 to 5 halogen atoms,
(5) a 3- to 14-membered non-aromatic heterocyclic group optionally substituted by 1 to 5 substituents selected from $C_{1-6}$ alkyl groups optionally substituted by 1 to 5 halogen atoms,
(6) a carbamoyl group optionally mono- or di-substituted by substituent(s) selected from
  (a) a $C_{1-6}$ alkyl group, and
  (b) a 5- to 14-membered aromatic heterocyclic group optionally substituted by 1 to 5 $C_{1-6}$ alkyl groups, or
(7) a $C_{3-10}$ cycloalkyl group optionally substituted by 1 to 5 halogen atoms;
  $R^1$ is a hydrogen atom or a $C_{1-6}$ alkyl group, and $R^2$ and $R^3$ are each a hydrogen atom;
or a salt thereof.

3. The compound according to claim 1, wherein
X is an oxygen atom or a bond;
$Y^1$ is CH or N;
$Y^2$ is N;
Z is a $C_{1-6}$ alkoxy group;
W is
(1) a $C_{1-6}$ alkyl group optionally substituted by 1 to 5 halogen atoms,
(2) a $C_{1-6}$ alkoxy group optionally substituted by 1 to 5 halogen atoms,
(3) a 3- to 14-membered non-aromatic heterocyclic group optionally substituted by 1 to 5 substituents selected from $C_{1-6}$ alkyl groups optionally substituted by 1 to 5 halogen atoms,
(4) a carbamoyl group optionally mono- or di-substituted by substituent(s) selected from
  (a) a $C_{1-6}$ alkyl group, and
  (b) a 5- to 14-membered aromatic heterocyclic group optionally substituted by 1 to 5 $C_{1-6}$ alkyl groups, or
(5) a $C_{3-10}$ cycloalkyl group optionally substituted by 1 to 5 halogen atoms;
L is

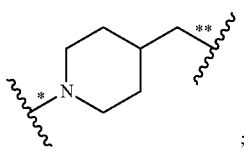 [SMILES: *CC1CCN(*)CC1]

and
$R^1$, $R^2$ and $R^3$ are each a hydrogen atom;
or a salt thereof.

4. The compound according to claim 1, wherein
X is an oxygen atom or a bond;
$Y^1$ is CH or N;
$Y^2$ is N;
Z is a $C_{1-6}$ alkoxy group;
W is
(1) a $C_{1-6}$ alkyl group optionally substituted by 1 to 5 halogen atoms,
(2) a 3- to 14-membered nonaromatic heterocyclic group optionally substituted by 1 to 5 substituents selected from $C_{1-6}$ alkyl groups optionally substituted by 1 to 5 halogen atoms,
(3) a carbamoyl group optionally mono- or di-substituted by substituent(s) selected from
  (a) a $C_{1-6}$ alkyl group, and
  (b) a 5- to 14-membered aromatic heterocyclic group optionally substituted by 1 to 5 $C_{1-6}$ alkyl groups, or
(4) a $C_{3-10}$ cycloalkyl group optionally substituted by 1 to 5 halogen atoms;
L is

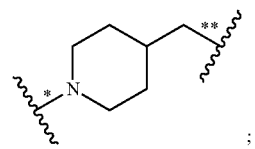 [SMILES: *CC1CCN(*)CC1]

and
$R^1$, $R^2$ and $R^3$ are each a hydrogen atom;
or a salt thereof.

5. The compound according to claim 1, which is selected from the group consisting of
  (6-((1-(2-((2,2-dimethylpropyl)(6-methylpyridin-2-yl)carbamoyl)-5-methoxyphenyl)piperidin-4-yl)methoxy)-3,4-dihydro-2H-pyrano[2,3-c]pyridin-4-yl)acetic acid or a salt thereof,
  (6-((1-(5-Methoxy-2-(3,3,3-trifluoropropyl)phenyl)piperidin-4-yl)methoxy)-3,4-dihydro-2H-pyrano[2,3-c]pyridin-4-yl)acetic acid or a salt thereof,
  (6-((1-(2-Methoxy-5-(2,2,3,3,3-pentafluoropropoxy)pyridin-4-yl)piperidin-4-yl)methoxy)-3,4-dihydro-2H-pyrano[2,3-c]pyridin-4-yl)acetic acid or a salt thereof,
  (6-((1-(5-Methoxy-2-(1-(2,2,2-trifluoroethyl)piperidin-4-yl)phenyl)piperidin-4-yl)methoxy)-3,4-dihydro-2H-pyrano[2,3-c]pyridin-4-yl)acetic acid or a salt thereof,
  (6-((1-(2-(4,4-Difluorocyclohexyl)-5-methoxyphenyl)piperidin-4-yl)methoxy)-3,4-dihydro-2H-pyrano[2,3-c]pyridin-4-yl)acetic acid or a salt thereof, and
  (6-((1-(2-Methoxy-5-(3,3,3-trifluoropropyl)pyridin-4-yl)piperidin-4-yl)methoxy)-3,4-dihydro-2H-pyrano[2,3-c]pyridin-4-yl)acetic acid or a salt thereof.

6. A medicament comprising the compound according to claim 1 or a salt thereof.

7. The medicament according to claim 6, which is a GPR40 receptor function regulator.

8. The medicament according to claim 6, which is a prophylactic or therapeutic agent for diabetes.

9. A method for regulating GPR40 receptor function in a mammal, comprising administering an effective amount of the compound according to claim 1 or a salt thereof to the mammal.

10. A method for regulating GPR40 receptor function in a mammal, which is for preventing or treating obesity or diabetes in a mammal, comprising administering an effective amount of the compound according to claim 1 or a salt thereof to the mammal.

\* \* \* \* \*